(12) United States Patent
De Groot et al.

(10) Patent No.: US 7,684,049 B2
(45) Date of Patent: *Mar. 23, 2010

(54) INTERFEROMETER AND METHOD FOR MEASURING CHARACTERISTICS OF OPTICALLY UNRESOLVED SURFACE FEATURES

(75) Inventors: Peter De Groot, Middletown, CT (US); Michael J. Darwin, Beaverton, OR (US); Robert Stoner, Duxbury, MA (US); Gregg M. Gallatin, Newtown, CT (US); Xavier Colonna De Lega, Middletown, CT (US)

(73) Assignee: Zygo Corporation, Middlefield, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/017,531

(22) Filed: Jan. 22, 2008

(65) Prior Publication Data

US 2008/0266574 A1    Oct. 30, 2008

Related U.S. Application Data

(63) Continuation of application No. 11/525,355, filed on Sep. 21, 2006, now Pat. No. 7,324,214, and a continuation-in-part of application No. 10/795,579, filed on Mar. 8, 2004, now Pat. No. 7,271,918.

(60) Provisional application No. 60/737,016, filed on Nov. 15, 2005, provisional application No. 60/452,615, filed on Mar. 6, 2003, provisional application No. 60/452,465, filed on Mar. 6, 2003, provisional application No. 60/539,437, filed on Jan. 26, 2004.

(51) Int. Cl.
*G01B 11/02* (2006.01)

(52) U.S. Cl. .................................... 356/511; 356/497

(58) Field of Classification Search ................ 356/497, 356/503, 511–514, 516; 359/370
See application file for complete search history.

(56) References Cited

U.S. PATENT DOCUMENTS

| | | |
|---|---|---|
| 2,612,074 A | 9/1952 | Mirau |
| 4,188,122 A | 2/1980 | Massie et al. |
| 4,199,219 A | 4/1980 | Suzki et al. |
| 4,340,306 A | 7/1982 | Balasubramanian |

(Continued)

FOREIGN PATENT DOCUMENTS

DE    4108944    9/1992

(Continued)

OTHER PUBLICATIONS

C. Akcay et al., "Spectral shaping to improve the point spread function in optical coherence tomography", *Optics Letters*, vol. 28, No. 20, pp. 1921-1923 (Oct. 15, 2003).

(Continued)

*Primary Examiner*—Michael A Lyons
(74) *Attorney, Agent, or Firm*—Fish & Richardson P.C.

(57) ABSTRACT

Disclosed is an interferometry analysis method that includes comparing information derivable from multiple interferometry signals corresponding to different surface locations of a test object to information corresponding to multiple models of the test object, wherein the multiple models are parameterized by a series of characteristics that relate to one or more under-resolved lateral features of the test object; and outputting information about the under-resolved surface feature based on the comparison.

10 Claims, 43 Drawing Sheets

U.S. PATENT DOCUMENTS

| | | | |
|---|---|---|---|
| 4,355,903 A | 10/1982 | Sandercock | |
| 4,523,846 A | 6/1985 | Breckinridge et al. | |
| 4,576,479 A | 3/1986 | Downs | |
| 4,583,858 A | 4/1986 | Lebling et al. | |
| 4,618,262 A | 10/1986 | Maydan et al. | |
| 4,639,139 A | 1/1987 | Wyant et al. | |
| 4,660,980 A | 4/1987 | Takabayashi et al. | |
| 4,710,642 A | 12/1987 | McNeil | |
| 4,806,018 A | 2/1989 | Falk | |
| 4,818,110 A | 4/1989 | Davidson | |
| 4,869,593 A | 9/1989 | Biegen | |
| 4,923,301 A | 5/1990 | White | |
| 4,948,253 A | 8/1990 | Biegen | |
| 4,964,726 A | 10/1990 | Kleinknecht et al. | |
| 4,999,014 A | 3/1991 | Gold et al. | |
| 5,042,949 A | 8/1991 | Greenberg et al. | |
| 5,042,951 A | 8/1991 | Gold et al. | |
| 5,073,018 A | 12/1991 | Kind et al. | |
| 5,112,129 A | 5/1992 | Davidson et al. | |
| 5,129,724 A | 7/1992 | Brophy et al. | |
| 5,133,601 A | 7/1992 | Cohen et al. | |
| 5,135,307 A | 8/1992 | de Groot et al. | |
| 5,153,669 A | 10/1992 | DeGroot | |
| 5,164,790 A | 11/1992 | McNeil et al. | |
| 5,166,751 A | 11/1992 | Massig | |
| 5,173,746 A | 12/1992 | Brophy | |
| 5,194,918 A | 3/1993 | Kino et al. | |
| 5,241,369 A | 8/1993 | McNeil et al. | |
| 5,301,010 A | 4/1994 | Jones et al. | |
| 5,355,221 A | 10/1994 | Cohen et al. | |
| 5,384,717 A | 1/1995 | Ebenstein | |
| 5,386,119 A | 1/1995 | Ledger | |
| 5,390,023 A | 2/1995 | Biegen | |
| 5,398,113 A | 3/1995 | de Groot | |
| 5,402,234 A | 3/1995 | Deck | |
| 5,459,564 A | 10/1995 | Chivers | |
| 5,471,303 A | 11/1995 | Ai et al. | |
| 5,481,811 A | 1/1996 | Smith | |
| 5,483,064 A | 1/1996 | Frey et al. | |
| 5,539,571 A | 7/1996 | Cabib et al. | |
| 5,543,841 A | 8/1996 | Kanamori | |
| 5,555,471 A | 9/1996 | Xu et al. | |
| 5,587,792 A | 12/1996 | Nishizawa et al. | |
| 5,589,938 A | 12/1996 | Deck | |
| 5,602,643 A | 2/1997 | Barrett | |
| 5,633,714 A | 5/1997 | Nyyssonen | |
| 5,640,270 A | 6/1997 | Aziz et al. | |
| 5,703,692 A | 12/1997 | McNeil et al. | |
| 5,757,502 A | 5/1998 | Weling | |
| 5,774,224 A | 6/1998 | Kerstens | |
| 5,777,740 A | 7/1998 | Lacey et al. | |
| 5,777,742 A | 7/1998 | Marron | |
| 5,784,164 A | 7/1998 | Deck et al. | |
| 5,856,871 A | 1/1999 | Cabib et al. | |
| 5,867,276 A | 2/1999 | McNeil et al. | |
| 5,880,838 A | 3/1999 | Marx et al. | |
| 5,900,633 A | 5/1999 | Solomon et al. | |
| 5,912,741 A | 6/1999 | Carter et al. | |
| 5,923,423 A | 7/1999 | Sawatari et al. | |
| 5,943,134 A | 8/1999 | Yamaguchi et al. | |
| 5,953,124 A | 9/1999 | Deck | |
| 5,956,141 A | 9/1999 | Hayashi | |
| 5,959,735 A | 9/1999 | Maris et al. | |
| 5,963,329 A | 10/1999 | Conrad et al. | |
| 6,028,670 A | 2/2000 | Deck | |
| 6,160,621 A | 12/2000 | Perry et al. | |
| 6,172,452 B1 | 1/2001 | Itaya et al. | |
| 6,242,739 B1 | 6/2001 | Cherkassky | |
| 6,249,351 B1 | 6/2001 | de Groot | |
| H1972 H | 7/2001 | Inoue | |
| 6,259,521 B1 | 7/2001 | Miller et al. | |
| 6,275,297 B1 | 8/2001 | Zalicki | |
| 6,377,349 B1 | 4/2002 | Fercher | |
| 6,381,009 B1 | 4/2002 | McGahan | |
| 6,392,749 B1 | 5/2002 | Meeks et al. | |
| 6,417,109 B1 | 7/2002 | Jordan et al. | |
| 6,429,943 B1 | 8/2002 | Opsal et al. | |
| 6,449,048 B1 | 9/2002 | Olszak | |
| 6,449,066 B1 | 9/2002 | Arns et al. | |
| 6,483,580 B1 | 11/2002 | Xu et al. | |
| 6,500,591 B1 | 12/2002 | Adams | |
| 6,507,405 B1 | 1/2003 | Grek et al. | |
| 6,525,825 B2 | 2/2003 | de Groot | |
| 6,545,761 B1 | 4/2003 | Aziz et al. | |
| 6,545,763 B1 | 4/2003 | Kim et al. | |
| 6,590,656 B2 | 7/2003 | Xu et al. | |
| 6,597,460 B2 | 7/2003 | Groot et al. | |
| 6,611,330 B2 | 8/2003 | Lee et al. | |
| 6,624,894 B2 | 9/2003 | Olszak et al. | |
| 6,633,389 B1 | 10/2003 | Poris et al. | |
| 6,633,831 B2 | 10/2003 | Nikoonahad et al. | |
| 6,636,322 B1 | 10/2003 | Terashita | |
| 6,694,284 B1 | 2/2004 | Nikoonahad et al. | |
| 6,714,307 B2 | 3/2004 | de Groot et al. | |
| 6,721,094 B1 | 4/2004 | Sinclair et al. | |
| 6,741,357 B2 | 5/2004 | Wang et al. | |
| 6,741,360 B2 | 5/2004 | D'Agraives et al. | |
| 6,775,006 B2 | 8/2004 | De Groot et al. | |
| 6,775,009 B2 | 8/2004 | Hill | |
| 6,822,745 B2 | 11/2004 | De Groot et al. | |
| 6,856,384 B1 | 2/2005 | Rovira | |
| 6,888,638 B1 | 5/2005 | Hill | |
| 6,891,627 B1 | 5/2005 | Levy et al. | |
| 6,909,509 B2 | 6/2005 | DeGroot | |
| 6,925,860 B1 | 8/2005 | Poris et al. | |
| 6,940,604 B2 | 9/2005 | Jung et al. | |
| 6,956,658 B2 | 10/2005 | Meeks et al. | |
| 6,956,660 B2 | 10/2005 | Meeks et al. | |
| 6,985,232 B2 | 1/2006 | Sezginer | |
| 6,989,905 B2 | 1/2006 | De Groot | |
| 6,999,180 B1 | 2/2006 | Janik et al. | |
| 7,012,700 B2 | 3/2006 | de Groot et al. | |
| 7,018,271 B2 | 3/2006 | Wiswesser et al. | |
| 7,038,850 B2 | 5/2006 | Chang et al. | |
| 7,046,371 B2 | 5/2006 | de Lega et al. | |
| 7,061,623 B2 | 6/2006 | Davidson | |
| 7,068,376 B2 | 6/2006 | De Groot | |
| 7,088,451 B2 | 8/2006 | Sezginer | |
| 7,102,761 B2 | 9/2006 | De Lega et al. | |
| 7,106,454 B2 | 9/2006 | de Groot et al. | |
| 7,119,909 B2 | 10/2006 | Unruh et al. | |
| 7,139,081 B2 | 11/2006 | De Groot | |
| 7,139,083 B2 | 11/2006 | Fielden et al. | |
| 7,142,311 B2 | 11/2006 | De Lega | |
| 7,177,030 B2 | 2/2007 | Leizerson | |
| 7,205,518 B2 | 4/2007 | Neuvonen | |
| 7,239,398 B2 * | 7/2007 | De Groot et al. | 356/511 |
| 7,271,918 B2 * | 9/2007 | De Groot et al. | 356/511 |
| 7,283,248 B2 | 10/2007 | Hill | |
| 7,289,225 B2 | 10/2007 | de Groot | |
| 7,298,494 B2 | 11/2007 | de Groot | |
| 7,304,747 B2 | 12/2007 | De Lega | |
| 7,315,382 B2 | 1/2008 | de Groot | |
| 7,324,210 B2 | 1/2008 | de Groot et al. | |
| 7,324,214 B2 * | 1/2008 | De Groot et al. | 356/511 |
| 7,403,289 B2 | 7/2008 | de Groot | |
| 7,428,057 B2 | 9/2008 | De Lega et al. | |
| 7,466,429 B2 | 12/2008 | de Groot | |
| 2002/0015146 A1 | 2/2002 | Meeks et al. | |
| 2002/0135775 A1 | 9/2002 | de Groot et al. | |
| 2002/0148955 A1 | 10/2002 | Hill | |
| 2002/0196450 A1 | 12/2002 | Olszak et al. | |
| 2003/0011784 A1 | 1/2003 | de Groot et al. | |
| 2003/0048458 A1 | 3/2003 | Mieher et al. | |

| | | |
|---|---|---|
| 2003/0075721 A1 | 4/2003 | Li |
| 2003/0112444 A1 | 6/2003 | Yang et al. |
| 2003/0137671 A1 | 7/2003 | de Groot et al. |
| 2003/0197871 A1 | 10/2003 | de Groot |
| 2004/0027576 A1 | 2/2004 | De Groot et al. |
| 2004/0075843 A1 | 4/2004 | Marron et al. |
| 2004/0085544 A1 | 5/2004 | de Groot et al. |
| 2004/0185582 A1 | 9/2004 | Kueny |
| 2004/0189999 A1 | 9/2004 | de Groot et al. |
| 2004/0233442 A1 | 11/2004 | Mieher et al. |
| 2004/0233444 A1 | 11/2004 | Mieher et al. |
| 2004/0246493 A1 | 12/2004 | Kim et al. |
| 2005/0024773 A1 | 2/2005 | Lille |
| 2005/0057757 A1 | 3/2005 | de Lega et al. |
| 2005/0068540 A1 | 3/2005 | de Groot et al. |
| 2005/0073692 A1 | 4/2005 | de Groot et al. |
| 2005/0078318 A1 | 4/2005 | de Groot |
| 2005/0078319 A1 | 4/2005 | de Groot |
| 2005/0088663 A1 | 4/2005 | de Groot et al. |
| 2005/0146727 A1 | 7/2005 | Hill |
| 2005/0179911 A1 | 8/2005 | Boomgarden et al. |
| 2005/0225769 A1 | 10/2005 | Bankhead et al. |
| 2005/0237534 A1 | 10/2005 | Deck |
| 2005/0237537 A1 | 10/2005 | Leizerson et al. |
| 2006/0012582 A1 | 1/2006 | de Lega |
| 2006/0072104 A1 | 4/2006 | Engel et al. |
| 2006/0119841 A1 | 6/2006 | Saunders et al. |
| 2006/0158657 A1 | 7/2006 | de Lega et al. |
| 2006/0158658 A1 | 7/2006 | de Lega et al. |
| 2006/0158659 A1 | 7/2006 | de Lega et al. |
| 2006/0170932 A1 | 8/2006 | Hayashi et al. |
| 2006/0187465 A1 | 8/2006 | de Groot |
| 2006/0262321 A1 | 11/2006 | de Groot |
| 2007/0008551 A1 | 1/2007 | Tang |
| 2007/0046953 A1 | 3/2007 | de Groot et al. |
| 2007/0081167 A1 | 4/2007 | de Groot et al. |
| 2007/0091317 A1 | 4/2007 | Freischlad et al. |
| 2007/0091318 A1 | 4/2007 | Freishlad et al. |
| 2007/0091940 A1 | 4/2007 | Jameson |
| 2007/0097380 A1 | 5/2007 | de Groot et al. |
| 2007/0127036 A1 | 6/2007 | Liao et al. |
| 2007/0139656 A1 | 6/2007 | Wan |
| 2007/0247637 A1 | 10/2007 | de Groot et al. |
| 2008/0018901 A1 | 1/2008 | de Groot |
| 2008/0049233 A1 | 2/2008 | De Groot |
| 2008/0088849 A1 | 4/2008 | de Lega et al. |
| 2008/0174784 A1 | 7/2008 | de Lega et al. |
| 2008/0266574 A1 | 10/2008 | Groot et al. |

FOREIGN PATENT DOCUMENTS

| | | |
|---|---|---|
| DE | 4309056 | 9/1994 |
| EP | 0 397 388 A2 | 11/1990 |
| EP | 0 549 166 A2 | 6/1993 |
| EP | 0 617 255 A1 | 9/1994 |
| EP | 0 929 094 A2 | 7/1999 |
| GB | 2385417 | 8/2003 |
| JP | 8327327 | 12/1996 |
| JP | 09-218016 | 8/1997 |
| JP | 2000121317 | 4/2000 |
| JP | 2000-180124 | 6/2000 |
| JP | 2001-141652 | 5/2001 |
| JP | 2001-272603 | 10/2001 |
| WO | 93/24805 | 12/1993 |
| WO | 95/09343 | 4/1995 |
| WO | WO 97/44633 | 11/1997 |
| WO | WO 02/082008 | 10/2002 |
| WO | WO 03/062802 | 7/2003 |

OTHER PUBLICATIONS

R.M.A. Azzam et al., "Reflection and Transmission of Polarized Light by Stratified Planar Structures", *Ellipsometry and Polarized Light*, Elsevier Science B.V. ISBN 0 444 87016 4 (Paperback) pp. 267-363 (1987).

M. Bashkansky et al., "Signal Processing for Improving Field Cross-correlation Function in Optical Coherence Tomography", *Supplement to Optics & Photonics News*, 9(5) (May 1998).

A. Bosseboeuf et al., "Application of microscopic interferometry techniques in the MEMS field", *Proc. SPIE*, 5145, pp. 1-16 (2003).

M. Davidson et al., "An Application of Interference Microscopy to Integrated Circuit Inspection and Metrology", *Proceedings of SPIE*, vol. 775, pp. 233-247 (1987).

J.E. Greivenkamp, "Generalized data reduction for heterodyne interferometry", *Opt. Eng.*, vol. 23 No. 4, pp. 350-352 (Jul./Aug. 1984).

P de Groot et al., "Signal modeling for low coherence height-scanning interference microscopy", *Applied Optics*, vol. 43 No. 25, pp. 4821-4830 (Sep. 1, 2004).

P. de Groot, "Derivation of algorithms for phase-shifting interferometry using the concept of a data-sampling window", *Appl. Opt.*, 34(22), p. 4723-4730 (1995).

P. de Groot et al., "Signal modeling for modern interference microscopes", *SPIE Proceedings*, 5457-4 (2004).

Peter de Groot et al., "Determination of fringe order in white-light interference microscopy", *Appl. Opt.*, 41(22) pp. 4571-4578 (2002).

Dresel, Thomas et al., "Three-dimensional sensing of rough surfaces by coherence radar", *Applied Optics*, vol. 31, No. 7, pp. 919-925 (Mar. 1, 1992).

Feke, Gilbert D. et al., "Interferometric back focal plane microellipsometry", *Applied Optics*, vol. 37, No. 10, pp. 1796-1802 (Apr. 1, 1998).

P.A. Flournoy et al., "White-light interferometric thickness gauge", *Appl. Opt.*, 11(9), pp. 1907-1915 (1972).

G. Hausler et al., "Coherence Radar and Spectral Radar—New Tools for Dermatological Diagnosis", *Journal of Biomedical Optics*, vol. 3, No. 1, pp. 21-31 (Jan. 1998).

R.D. Holmes et al., "Scanning microellipsometry for extraction of true topograpy", *Electronics Letters*, vol. 31, No. 5, pp. 358-359 (Mar. 2, 1995).

Seung-Woo Kim et al., "Thickness-profile measurement of transparent thin-film layers by white-light scanning interferometry,", *Applied Optics*, vol. 38, No. 28, pp. 5968-5973 (Oct. 1, 1999).

Kieran G. Larkin, "Efficient nonlinear algorithm for envelope detection in white light interferometry", *J. Opt. Soc. Am A4*, pp. 832-843 (1996).

Kino, Gordon S. et al., "Mirau correlation microscope", *Applied Optics*, vol. 29, No. 26, pp. 3775-3783 (Sep. 10, 1990).

Kujawinska, Malgorzata, "Spatial Phase Measurement Methods", *Interferogram Analysis: Digital Fringe Pattern Measurement Techniques*, IOP Publishing Ltd., 1993, pp. 141-193.

Lee et al., "Profilometry with a coherence scanning microscope", *Appl. Opt.*, 29(26), pp. 3784-3788 (1990).

I. Lee-Bennett, "Advances in non-contacting surface metrology", *OF&T Workshop*, paper OTuC1 (2004).

K. Leonhardt et al., "Micro-Ellipso-Height-Profilometry", *Optics Communications*, vol. 80, No. 3, 4, pp. 205-209 (Jan. 1, 1991).

Y. Liu et al., "Common path interferometric rnicroellipsometry", *SPIE*, vol. 2782, pp. 635-645 (1996).

Lyakin et al., "The interferometric system with resolution better than coherence length for determination of geometrical thickness and refractive index of a layer object", *Proceedings of the SPIE—The International Society for Optical Engineering SPIE-INT. Soc. Opt. Eng USA*, vol. 4956, pp. 163-169 (Jul. 2003).

C.J. Morgan, "Least-Squares estimation in phase-measurement interferometry", *Apt. Let.*, 7(8), pp. 368-370 (1982).

Ngoi et al., "Phase-shifting interferometry immune to vibration", *Applied Optics*, vol. 40, No, 19, pp. 3211-3214 (2001).

A.V. Oppenheim et al., "10.3: The time-dependent Fourier Transform", *Discrete-Time Signal Processing*, 2nd Edition, pp. 714-722 (Prentice Hall, New Jersey, 1999).

M.C. Park et al., "Direct quadratic polynomial fitting for fringe peak detection of white light scanning interferograms", *Opt. Eng*, 39(4), pp. 952-959 (2000).

Pelligrand, S. et al., "Mesures 3D de topographies et de vibrations a l'echelle (sub)micrometrique par microscopie optique interferometrique", *Proc. Club CMOI, Methods et Techniques Optiques pour l'Industrie* (2002).

Pluta, Maksymilian, "Advanced Light Microscopy", vol. 3, (Elsevier, Amsterdam, 1993) pp. 265-271.

W.H. Press et al., "Linear Correlation", *Numerical Recipes in C*, Cambridge University Press, 2nd Edition, pp. 636-639 (1992).

Rosencwaig, Allan et al., "Beam profile reflectometry: A new technique for dielectric film measurements", *Applied Physics Letters*, vol. 60, No. 11, pp. 1301-1303 (Mar. 16, 1992).

Sandoz, Patrick "Wavelet transform as a processing tool in white-light interferometry", *Optics Letters*, vol. 22, No. 14, pp. 1065-1067 (Jul. 15, 1997).

P. Sandoz et al., "Optical implementation of frequency domain analysis for white light interferometry", *Proceedings SPIE*, vol. 2545, pp. 221-228 (Jun. 1995).

P. Sandoz et al., "High-resolution profilometry by using phase calculation algorithms for spectroscopic analysis of white-light interferograms", *Journal of Modern Optics*, vol. 43, No. 4, pp. 701-708 (1996).

P. Sandoz et al., "Processing of white light correlograms: simultaneous phase and envelope measurements by wavelet transformation", *SPIE*, 3098, pp. 73-82 (1997).

U. Schnell et al., "Dispersive white-light interferometry for absolute distance measurement with dielectric multilayer systems on the target", *Optics Letters*, vol. 21, No. 7, pp. 528-530 (Apr. 1996).

J. Schwider et al., "Dispersive interferometric profilometer", *Optics Letters*, vol. 19, No. 13, pp. 995-997 (Jul. 1994).

C.W. See et al., "Scanning optical microellipsometer for pure surface profiling", *Applied Optics*, vol. 35, No. 34, pp. 6663-6668 (Dec. 1, 1996).

Shatalin, S.V. et al., "Reflection conoscopy and micro-ellipsometry of isotropic thin film structures", *Journal of Microscopy*, vol. 179, Part 3, pp. 241-252 (Sep. 1995).

M. Totzeck, "Numerical simulation of high-NA quantitative polarization microscopy and corresponding near-fields", *Optik*, vol. 112, No. 9, pp. 399-406 (2001).

R. Tripathi et al., "Spectral shaping for non-Gaussian source spectra in optical coherence tomography", *Optics Letters*, vol. 27, No. 6, pp. 406-408 (2002).

D. Willenborg et al, "A novel micro-spot dielectric film thickness measurement system", *SPIE*, vol. 1594, pp. 322-333 (1991).

Abdulhalim, "Spectroscopic interference microscopy technique for measurement of layer parameters", Meas. Sci. Technol., vol. 12, pp. 1996-2001 (2001). cited by other.

Biegen, "Determination of the Phase Change on Reflection from Two-beam Interference," Optics Letters, 19:21:1690-1692, Nov. 1, 1994.

Chim, S. S. C. and Kino, G. S., "Three-Dimensional Image Realization in Interference Microscopy", Applied Optics, May 10, 1992, vol. 31, No. 14.

Creath, K. "Step height measurement using two-wavelength phase-shifting interferometry", Applied Optics, vol. 26, No. 14, pp. 2810-2816 (Jul. 15, 1987).

Danielson et al., "Absolute Optical Ranging Using Low Coherence Interferometry," Applied Optics, 30:21:2975-2979, Jul. 20, 1991.

de Groot et al., "Angle-resolved three-dimensional analysis of surface films by coherence scanning interferometry", Optics Letters, vol. 32, No. 12, pp. 1638-1640 (Jun. 15, 2007). cited by other.

de Groot et al., "Signal modeling for modern interference microscopes", SPIE Proceedings vol. 5457, pp. 26-34 (2004). cited by other.

de Groot et al.; "Three-dimensional imaging by sub-Nyquist sampling of white-light interfergrams"; Optics Letters vol. 18, No. 17; pp. 1462-1464, Sep. 1, 1993.

de Groot, "Extending the unambiguous range of two-color interferometers", Applied Optics, vol. 33, No. 25, pp. 5948-5953 (Sep. 1, 1994).

de Groot, "Three-color laser-diode interferometer", Applied Optics, vol. 30, No. 25, pp. 3612-3616 (Sep. 1, 1991).

de Groot, P., "Phase-shift calibration errors in interometers with spherical Fizeua cavities," Applied Optics, vol. 34:16, pp. 2856-2863 (Jun. 1, 1995).

de Lega, X., et al., "Optical topography measurement of patterned wafers," American Institute of Physics Conference Proceedings, vol. 788, pp. 432-436 (2005).

Deck et al., "Two-color light-emitting-diode source for high-precision phase-shifting interferometry", Optics Letters, vol. 18, No. 22, pp. 1899-1901 (Nov. 15, 1993).

Feke et al., Interferometric Back Focal Plane Microellipsometry, Applied Optics/ vol. 33, No. 101 Apr. 1, 1998 p. 1746. cited by other.

Flournoy, P. A., McClure, R. W. And Wyntjes, G. "White-Light Interferometric Thickness Gauge", Applied Optics, Sep. 1972, vol. 11, No. 9.

Gale et al., "Linnik microscope imaging of integrated circuit structures", Applied Optics vol. 35, No. 1, pp. 131-148 (Jan. 1, 1996). cited by other.

Ghiglia et al., "Quality-Guided Path Following", Two-Dimensional Phase Unwrapping—Theory, Algorithms and Software, John Wiley & Sons publishers, ISBN 0-471-24935-1, pp. 122-136 (1998). cited by other.

Hecht, "Basics of Coherence Theory," Optics, 2nd Ed., Addison Wesley, pp. 516-517 (1987).

Kim, Seung-Woo et al., "Thickness-profile measurement of transparent thin-film layers by white-light scanning interferometry", Applied Optics, vol. 38, No. 28, pp. 5968-5973 (Oct. 1, 1999). cited by other.

Kohlhaas, A. Fromchen, C. and Brinkmeyer, E., "High-Resolution OCDR for Testing Integrated-Optical Waveguides: Dispersion-Corrupted Experimental Data Corrected by a Numerical Algorithm", Journal of Lightwave Technology, Nov. 1991, vol. 9, No. 11.

Kujawinska, Malgorzata, "Spatial Phase Measurement Methods", Interferogram Analysis: Digital Fringe Pattern Measurement Techniques, IOP Publishing Ltd. 1993, pp. 141-193. cited by other.

Larkin, "Efficient Nonlinear Algorithm for Envelope Detection in White Light Interferometry," J.Opt. Soc. Am. A, 13:4:832-943 (1996).

Novak et al., "Template-based software for accurate MEMS characterization", Proceedings of SPIE, Fol. 4980, pp. 75-80 (2003). cited by other.

Onodera et al., "Two-wavelength interferometry that uses a Fourier-transform method", Applied Optics, vol. 37, No. 34, pp. 7988-7994 (Dec. 1, 1998).

Park et al., "Direct Quadratic Polynomial Fitting for Fringe Peak Detection of White Light Scanning Interferograms," Opt. Eng., 39:4:952-959, Apr. 2000.

Pfortner et al., "Red-green-blue interferometer for the metrology of discontinuous structures", Applied Optics, vol. 42, No. 4, pp. 667-673 (Feb. 1, 2003).

Schmit, J. et al., "Extended averaging technique for derivation of error-compensating algorithms in phase-shifting interferometry," Applied Optics, vol. 34:19, pp. 3610-3619 (Jul. 1, 1995).

See et al, Scanning optical microellipsometer for pure surface profiling, Applied Optics, Dec. 1996, pp. 6663-6668. cited by examiner.

Sheppard et al., "Effect of numerical aperture on interference fringe spacing", Applied Optics, vol. 34, No. 22, pp. 4731-4734 (Aug. 1, 1995). cited by other.

Tzannes et al., "Measurement of the modulation transfer function of infrared cameras," Optical Engineering, vol. 34, No. 6, pp. 1808-1817 (Jun. 1995). cited by other.

Willenborg et al, "A novel micro-spot dielectric film thickness measurement system", SPIE, vol. 1594, pp. 322-333 (1991). cited by other.

Wyant, "Phase shifting interferometry" (1998).

Youngquist, R. C. Carr, S. and Davies, D. E. N., "Optical Coherence-Domain Reflectometry: a New Optical Evaluation Technique", Optical Letters, Mar. 1987, vol. 12, No. 3.

R.M.A. Azzam et al, "Ellipsometric function of a film-substrate system: Applications to the design of reflection-type optical devices and to ellipsometry", *Journal of the Optical Society of America*, vol. 5, No. 3, pp. 252-260 (1975).

Berman et al., "Review of In Situ & In-line Detection for CMP Applications", Semiconductor Fabtech—8th Edition, pp. 267-274 (1998).

\* cited by examiner

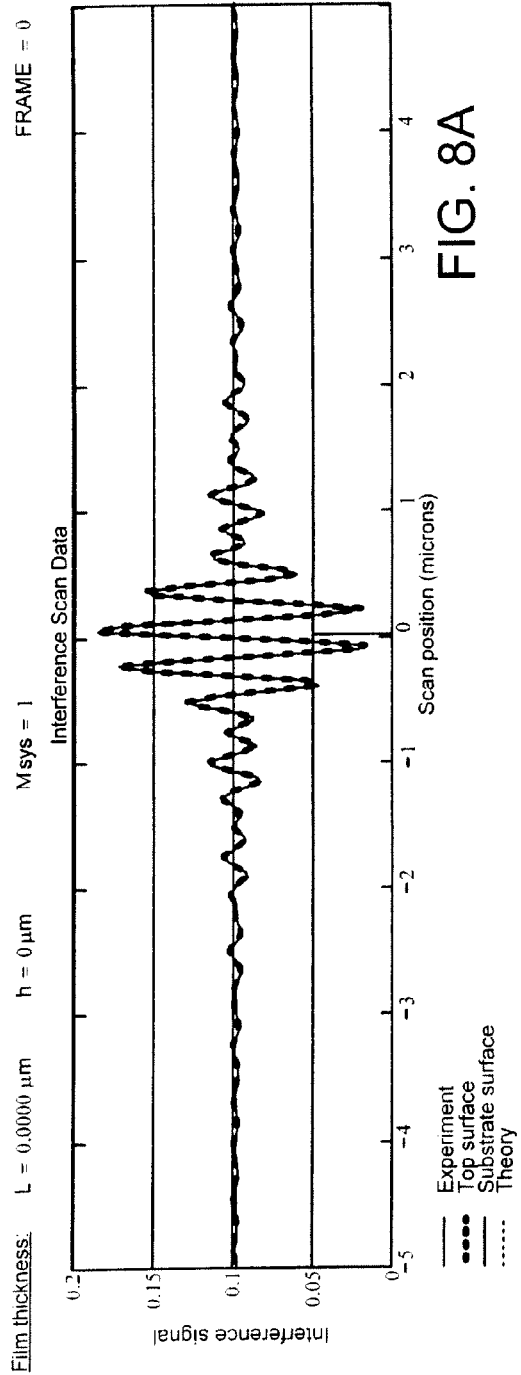
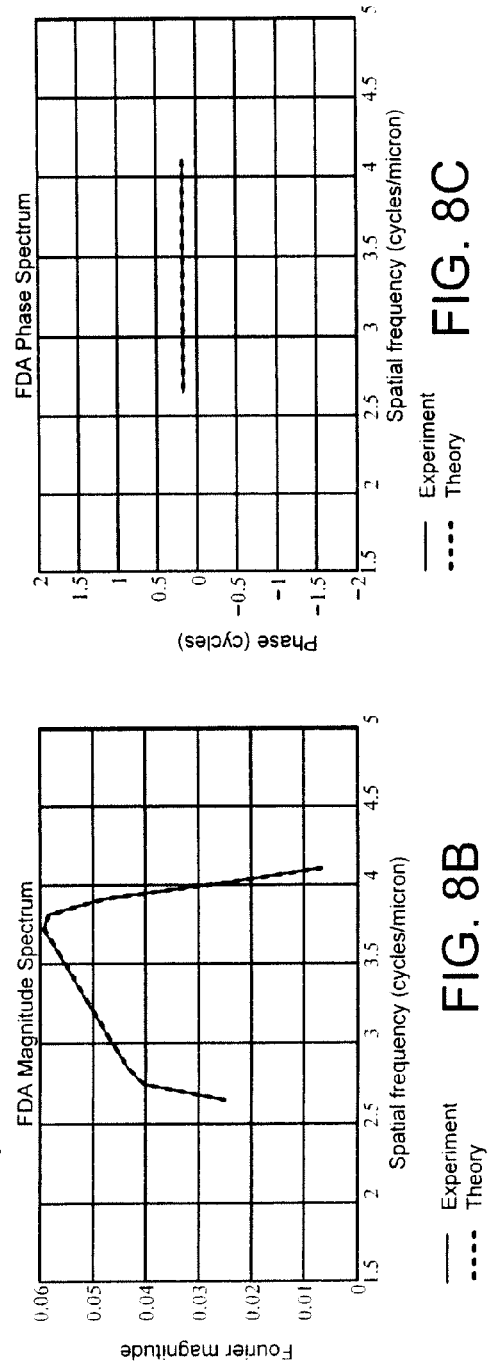
FIG. 8A
FIG. 8B
FIG. 8C

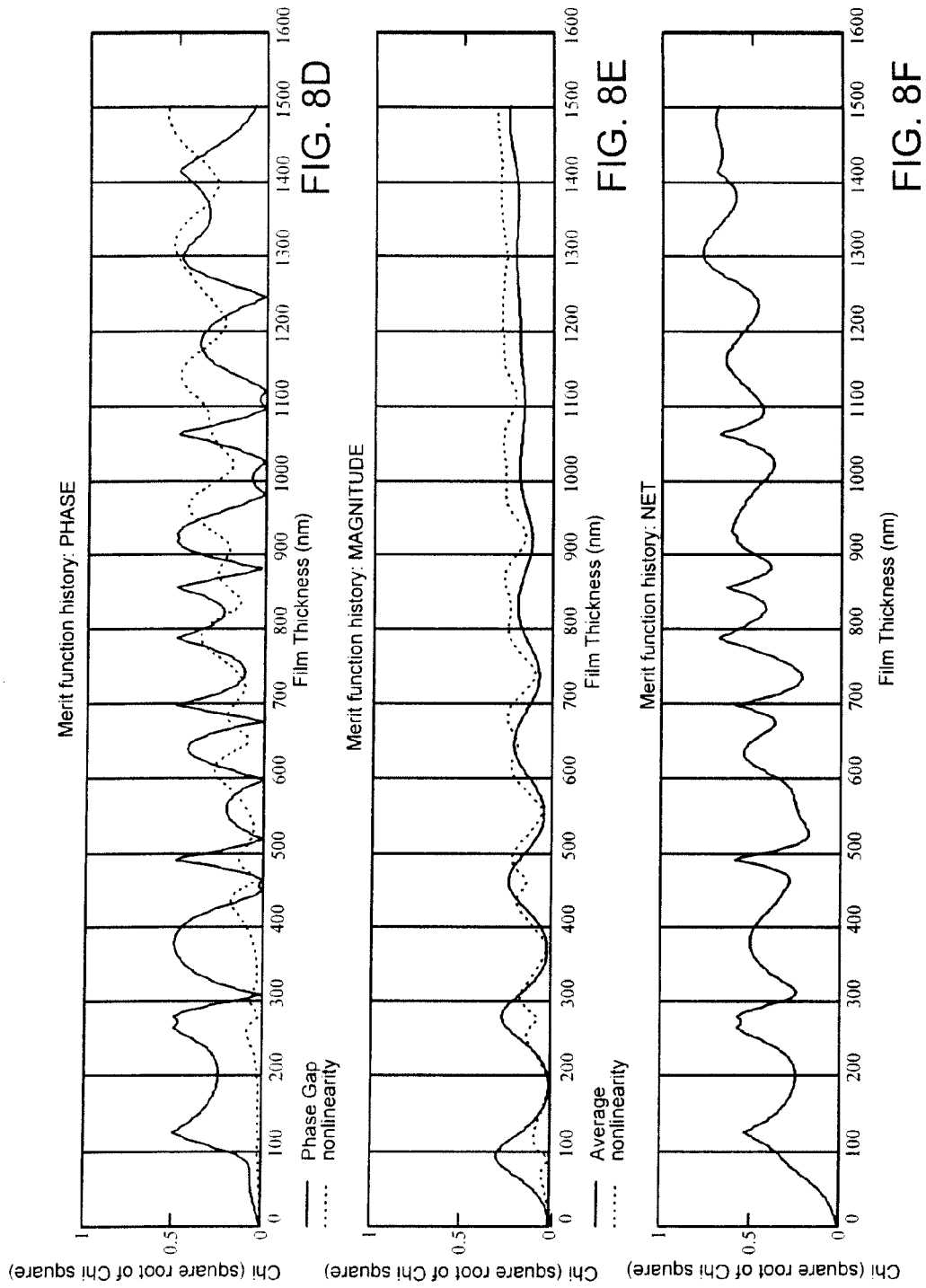

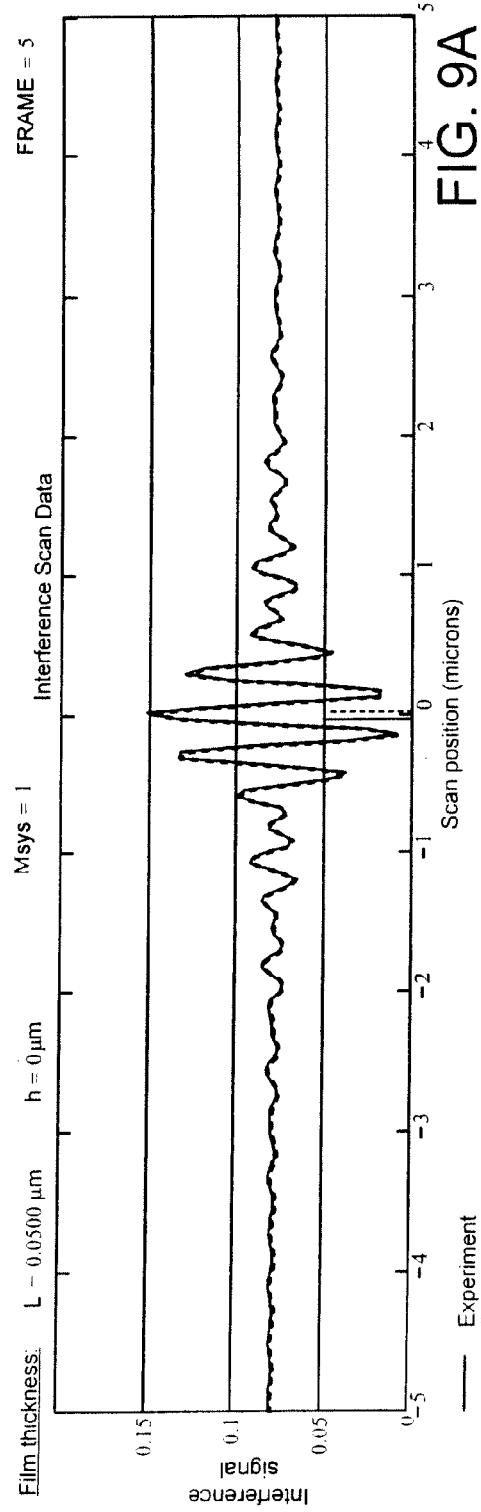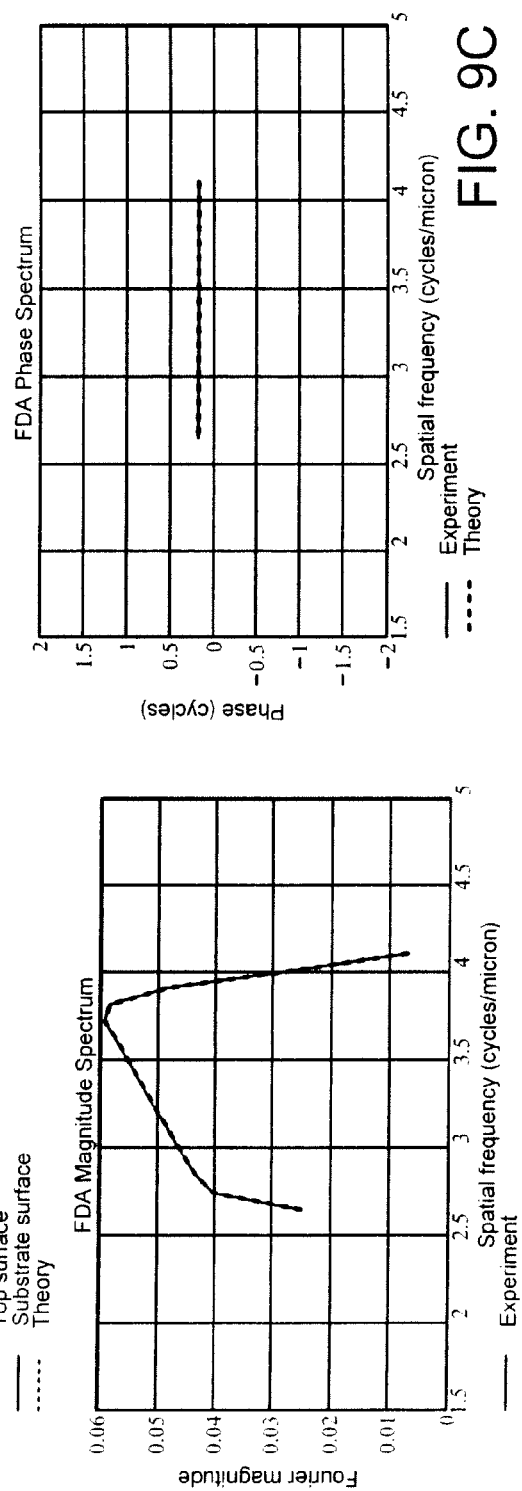

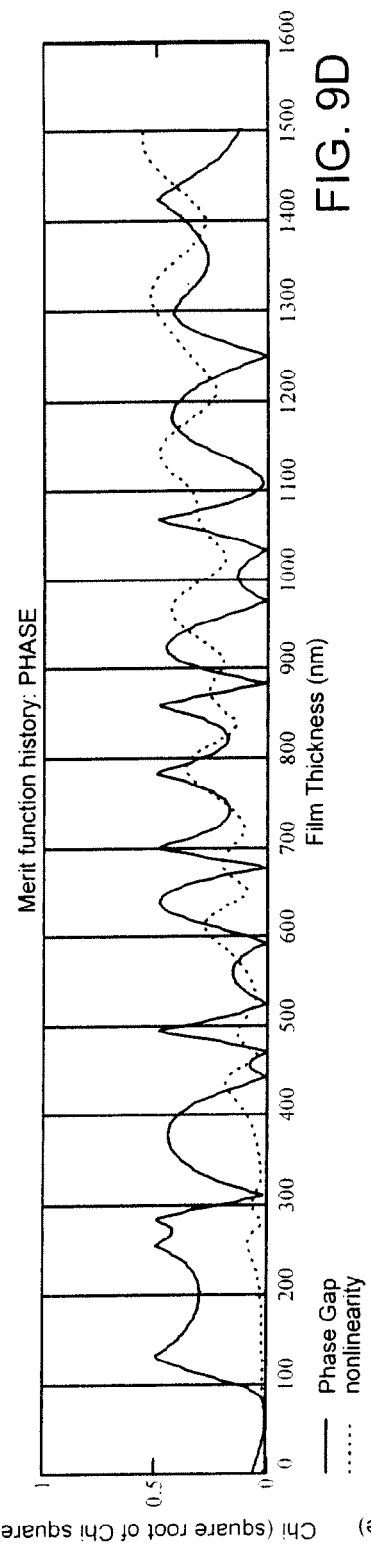
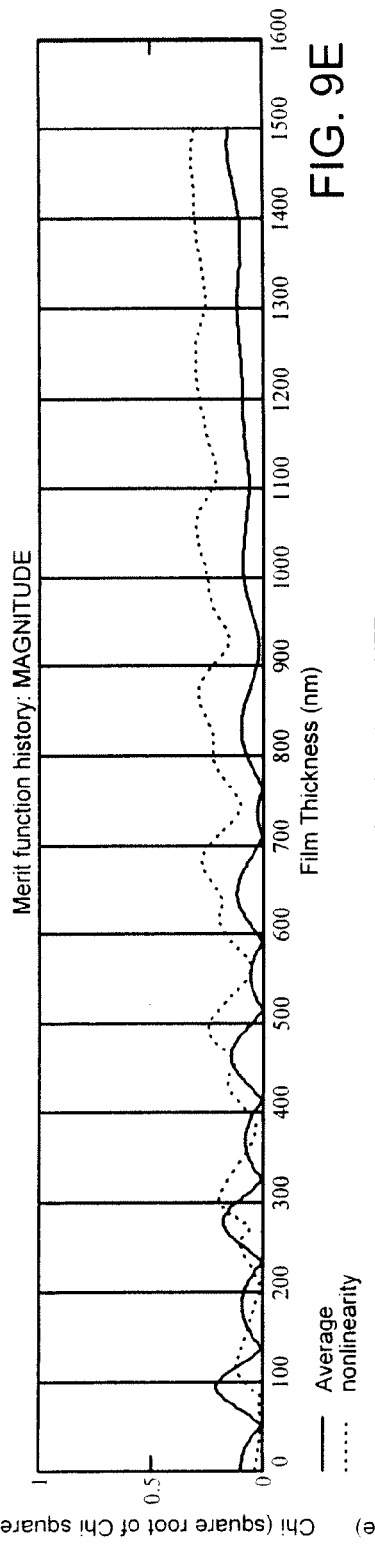
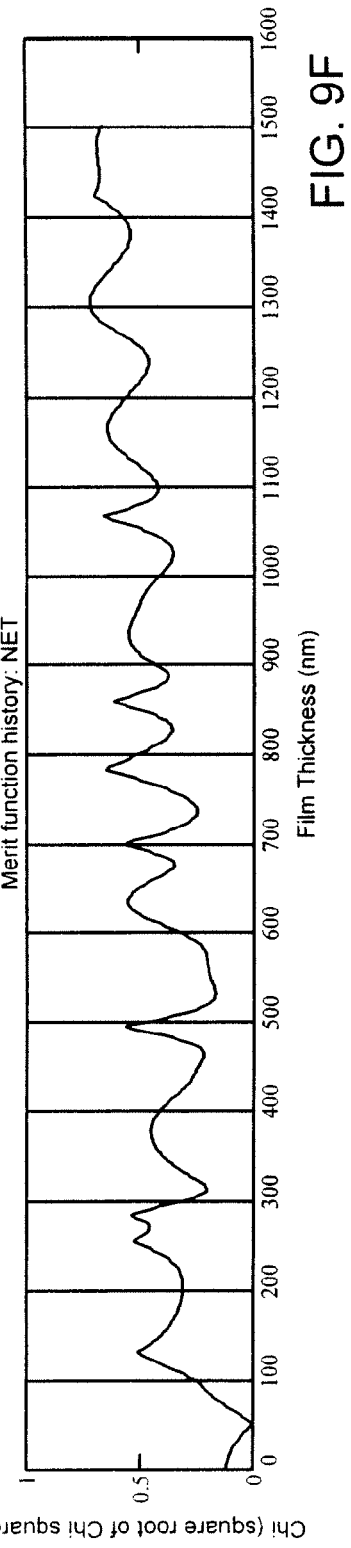
FIG. 9D
FIG. 9E
FIG. 9F

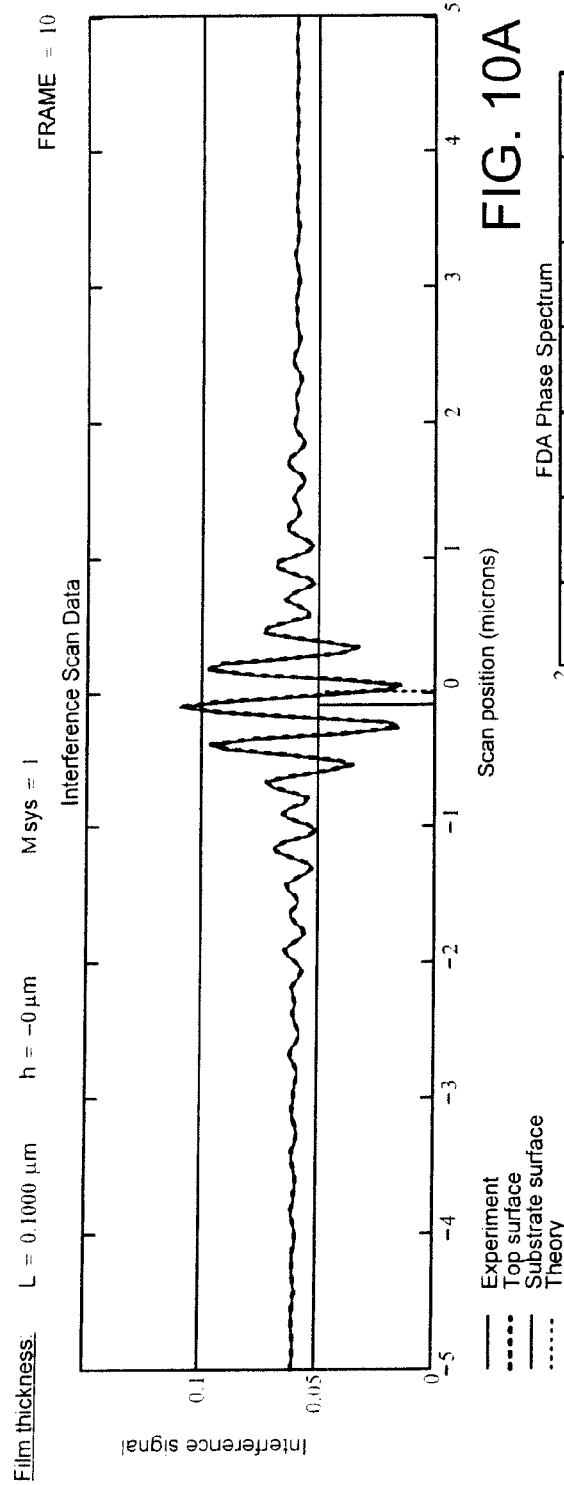
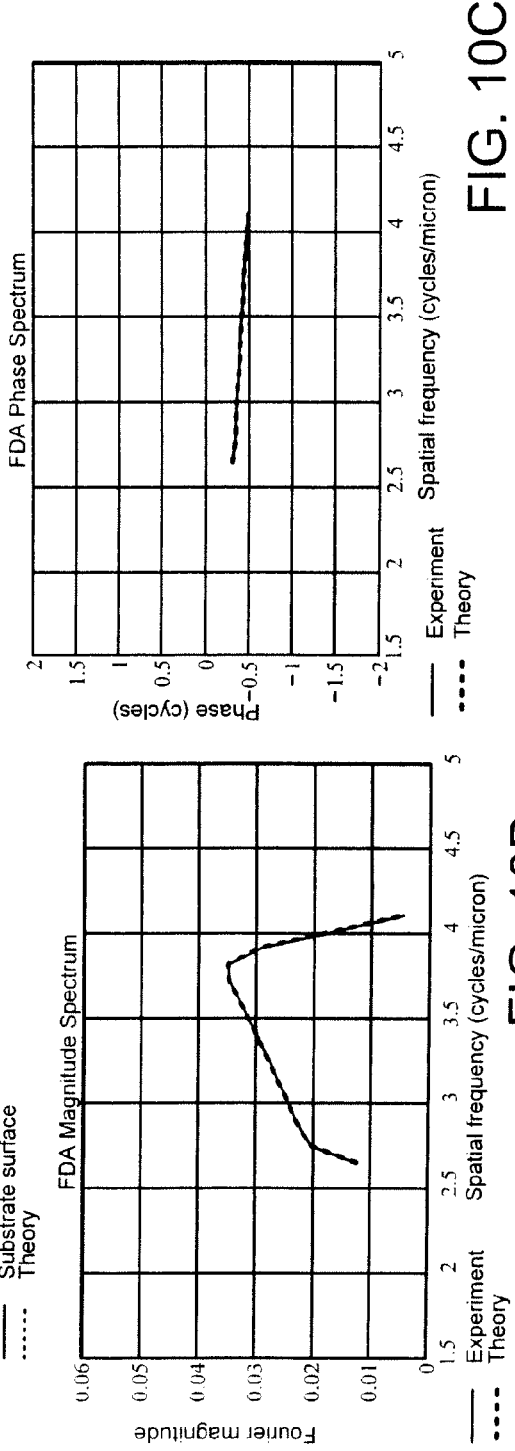
FIG. 10A
FIG. 10B
FIG. 10C

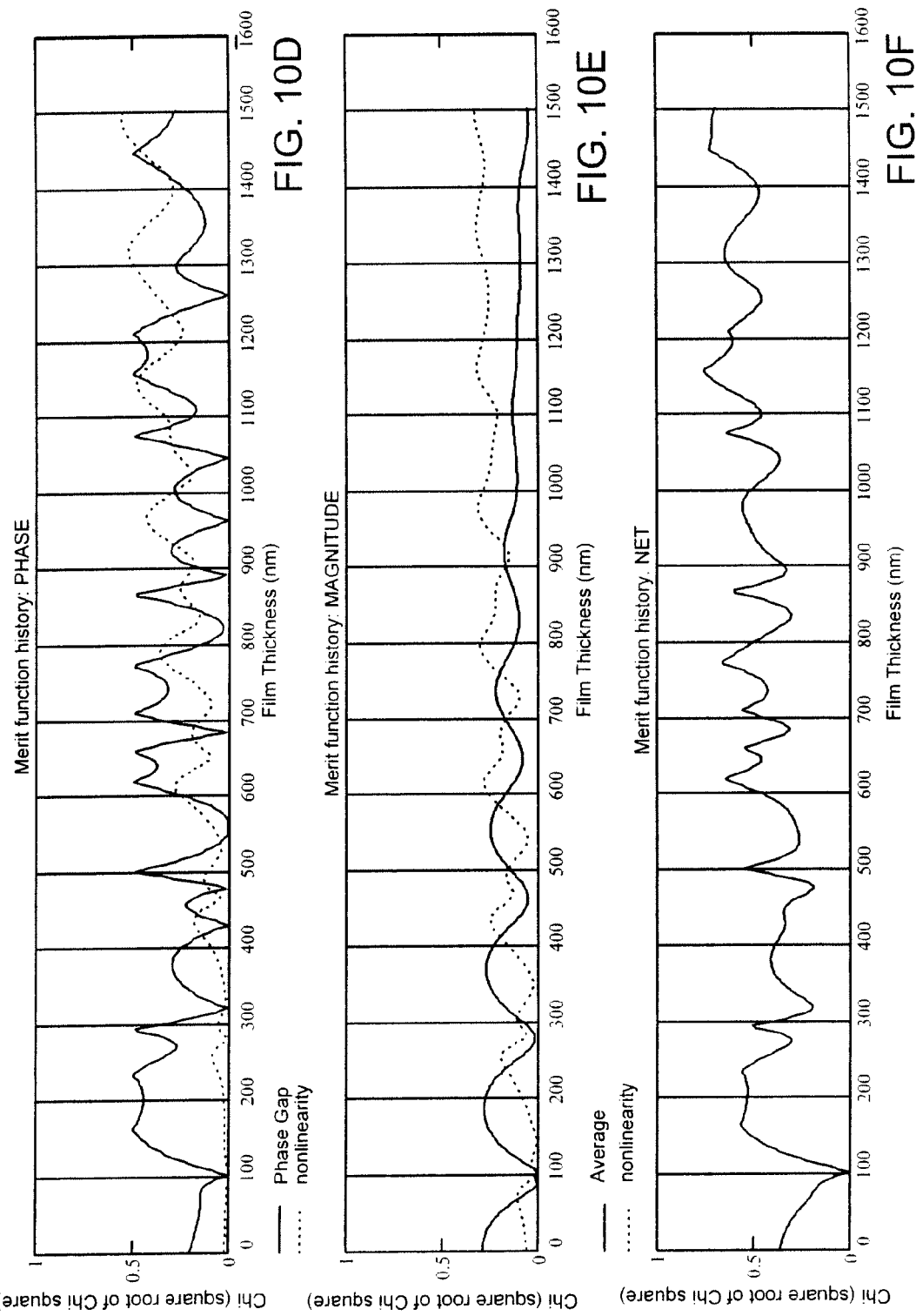

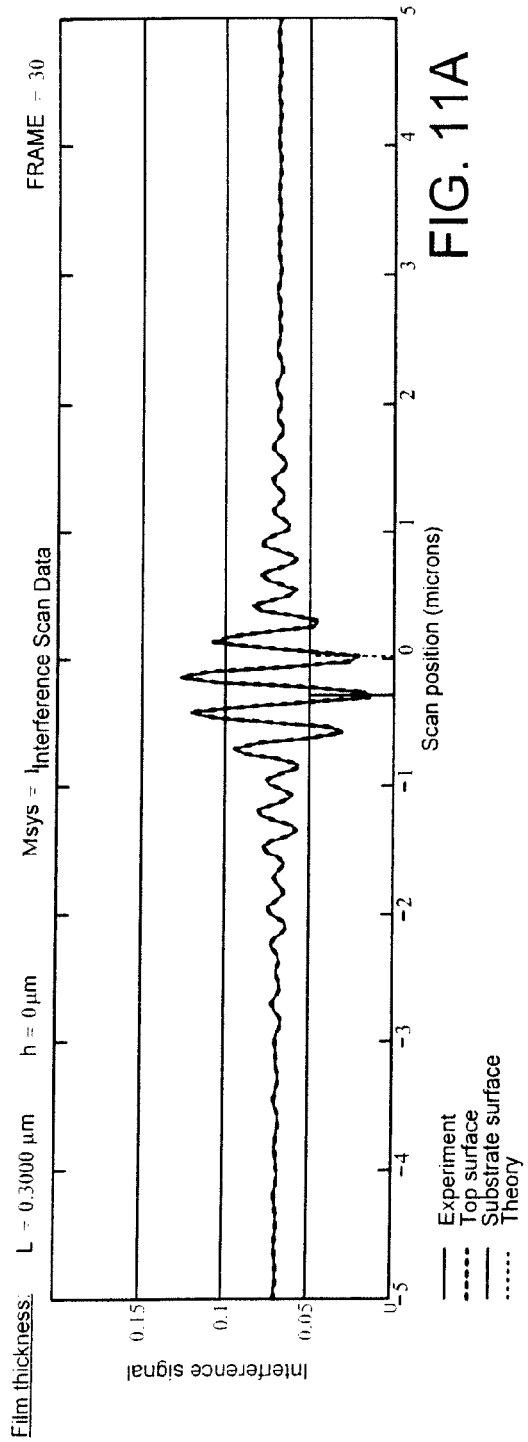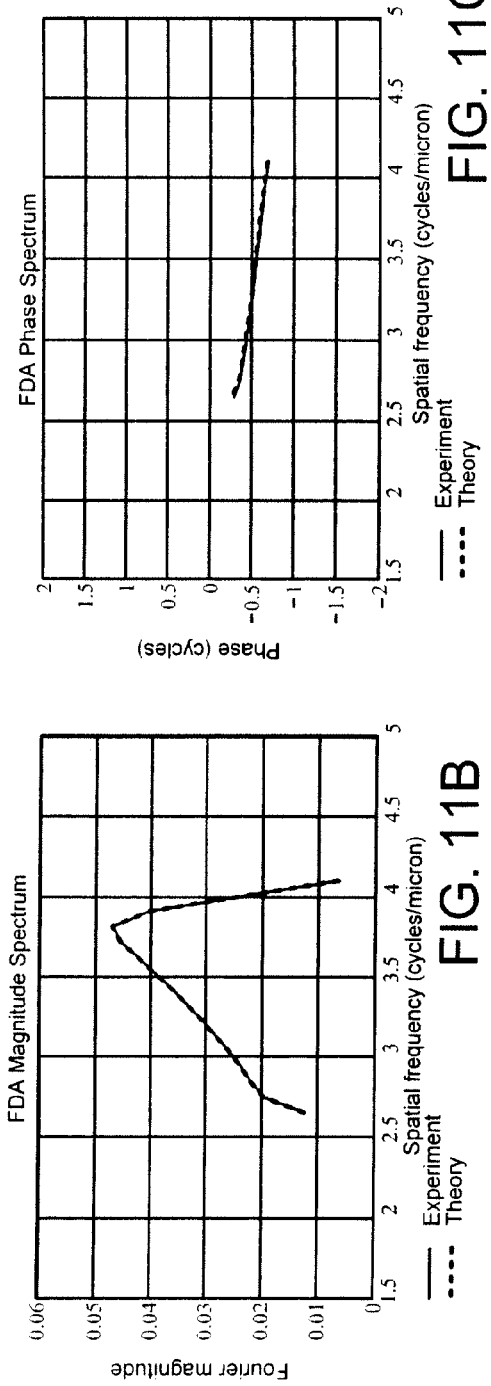

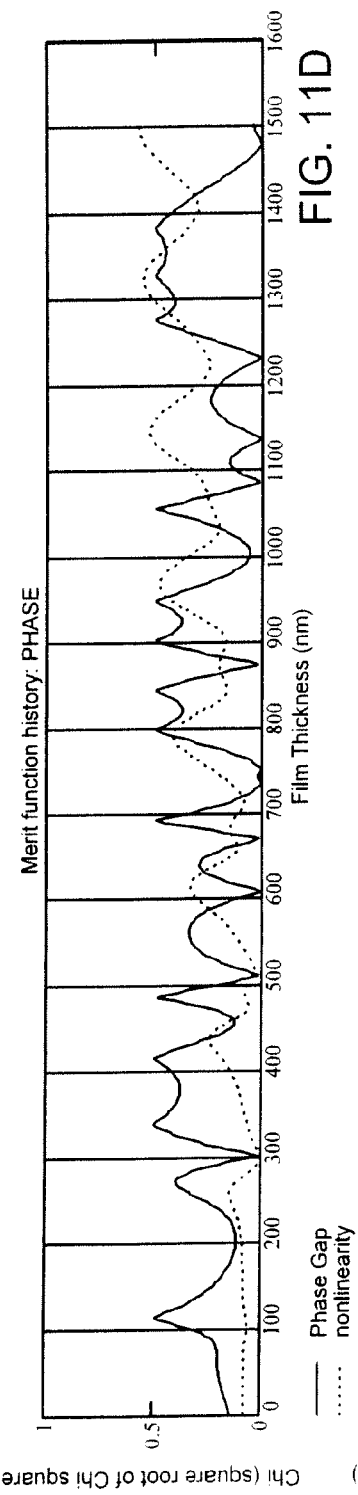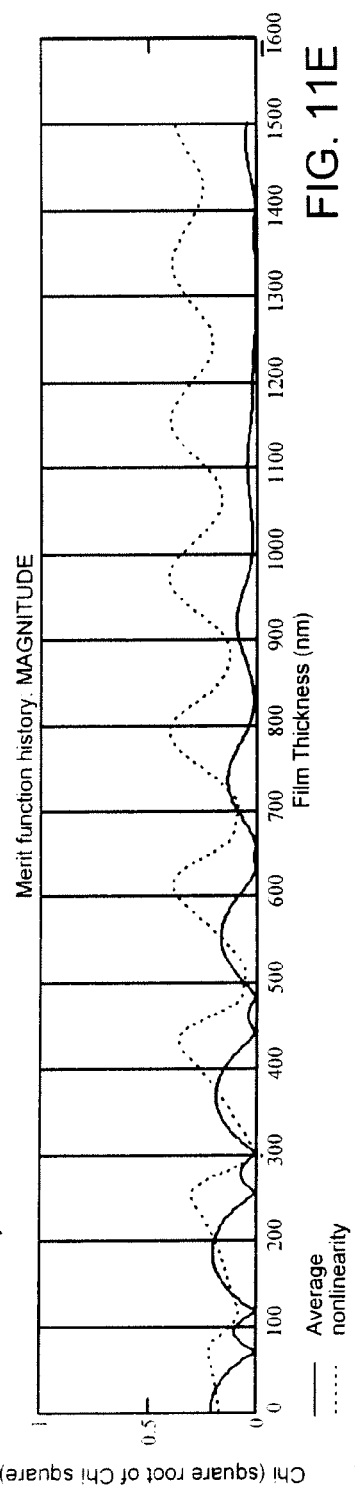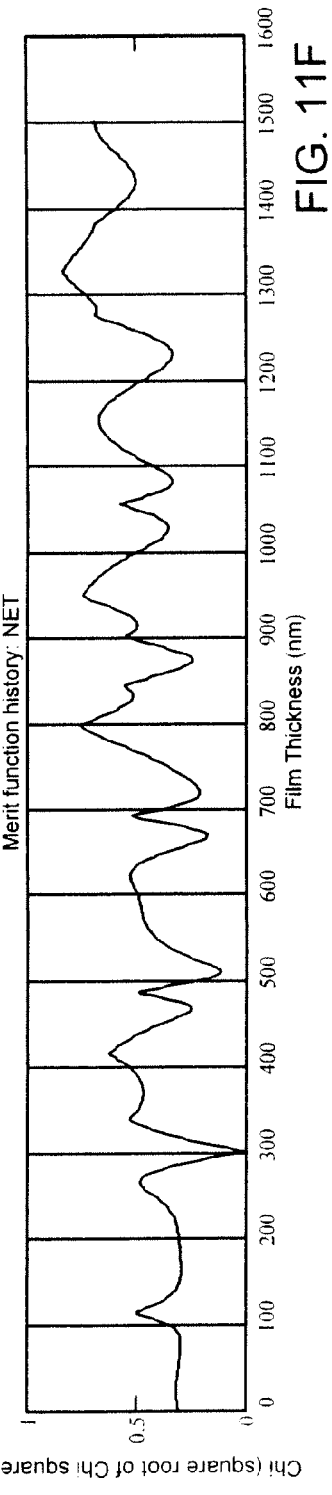

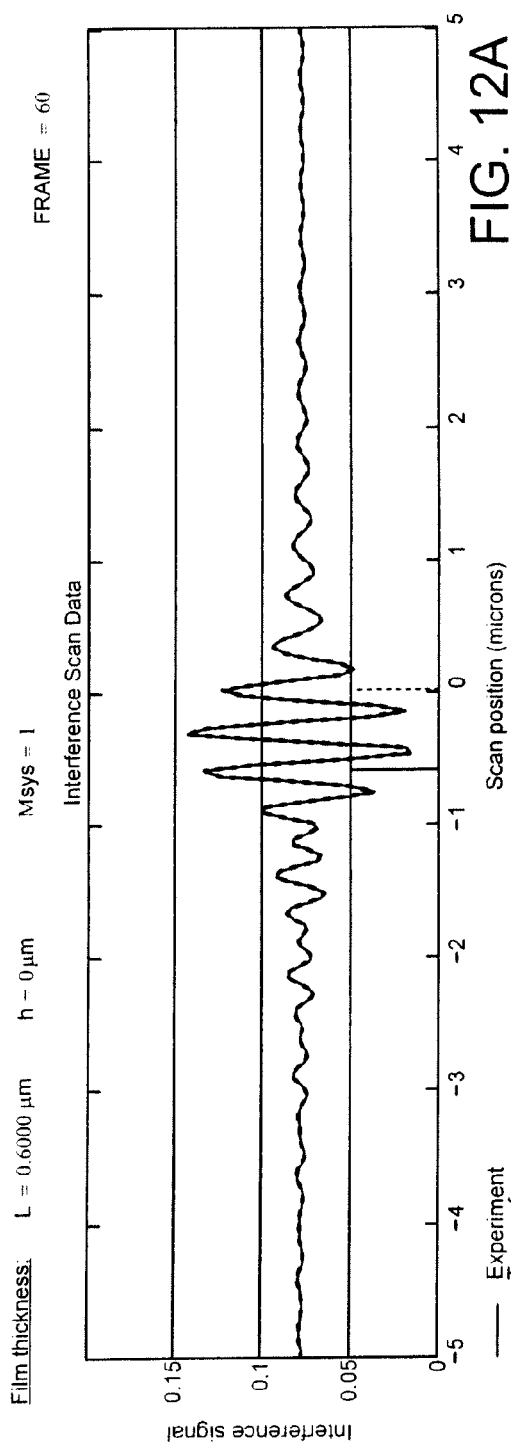
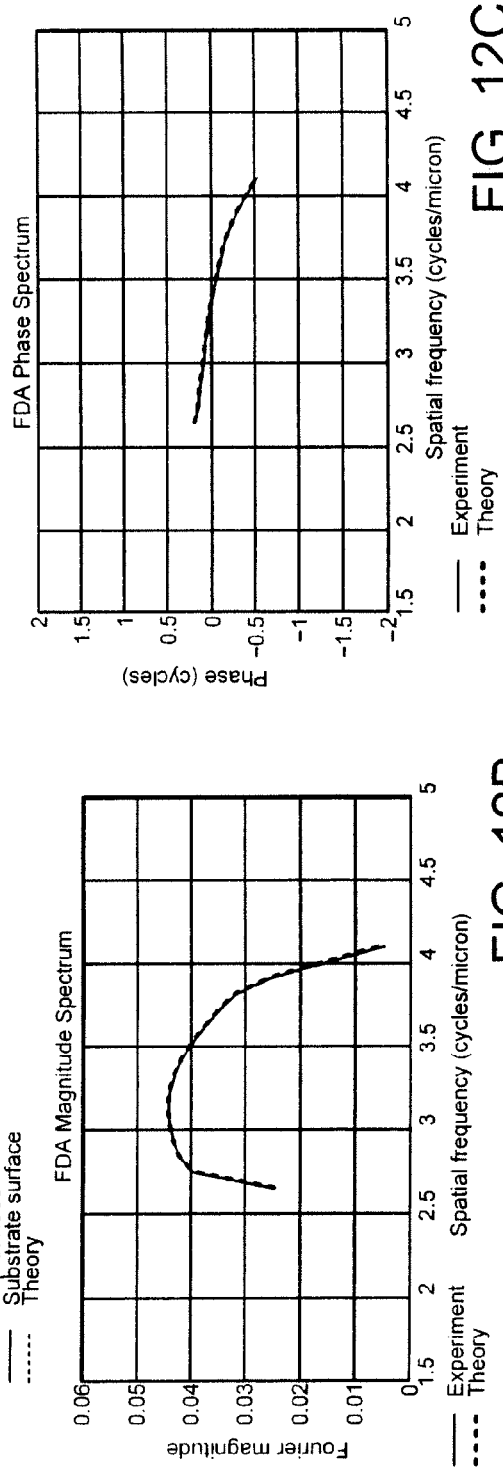
FIG. 12A
FIG. 12B
FIG. 12C

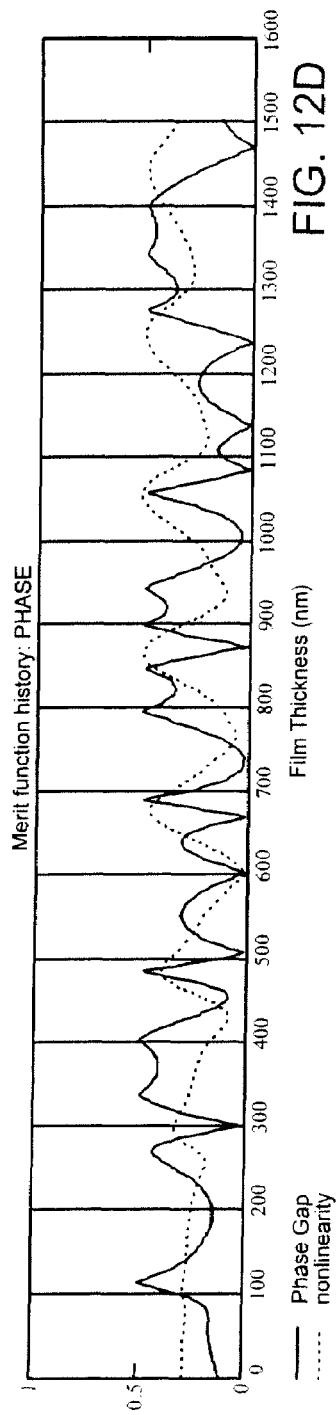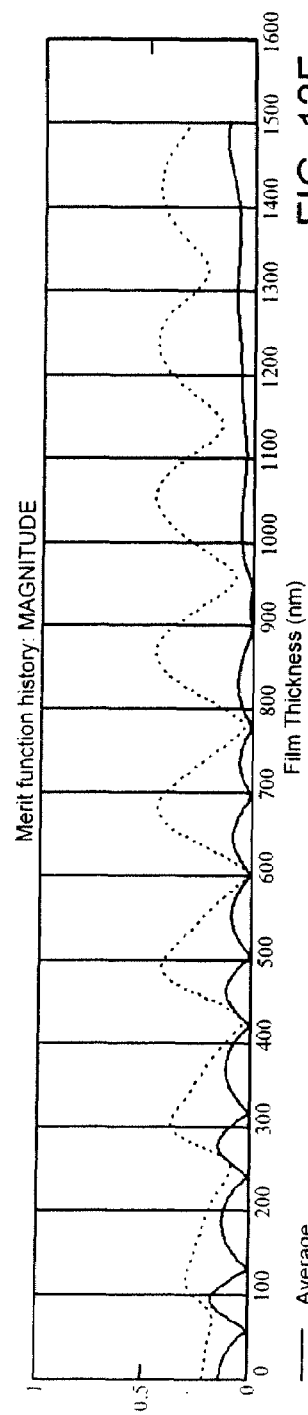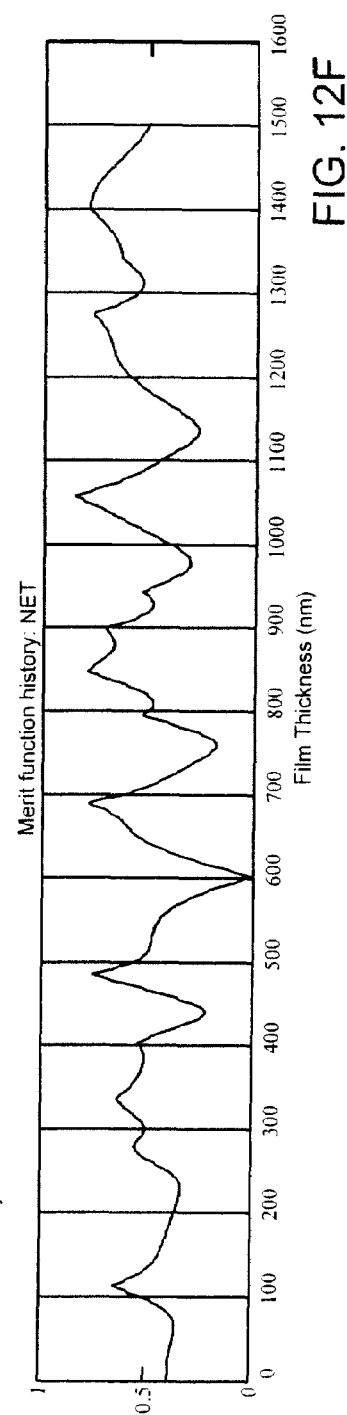

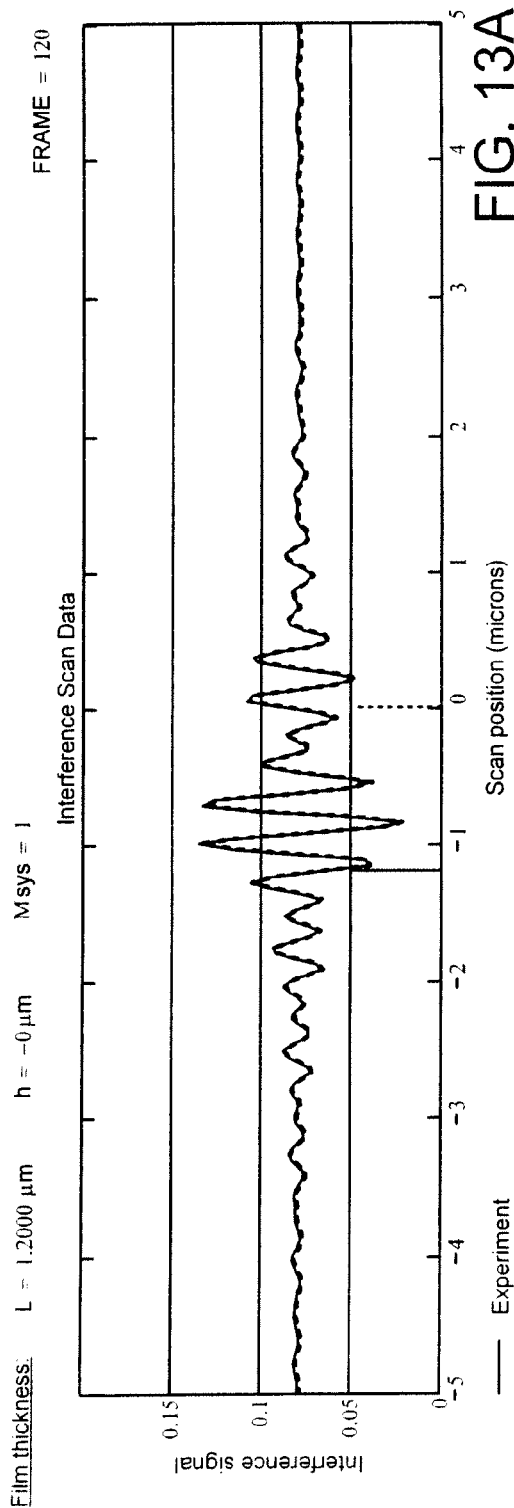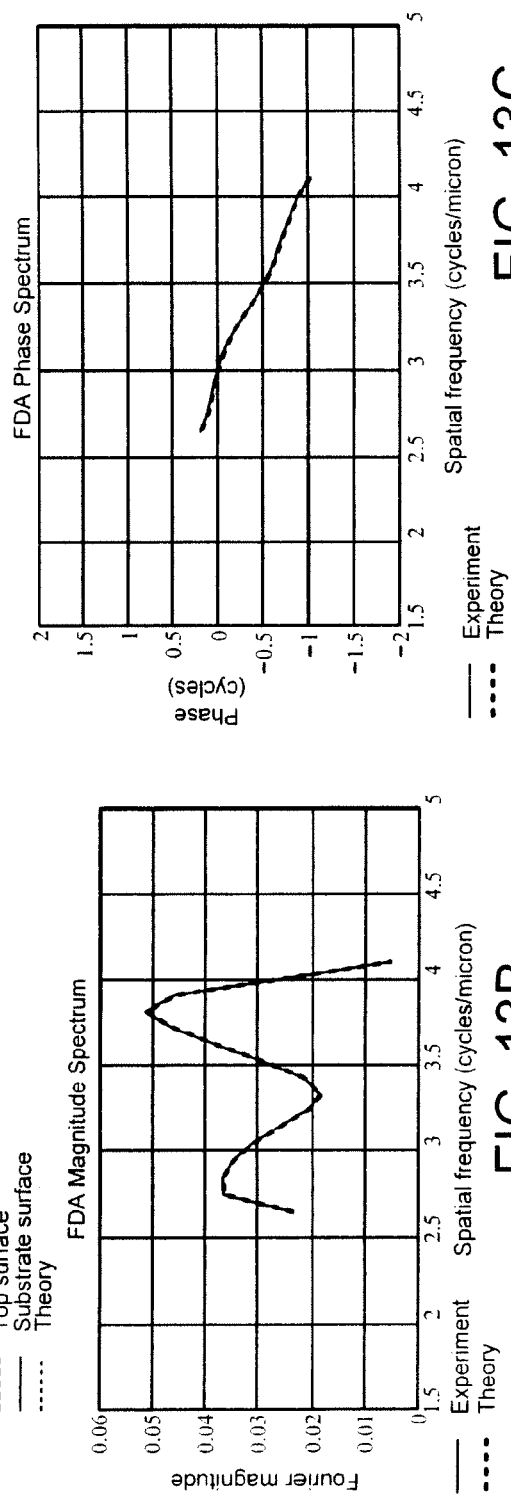
FIG. 13A
FIG. 13B
FIG. 13C

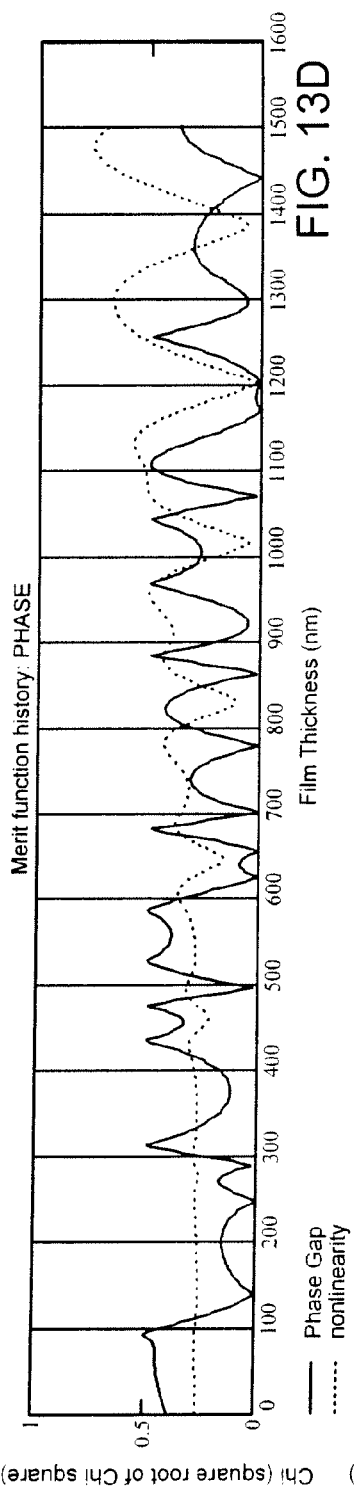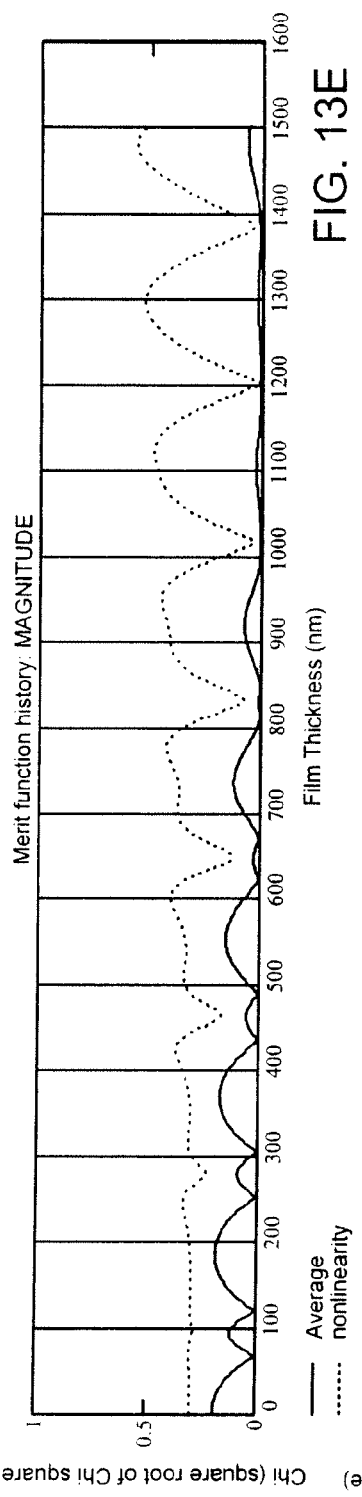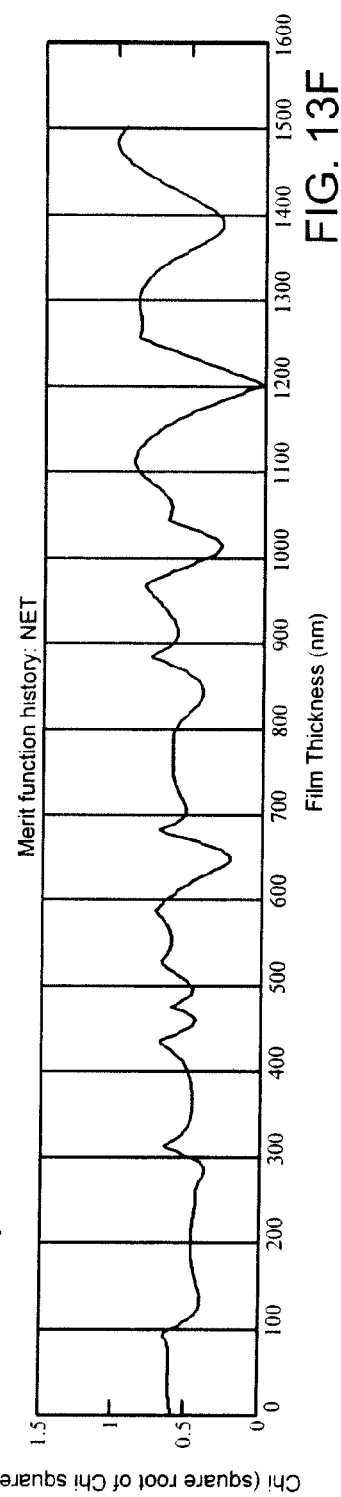

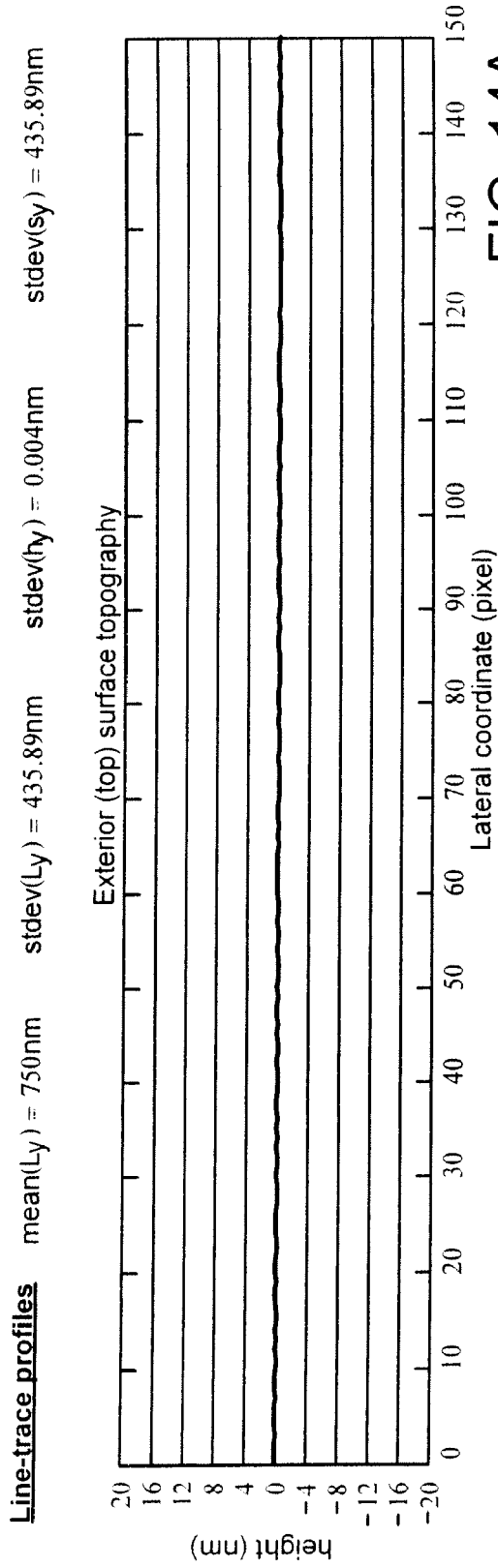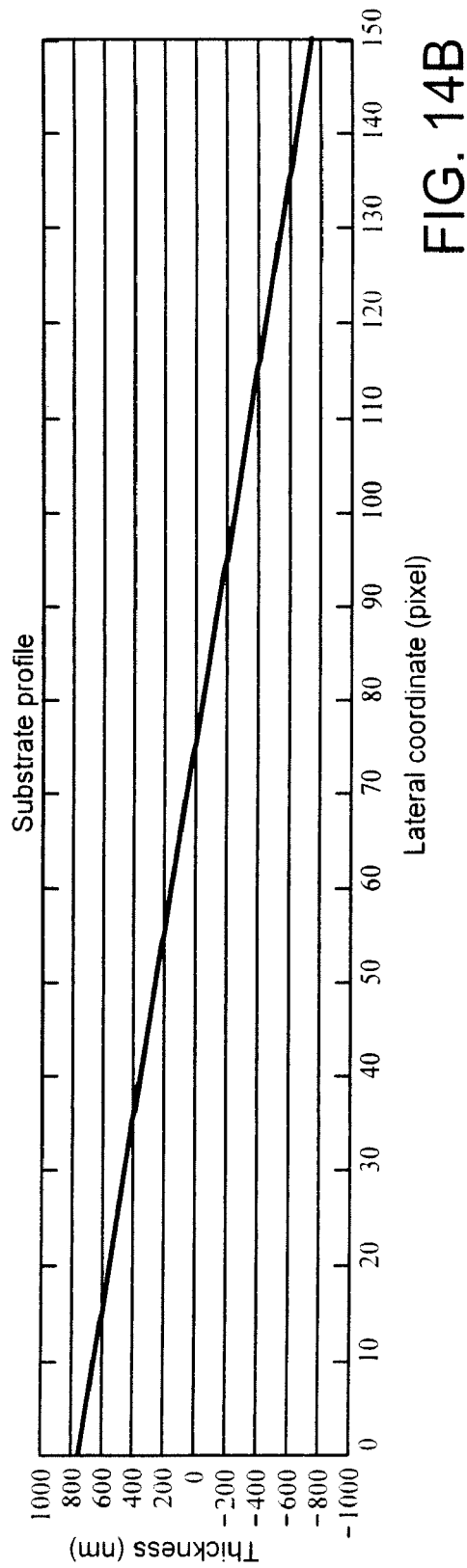

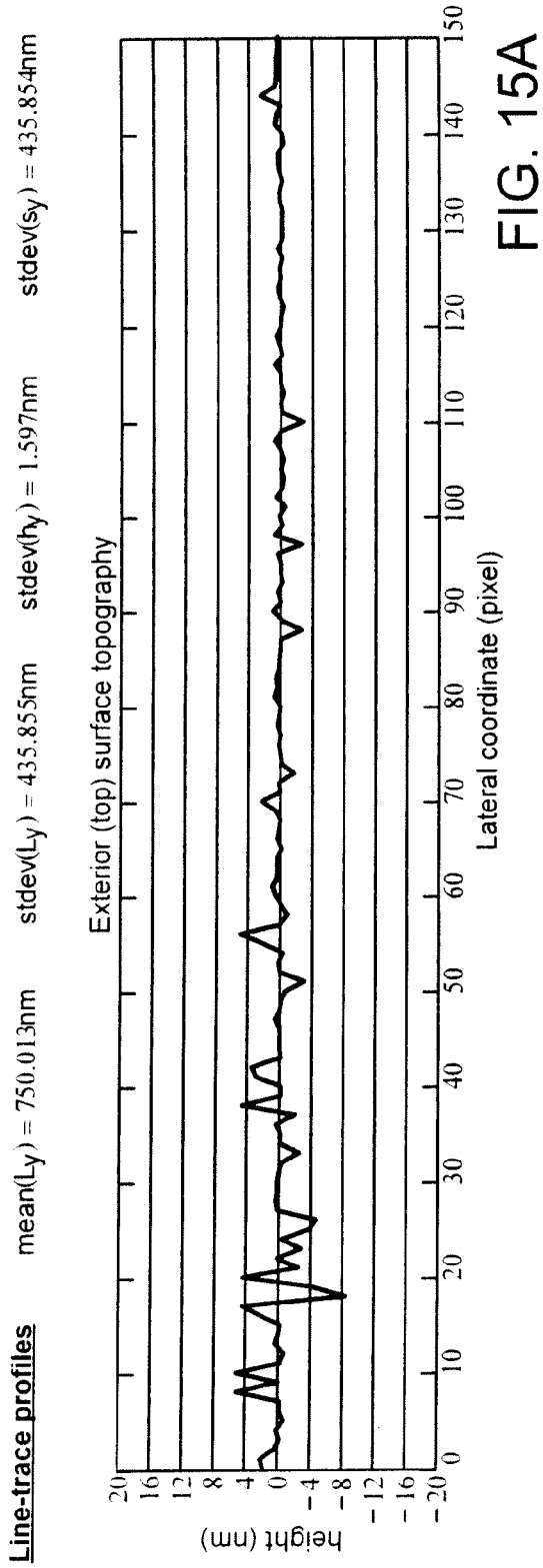
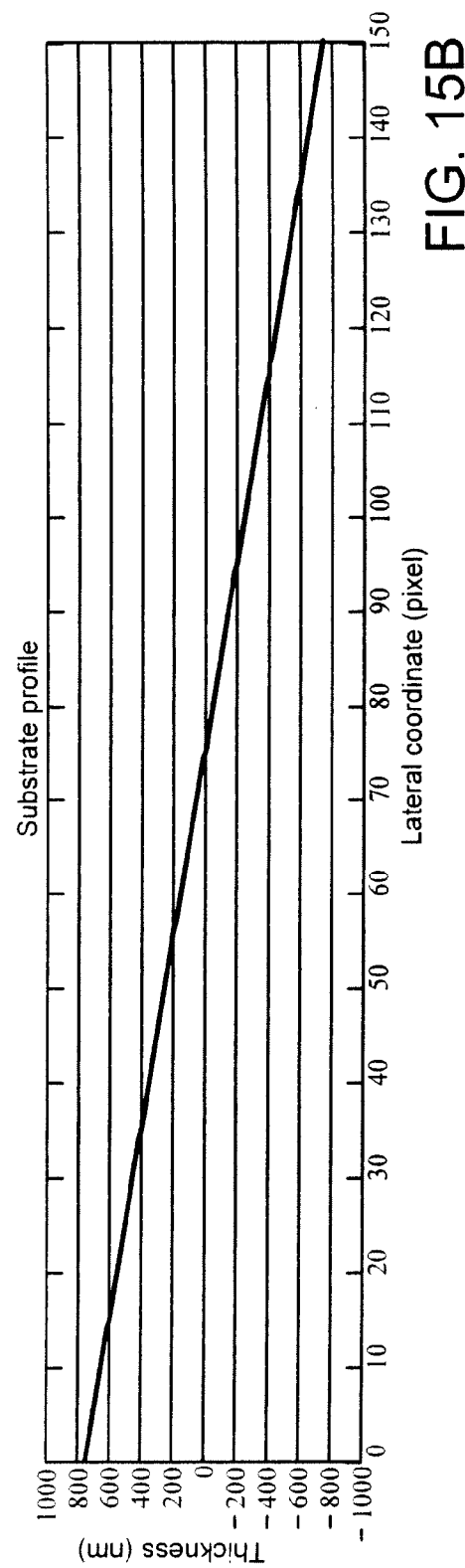

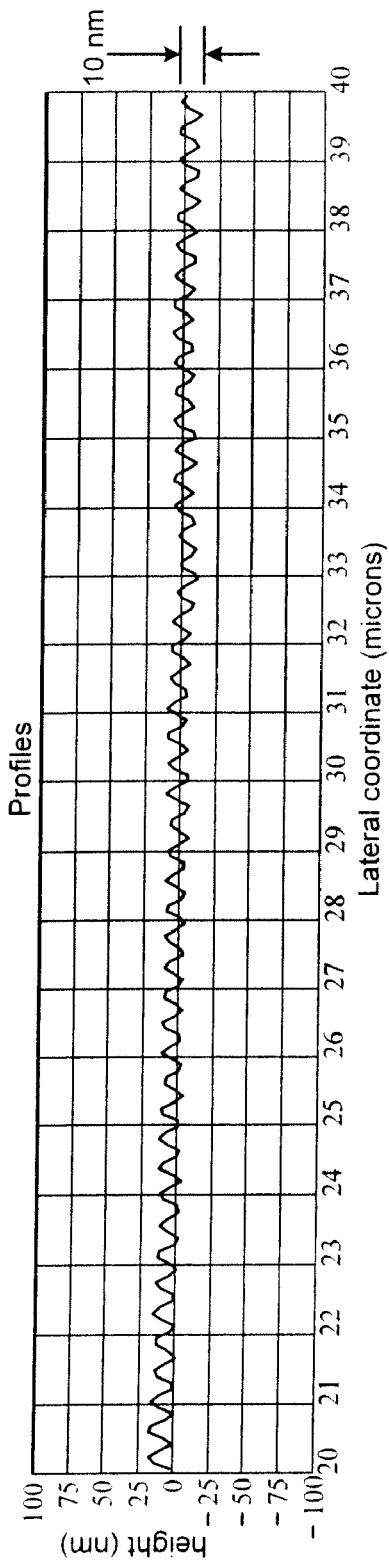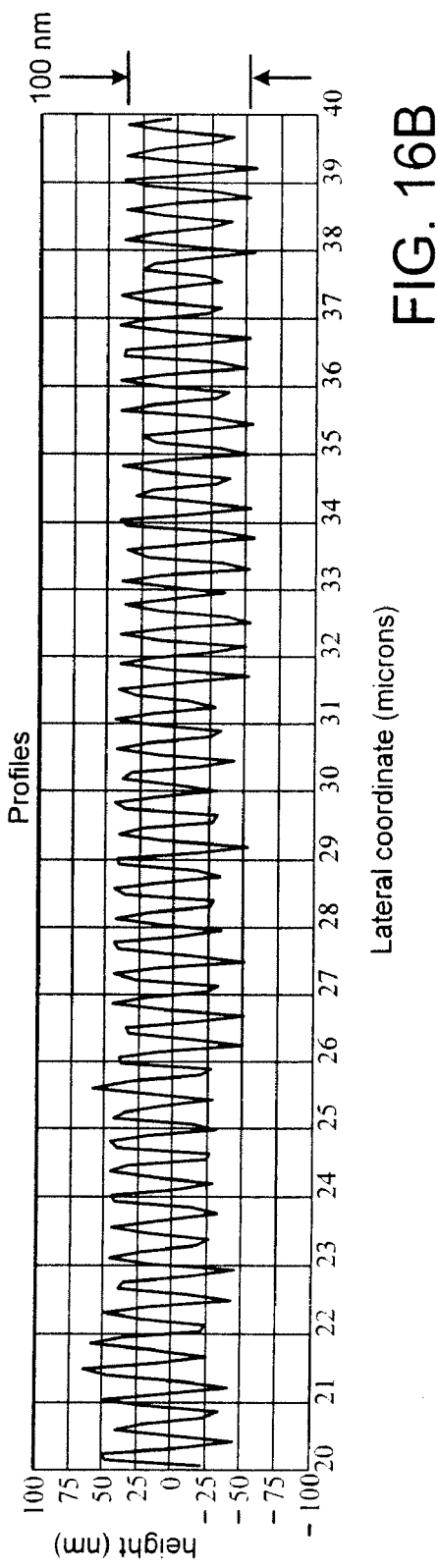

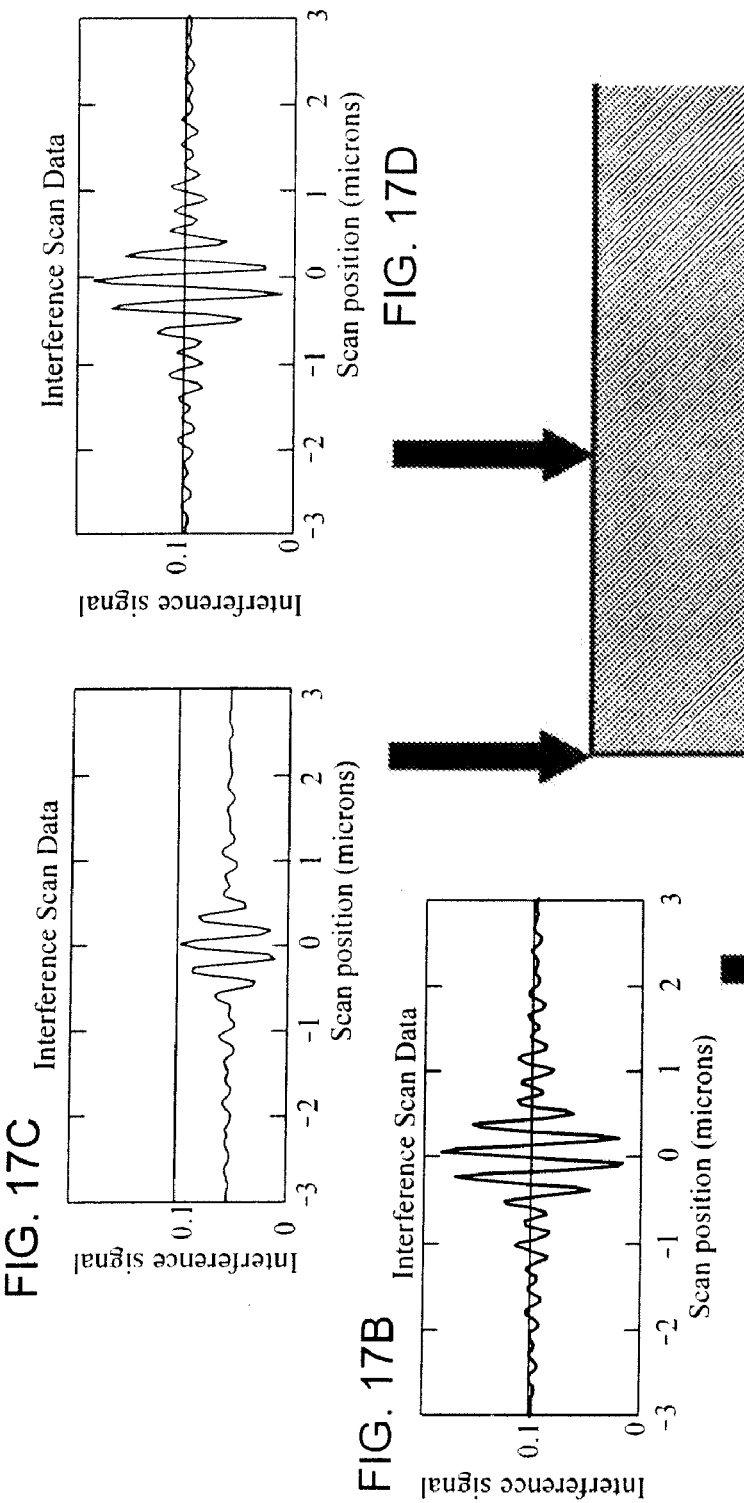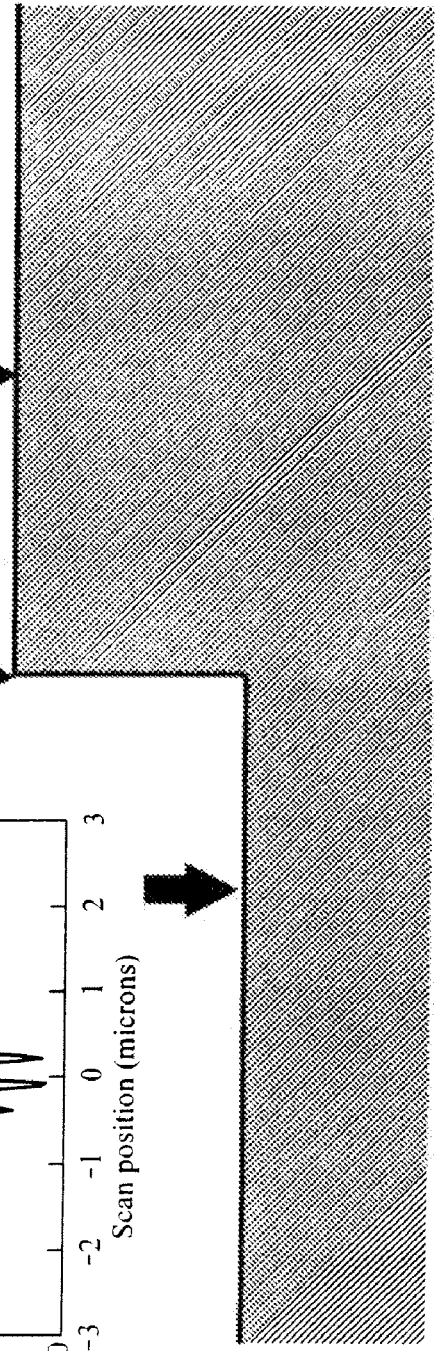

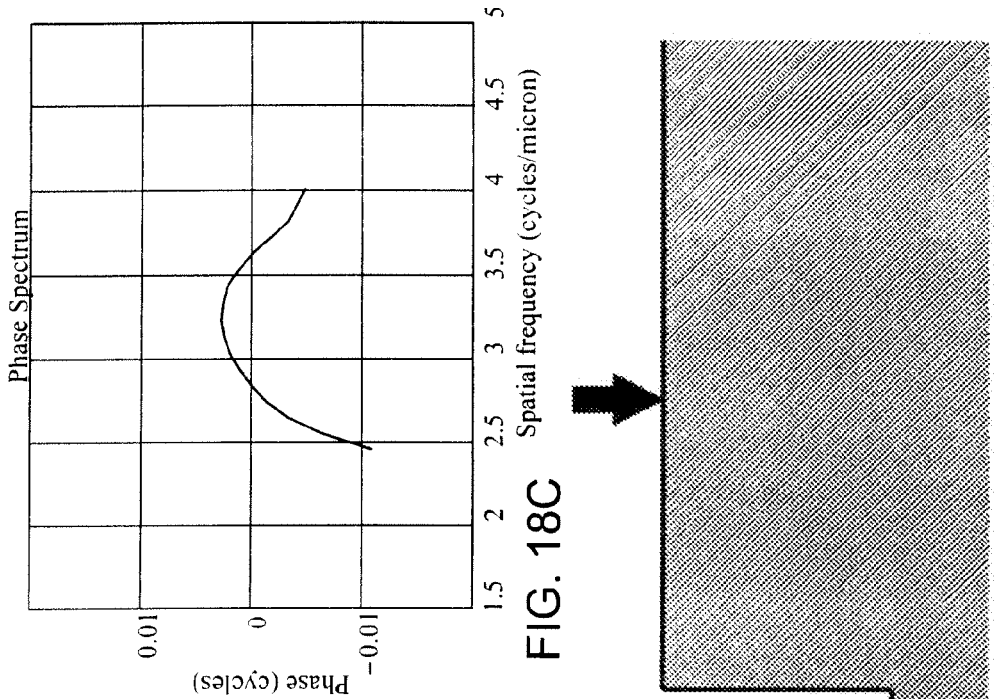
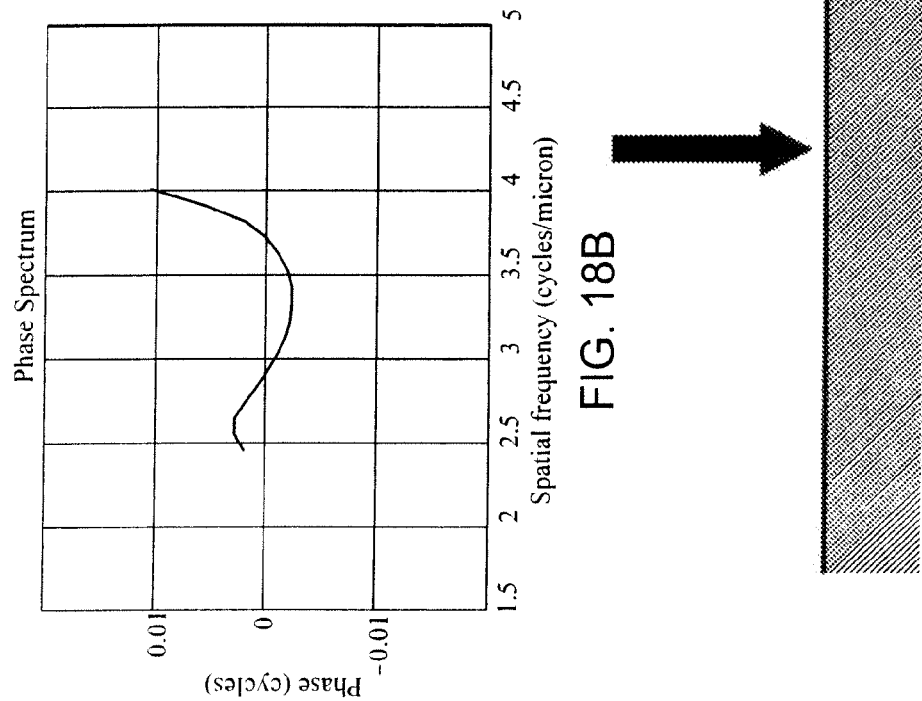
FIG. 18A
FIG. 18B
FIG. 18C

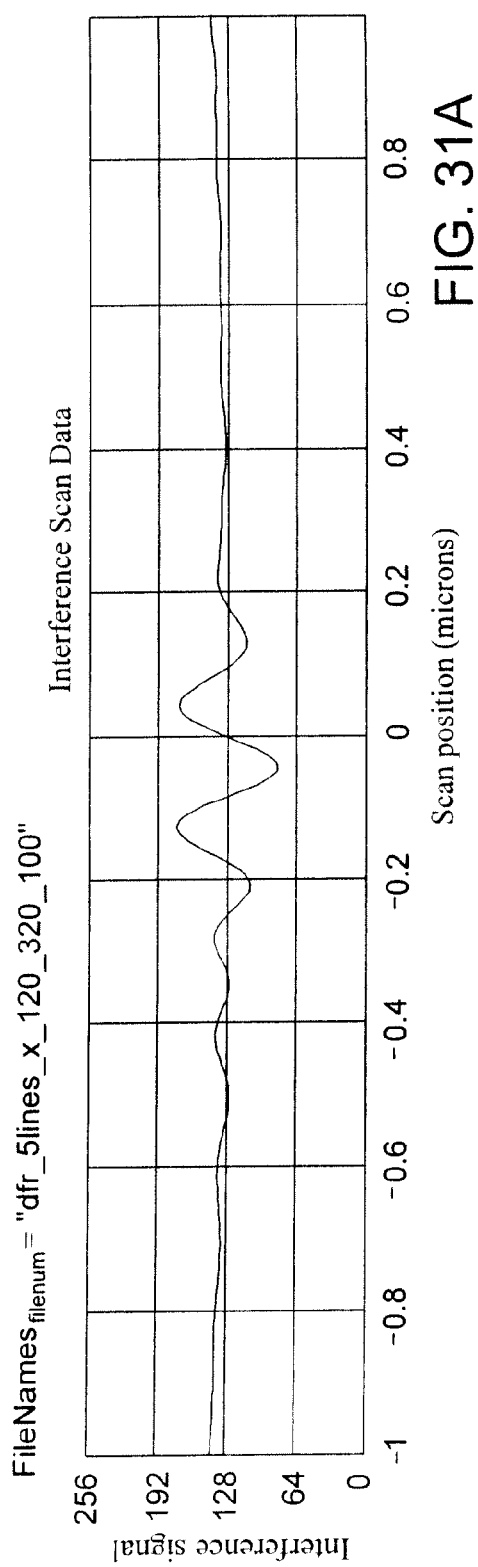
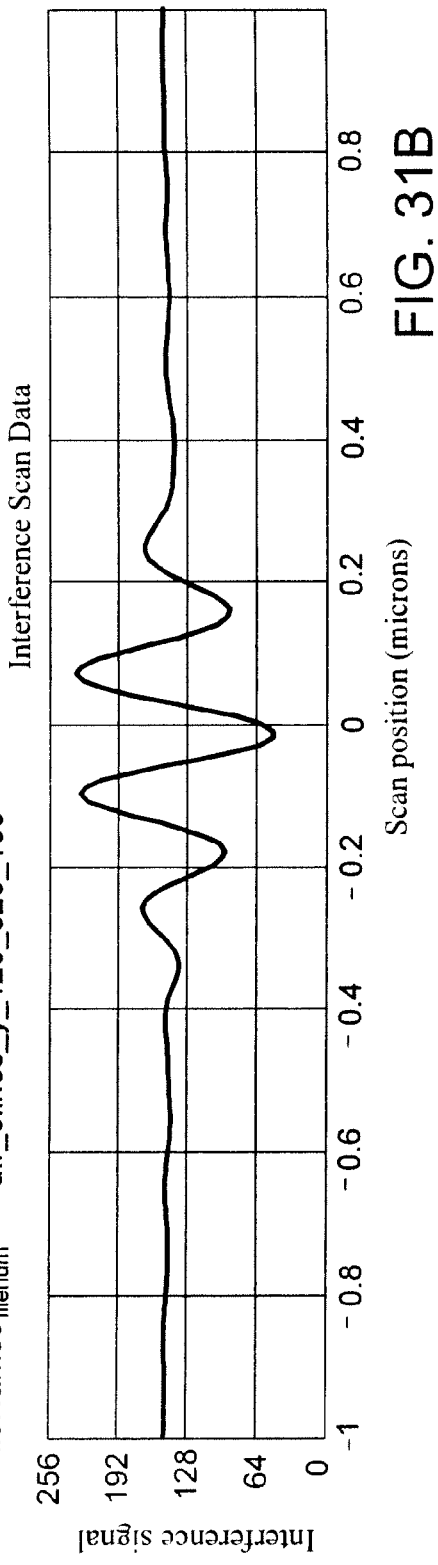

INTERFEROMETER AND METHOD FOR MEASURING CHARACTERISTICS OF OPTICALLY UNRESOLVED SURFACE FEATURES

CROSS-REFERENCE TO RELATED APPLICATIONS

This application claims priority to and is a continuation of U.S. patent application Ser. No. 11/525,355, filed Sep. 21, 2006, now U.S. Pat. No. 7,324,214 which claims priority to U.S. Provisional Patent Application Ser. No. 60/737,016, filed Nov. 15, 2005, this application also claims the benefit under 35 U.S.C. 120, and is a continuation-in-part, of U.S. patent application Ser. No. 10/795,579 filed Mar. 8, 2004, now U.S. Pat. No. 7,271,918 which in turn claims priority to the following U.S. Provisional Patent Applications: U.S. Patent Application Ser. No. 60/452,615, filed Mar. 6, 2003, U.S. Patent Application Ser. No. 60/452,465, filed Mar. 6, 2003, and U.S. Patent Application Ser. No. 60/539,437, filed Jan. 26, 2004. All of said related applications are incorporated herein by reference.

BACKGROUND

The invention relates to using scanning interferometry to measure surface topography and/or other characteristics of objects having complex surface structures, such as thin film(s), discrete structures of dissimilar materials, or discrete structures that are underresolved by the optical resolution of an interference microscope. Such measurements are relevant to the characterization of flat panel display components, semiconductor wafer metrology, and in-situ thin film and dissimilar materials analysis.

Interferometric techniques are commonly used to measure the profile of a surface of an object. To do so, an interferometer combines a measurement wavefront reflected from the surface of interest with a reference wavefront reflected from a reference surface to produce an interferogram. Fringes in the interferogram are indicative of spatial variations between the surface of interest and the reference surface.

Typically, a scanning interferometer scans the optical path length difference (OPD) between the reference and measurement legs of the interferometer over a range comparable to, or larger than, the coherence length of the interfering wavefronts, to produce a scanning interferometry signal for each camera pixel used to measure the interferogram. A limited coherence length can be produced, for example, by using a white-light source, which is referred to as scanning white light interferometry (SWLI). A typical scanning white light interferometry (SWLI) signal is a few fringes localized near the zero optical path difference (OPD) position. The signal is typically characterized by a sinusoidal carrier modulation (the "fringes") with bell-shaped fringe-contrast envelope. The conventional idea underlying SWLI metrology is to make use of the localization of the fringes to measure surface profiles.

SWLI processing techniques include two principle trends. The first approach is to locate the peak or center of the envelope, assuming that this position corresponds to the zero optical path difference (OPD) of a two-beam interferometer for which one beam reflects from the object surface. The second approach is to transform the signal into the frequency domain and calculate the rate of change of phase with wavelength, assuming that an essentially linear slope is directly proportional to object position. See, for example, U.S. Pat. No. 5,398,113 to Peter de Groot. This latter approach is referred to as Frequency Domain Analysis (FDA).

Unfortunately such assumptions may break down when applied to a test object having a thin film because of reflections by the top surface and the underlying film/substrate interface. Recently a method was disclosed in U.S. Pat. No. 6,545,763 to S. W. Kim and G. H. Kim to address such structures. The method fit the frequency domain phase profile of a SWLI signal for the thin film structure to an estimated frequency domain phase profile for various film thicknesses and surface heights. A simultaneous optimization determined the correct film thickness and surface height.

Complex surface structures, e.g. patterned semiconductor wafers, may be comprised of features of dissimilar materials of various sizes from mm down to a few tens of nm in size.

It is presently of considerable interest in the several industries, including in particular the semiconductor industry, to make quantitative measurements of surface topography. Due to the small size of typical chip features, the instruments used to make these measurements typically should have high spatial resolution both parallel and perpendicular to the chip surface. Engineers and scientists use surface topography measuring systems for process control and to detect defects that occur in the course of manufacturing, especially as a result of processes such as etching, polishing, cleaning and patterning.

Non-optical metrology tools such as top down critical dimension (CD) scanning electron microscopy (SEM) and atomic force microscopy (AFM) are in widespread use for obtaining pattern and topography information in the semiconductor industry. While both of these techniques have the required horizontal resolution they suffer from being extremely slow so that it requires significant amounts of time to collect data over large areas of the wafer. This is particularly true of the AFM. Top down CD SEM's are programmable and so can automatically collect data from particular regions of a set of wafers but even with this feature the time required to collect full wafer data is prohibitive.

Conventional optical surface profilers such as confocal, interferometric or slope sensors overcome some of these difficulties; but generally become unusable when surface features are either too small, too closely spaced or both, to be properly resolved and result in inaccurate surface height variations.

Conventional interference microscopes measure surface profiles by directly associating interference phase with an optical path difference between a reference surface and a measurement surface. They have lateral resolution typically limited to approximately one wavelength of the source illumination.

Scanning white light interference microscopes, also known as coherence probe microscopes, laser radar and vertical scanning interferometers, measure surface profiles take advantage of the limited coherence of white light (or more generally, broadband) illumination to assist in surface profiling of discrete surface features, rough surface structures and narrow lines. They have lateral resolution typically limited to approximately one wavelength of the source illumination. Some of these systems may be arranged so as to measure the thickness of films.

Scatterometers determine a surface characteristic by matching the distribution of scattered or diffracted light to a pre-computed library of the scattering and diffraction distributions from nominal structures. They do not directly measure surface profiles with respect to a reference, as in an interferometer. Scatterometers also generally work only with a limited set of 2D structures.

Confocal microscopes use a restricted depth of focus to section an object vertically, so as to e.g. determine surface profile.

Nomarski microscopy and other differential techniques measure differences in surface height by comparing them to each other.

Ellipsometers measure the thin film and dissimilar material structure of objects using polarized light at high angles of incidence and the Fresnel reflection coefficients. Generally the features of interest are large compared to the source wavelength and ellipsometers do not provide surface profile information.

SUMMARY

The inventors have realized that there is a wealth of information in a scanning interfometry signal, much of which is ignored in conventional processing. While complex surface structures, such as thin films or under-resolved surface features (i.e., lateral surface features smaller than the spatial resolution of the interference microscope), may corrupt conventional processing techniques based on identifying the location of the peak in the fringe contrast envelope or calculating a slope for the frequency domain phase profile, new processing techniques disclosed herein can extract surface height information and/or information about that the complex surface structure.

For example, while not assuming that the surface height information is directly related to the peak in the fringe contrast envelope, some embodiments of the invention assume that a change in surface height translates the scanning interferometry signal with respect to a reference scan position, but otherwise preserves the shape of the scanning interferometry signal. Thus, the shape of the scanning interferometry signal is especially useful in characterizing complex surface structure because it is independent of surface height. Similarly, in the frequency domain, some embodiments assume a change in surface height introduces a linear term in the frequency domain phase profile, even though the frequency domain profile itself may not be linear. However, the change in surface height leaves the frequency domain amplitude profile unchanged. Therefore, the frequency domain amplitude profile is especially useful in characterizing complex surface structure.

After the complex surface structure is characterized, surface height can be efficiently determined. For example, a cross-correlation between the scanning interferometry signal and a model signal having the shape corresponding to the complex surface structure can produce a peak at a scan coordinate corresponding to the surface height. Similarly, in the frequency domain, a phase contribution resulting from the complex surface structure can be subtracted from the frequency domain phase profile and the surface height can be extracted using a conventional FDA analysis.

Examples of complex surface structure include: simple thin films (in which case, for example, the variable parameter of interest may be the film thickness, the refractive index of the film, the refractive index of the substrate, or some combination thereof); multilayer thin films; sharp edges and surface features that diffract or otherwise generate complex interference effects; unresolved surface roughness; unresolved surface features, for example, a sub-wavelength width groove on an otherwise smooth surface; dissimilar materials (for example, the surface may comprise a combination of thin film and a solid metal, in which case the library may include both surface structure types and automatically identify the film or the solid metal by a match to the corresponding frequency-domain spectra); surface structure that give rise to optical activity such as fluorescence; spectroscopic properties of the surface, such as color and wavelength-dependent reflectivity; polarization-dependent properties of the surface; and deflections, vibrations or motions of the surface or deformable surface features that result in perturbations of the interference signal.

In some embodiments, the limited coherence length of the light used to generate the scanning interferometry signal is based on a white light source, or more generally, a broadband light source. In other embodiments, the light source may be monochromatic, and the limited coherence length can result from using a high numerical aperture (NA) for directing light to, and/or receiving light from, the test object. The high NA causes light rays to contact the test surface over a range of angles, and generates different spatial frequency components in the recorded signal as the OPD is scanned. In yet further embodiments, the limited coherence can result from a combination of both effects.

The origin of the limited coherence length is also a physical basis for there being information in the scanning interferometry signal. Specifically, the scanning interferometry signal contains information about complex surface structure because it is produced by light rays contacting the test surface with many different wavelengths and/or at many different angles.

In the processing techniques described herein, information derivable from a scanning interferometry signal for a first surface location of a test object (including the scanning interferometry signal itself) is compared to information corresponding to multiple models of the test object, where the multiple models are parametrized by a series of characteristics for the test object. For example, the test object can be modeled as a thin film and the series of characteristics can be a series of values for the thickness of the thin film. While the information being compared might include, for example, information about the frequency domain phase profile, it might also include information about the shape of the scanning interferometry data and/or information about the frequency domain amplitude profile. Furthermore, to focus the comparison on the complex surface structure, and not the surface height at the first surface location, the multiple models can all correspond to a fixed surface height for the test object at the first surface location. The comparison itself can be based on calculating a merit function indicative of the similarity between the information from the actual scanning interferometry signal and the information from each of the models. For example, the merit function can be indicative of fit between the information derivable from the scanning interferometry data and function parametrized by the series of characteristics.

Furthermore, in some embodiments, the series of characteristics corresponds to a characteristic of the test object at second location different from the first location, including for example, diffractive surface structures that contribute to the interface signal for the first surface locations. Thus, while we often refer to the complex surface structure as being something other than surface height at the first surface location corresponding to the scanning interferometry signal, the complex surface structure may correspond to surface height features spaced from the first surface location corresponding to the scanning interferometry signal.

In yet further embodiments, the information derivable from the scanning interferometry signal is an estimate for the relative surface height for the first location. This information is compared to models which calculate what the apparent height would be for the first surface location as measured by the interferometry system (taking into account the affect of under-resolved features at multiple surface locations) for different values of the actual surface height profile. Based on the comparison, one improves the accuracy of the surface height measurement, e.g., by selecting the actual surface heights used in the model that produced apparent heights most similar to those from the actual measurement.

More generally, information can be derived from the scanning interferometry signals at multiple surface locations (even if at least some of the surface features present at those locations are under-resolved), and this information can be compared to models which calculate what the information should look like as a function of different values parametrizing under-resolved features of interest. For example, the derivable information can correspond to an observed surface profile determined using conventional scanning interferometry algorithms. The under-resolved features of interest will be obscured in this surface profile; however, they will still contribute to the observed surface profile and information about the under-resolved features can be extracted from the observed surface profile by comparing it to different models.

For example, the individual lines of an under-resolved grating structure will not be apparent in the surface profile observed from conventional processing of the interferometry signals at multiple surface locations. Nonetheless, for example, the inventors have discovered that the actual modulation depth of the grating structure can be correlated to the surface height of the collective grating structure apparent in surface profile obtained from conventionally processed scanning interferometry signals.

The observed surface height of the collective grating structure is an example of an "apparent" property of the test surface. In other words, it is example of a property related to how the test surface appears to the measuring instrument because the test surface includes under-resolved features. Such apparent properties can be compared to different models of the expected response of the instrument as parametrized by different values characterizing the under-resolved features of the test surface. The comparison can reveal which of the different values yields the expected response most similar to the observed response to thereby provide information about the under-resolved feature of the test object based on the apparent property derived from the scanning interferometry signal(s).

The measurement technique and subsequent analysis approach described herein is applicable to several semiconductor processing steps. With the use of optical proximity corrections and/or phase shift masks, dimensions of patterned objects can be smaller than the wavelength used by the optical lithography tool. For example, 193 nm lithography tools pattern 65 nm objects in today's high volume manufacturing facilities routinely; the use of etch bias steps and hard mask structures can extend the lower limit to 45 nm and below. With the ability to print sub wavelength features comes the need to monitor these features and the associated etch and deposition steps. The embodiments of the current disclosure enable measurements of the nested patterned structures, where nested is defined as a repeated surface structure of known shape whose periodicity is comparable to the lateral dimension of the structure. In particular, these nested structures could be used to monitor the following process steps: isolation patterning and etch, poly-silicon gate electrode patterning and etch, source/drain etch and deposition, as well as many front end metallization patterning, etch, and polish processes. Additional applications include measurements of resist over some film/substrate. Exposure and focus curves are characterized by line width and depth changes that are measurable with the inventive apparatus and method.

One example of such in-process metrology measurements of semiconductor chips include using scanning interferometry measurements for non-contact surface topography measurements of semiconductor wafers during chemical mechanical polishing (CMP) of a dielectric layer on the wafer. CMP is used to create a smooth surface for the dielectric layer, suitable for precision optical lithography. Based on the results of the interferometric topography methods, the process conditions for CMP (e.g., pad pressure, polishing slurry composition, etc.) can be adjusted to keep surface non-uniformities within acceptable limits.

We now summarize various aspects and features of the invention.

In general, in one aspect, a method is disclosed including: (i) comparing information derivable from multiple interferometry signals corresponding to different surface locations of a test object to information corresponding to multiple models of the test object, wherein the multiple models are parametrized by a series of characteristics that relate to one or more under-resolved lateral features of the test object; and (ii) outputting information about the under-resolved surface feature based on the comparison.

Embodiments of the method may include any of the following features.

The one or more under-resolved lateral features of the test object may correspond to one or more of a pitch, a modulation depth, and an element width for an under-resolved patterned lateral structure on the test object. For example, the series of characteristics can include different values for the modulation depth. Furthermore, the multiple models may be represented by a correlation that maps possible outcomes for the information derivable from the multiple interferometry signals to corresponding ones of the different values for the modulation depth, and the comparing may be determining which of the different values for the modulation depth best corresponds to the information derivable from the multiple interferometry signals.

The modulation depth can be expressed relative to bias offset value.

At least some of the interferometry signals may be derived from an illumination of the test object whose polarization is oriented with respect to the elements of the patterned lateral structure. For example, the polarization may be a linear polarization aligned orthogonal to the length of the individual elements that define the patterned lateral structure. (Referred to in the specification as "x-polarization.")

The one or more under-resolved lateral features of the test object may correspond to one or more of a height and a position of a step on the test object. For example, the series of characteristics may include different values for the height or position of the step height.

The information derivable from the multiple interferometry signals may include one or more values extracted from a height profile for the test object derived from the multiple interferometry signals, wherein the under-resolved surface feature is obscured or does not apparent in the extracted height profile. For example, the test object can include a patterned lateral structure whose individual element are obscured or do not apparent in the extracted surface height profile.

The information derivable from the multiple interferometry signals may be a value for a height for a collection of under-resolved elements in the patterned lateral structure extracted from the height profile. The information about the under-resolved surface feature may correspond to one or more of a modulation depth and an element width for the patterned lateral structure.

The different surface locations for the interferometry signals may include a reference portion of the test object providing a reference height value for the extracted height profile. For example, the test object may be etched to produce the patterned structure, and the reference portion of the test object may be a portion of the test object known to not be etched.

At least some of the interferometry signals from which the height profile is determined may be derived from an illumination of the test object whose polarization is oriented with respect to the elements of the patterned lateral structure. For example, the polarization may be a linear polarization aligned orthogonal to the length of the individual elements that define the patterned lateral structure (x-polarization).

The height profile may be obtained from a frequency domain analysis of the interferometry signals. Alternatively, the height profile may be obtained from a relative position of a coherence peak in each interferometry signal. The height profile may also be obtained using other methods.

The under-resolved lateral features of the test object may have a feature size smaller than 400 nm, smaller than 200 nm, or even smaller than 100 nm.

The models may be generated computationally using rigorous coupled wave analysis (RCWA).

The models may be generated empirically from test objects having known properties.

The information about the under-resolved surface feature may be outputted to a user.

The information about the under-resolved surface feature may be outputted to an automated process control system for semiconductor manufacturing.

The interferometry signals may be scanning interferometry signals. For example, the scanning interferometry signal may be produced by imaging test light emerging from the test object to interfere with reference light on a detector, and varying an optical path length difference from a common source to the detector between interfering portions of the test and reference light, wherein the test and reference light are derived from the common source, and wherein the scanning interferometry signal corresponds to an interference intensity measured by the detector as the optical path length difference is varied. The method may further include producing the scanning interferometry signal.

Such scanning interferometry signals may be low-coherence scanning interferometry signals. For example, the test and reference light can have a spectral bandwidth greater than 5% of a central frequency for the test and reference light, and the optical path length difference is varied over a range larger than the spectral coherence length corresponding to that bandwidth to produce the scanning interferometry signal. The low coherence may also result when the optics used to direct test light onto the test object and image it to the detector define a numerical aperture for the test light greater than 0.8. To reduce the coherence length, the common source can be a spatially extended source.

In another related aspect, an apparatus is disclosed including: a computer readable medium having a program that causes a processor in a computer to compare information derivable from multiple interferometry signals corresponding to different surface locations of a test object to information corresponding to multiple models of the test object, wherein the multiple models are parametrized by a series of characteristics that relate to one or more under-resolved lateral features of the test object, and output information about the under-resolved surface feature based on the comparison.

In another related aspect, an apparatus is disclosed including: (i) an interferometry system configured to produce multiple interferometry signals corresponding to different surface locations of a test object; and (ii) an electronic processor coupled to the interferometry system to receive the interferometry signals and programmed to compare information derivable from the multiple interferometry signals to information corresponding to multiple models of the test object, wherein the multiple models are parametrized by a series of characteristics that relate to one or more under-resolved lateral features of the test object, and output information about the under-resolved surface feature based on the comparison.

Embodiments of the two apparatus may include any of the features described above for the corresponding method.

In another aspect, a method is disclosed for determining one or more spatial properties of a grating structure on a test object, wherein the grating structure includes line elements having widths smaller than 400 nm so that the line elements are not fully resolved by an interference microscope. The method including: (i) determining an apparent height for a collection of at least some of the grating lines from interference signals at different locations of the test object measured by the interference microscope; (ii) providing an expected response for the interference microscope for different possible values for the properties of the grating structure, wherein the expected response includes contributions from under-resolved line elements of the grating structure; (iii) comparing the apparent height to the expected response for the different possible values to determine information about the spatial properties of a grating structure; and (iv) outputting the determined information about the spatial properties of the grating structure.

In addition to features mentioned above, embodiments of this method may include any of the following features.

The apparent height may be determined with reference to a reference portion of the test object.

The interference microscope may illuminate the grating structure with light polarized orthogonal to length of the individual grating lines (x-polarization) when determining the apparent height.

The determined information about the spatial properties of the grating structure may correspond to a modulation depth for the grating structure.

The grating structure may be a series of periodically spaced lines formed at least in part by etching portions of the test object between the lines.

The interference signals may be scanning interference signals produced by imaging test light emerging from the test object to interfere with reference light on a detector, and varying an optical path length difference from a common source to the detector between interfering portions of the test and reference light, wherein the test and reference light are derived from the common source, and wherein each scanning interferometry signal corresponds to an interference intensity measured by the detector as the optical path length difference is varied. For example, the optical path length difference may be varied over a range larger than the coherence length of the interference microscope.

In a related aspect, an apparatus is disclosed for determining one or more spatial properties of a grating structure on a test object, wherein the grating structure includes line elements having widths smaller than 400 nm so that the line elements are not fully resolved by an interference microscope, the apparatus including: a computer readable medium having a program that causes a processor in a computer to: 1) determine an apparent height for a collection of at least some of the grating lines from interference signals at different locations of the test object measured by the interference microscope; 2) provide an expected response for the interference microscope for different possible values for the properties of the grating structure, wherein the expected response includes contributions from under-resolved line elements of the grating structure; 3) compare the apparent height to the expected response for the different possible values to determine information about the spatial properties of a grating structure; and 4) output the determined information about the spatial properties of the grating structure.

In another related aspect, an apparatus is disclosed for determining one or more spatial properties of a grating structure on a test object, wherein the grating structure includes line elements having widths smaller than 400 nm so that the line elements are not fully resolved by an interference microscope, the apparatus including: the interference microscope; and an electronic processor coupled to the interference microscope and programmed to: 1) determine an apparent height for a collection of at least some of the grating lines from interference signals at different locations of the test object measured by the interference microscope; 2) provide an expected response for the interference microscope for different possible values for the properties of the grating structure, wherein the expected response includes contributions from under-resolved line elements of the grating structure; 3) compare the apparent height to the expected response for the different possible values to determine information about the spatial properties of a grating structure; and 4) output the determined information about the spatial properties of the grating structure.

Embodiments of the two apparatus may include any of the features described above for the corresponding method.

In another aspect, a method is disclosed: (i) determining one or more apparent properties of a test surface from interferometry signals produced by an interferometry system; (ii) comparing the apparent properties determined from the interferometry signals to an expected response for the interferometry system for different possible values for one or more under-resolved features of the test surface; and (iii) outputting information about the one or more under-resolved features of the test surface based on the comparison.

In addition to features mentioned above, embodiments of this method may include any of the following features.

The interferometry system may be a scanning interferometry system.

The apparent properties of the test surface may be determined from the interferometry signal based on variations in any of interference phase, interference contrast, and surface reflectivity.

The expected response may be calculated for variations in one or more of surface height and surface composition.

The test surface may include a patterned structure having a modulation depth, a periodicity, and elements having a width, wherein the expected response is calculated for variations in one or more of the modulation depth, the periodicity, and element width. For example, the expected response may be calculated for variations in the modulation depth.

The correspondence between the actual modulation depth and the apparent modulation calculated for the expected response may include a positive correlation over a first range of actual modulation depths and a negative correlation over a second range of actual modulation depths.

The information about the one or more under-resolved features may be used to monitor one or more semiconductor processing steps, such as any of isolation patterning and etch, poly-silicon gate electrode patterning and etch, source/drain etch and deposition, and metallization patterning, etch, and polish processing.

In another related aspect, an apparatus is disclosed including: a computer readable medium having a program that causes a processor in a computer to: 1) determine one or more apparent properties of a test surface from interferometry signals produced by an interferometry system; 2) compare the apparent properties determined from the interferometry signals to an expected response for the interferometry system for different possible values of one or more under-resolved features of the test surface; and 3) output information about the one or more under-resolved features of the test surface based on the comparison.

In another related aspect, an apparatus is disclosed including: an interferometry system configured to produce multiple interferometry signals corresponding to different surface locations of a test object; and an electronic processor coupled to the interferometry system to receive the interferometry signals and programmed to: 1) determine one or more apparent properties of a test surface from the interferometry signals; 2) compare the apparent properties determined from the interferometry signals to an expected response for the interferometry system for different possible values of one or more under-resolved features of the test surface; and 3) output information about the one or more under-resolved features of the test surface based on the comparison.

Embodiments of the two apparatus may include any of the features described above for the corresponding method.

In another aspect, a method is disclosed including: (i) determining one or more apparent properties of a test surface from an interferometry signal (e.g., a scanning interferometry signal) produced by an interferometry system; (ii) providing an expected response for the interferometry system for different possible values of the properties of the test surface (for example, variations in one or more of surface height and surface composition), wherein the expected response includes contributions from underresolved features of the test surface; and (iii) comparing the apparent properties determined from the interferometry signal to the expected response for the different values of the properties to improve the accuracy of the determined properties.

Embodiments of the method may include any of the following features.

The apparent properties of the test surface can be determining from the interferometry signal based on variations in any of interference phase, interference contrast, and surface reflectivity.

The expected response can be calculated for variations in one or more of surface height and surface composition. For example, the test surface can include a patterned structure (e.g., a grating) having a modulation depth, a periodicity, and elements having a width, and wherein the expected response is calculated for variations in one or more of the modulation depth, the periodicity, and element width.

The correspondence between the apparent property associated with the interferometry signal and the actual values of the property used to generate models can include a positive correlation over a first range of actual modulation depths and a negative correlation over a second range of actual modulation depths. For example, in a specific embodiment, the expected response is calculated for variations in the modulation depth. In such cases, the correspondence between the actual modulation depth and the apparent modulation calculated for the expected response can include a positive correlation over a first range of actual modulation depths and a negative correlation over a second range of actual modulation depths.

In further embodiments, the underresolved feature can be single trench, step, or protrusion, rather than a series of such elements as in the patterned structure. In such examples, the information from the actual signal and for models can correspond to any of the depth (or height for the case of the step or protrusion) and the location or width of the features.

The method can further include using the improved accuracy of the measured properties of the test surface to monitor semiconductor processing steps. For example, such processing steps can include any of isolation patterning and etch, poly-silicon gate electrode patterning and etch, source/drain etch and deposition, and metallization patterning, etch, and polish processing.

In another aspect, an apparatus is disclosed including: a computer readable medium having a program that causes a processor in a computer to compare apparent properties of a test surface determined from an interferometry signal produced by an interferometry system to an expected response for the interferometry system for different possible values of the properties of the test surface, wherein the expected response includes contributions from underresolved features of the test surface, and improve the accuracy of the determined properties based on the comparison.

In yet another aspect, an apparatus is disclosed including: an interferometry system configured to produce an interferometry signal; and an electronic processor coupled to the interferometry system to receive the interferometry signal and programmed to compare apparent properties of a test surface determined from an interferometry signal produced by an interferometry system to an expected response for the interferometry system for different possible values of the properties of the test surface, wherein the expected response includes contributions from underresolved features of the test surface, and improve the accuracy of the determined properties based on the comparison.

Embodiments of such apparatus can further include features corresponding to any of those mentioned above in conjunction with the corresponding method. In general, in another aspect, the invention features a method including: comparing information derivable from a scanning interferometry signal for a first surface location of a test object to information corresponding to multiple models of the test object, wherein the multiple models are parametrized by a series of characteristics for the test object.

Embodiments of the invention may include any of the following features.

The method may further include determining an accurate characteristic for the test object based on the comparison.

The method may further include determining a relative surface height for the first surface location based on the comparison. Furthermore, the determining of the relative surface height may include determining which model corresponds to an accurate one of the characteristic for the test object based on the comparison, and using the model corresponding to the accurate characteristic to calculate the relative surface height.

For example, the using of the model corresponding to the accurate characteristic may include compensating data from the scanning interferometry signal to reduce contributions arising from the accurate characteristic. The compensating of the data may include removing a phase contribution arising from the accurate characteristic from a phase component of a transform of the scanning interferometry signal for the test object, and the using of the model corresponding to the accurate characteristic may further include calculating the relative surface height from the phase component of the transform after the phase contribution arising from the accurate characteristic has been removed.

In another example, using the model corresponding to the accurate characteristic to calculate the relative surface height may include determining a position of a peak in a correlation function used to compare the information for the test object to the information for the model corresponding to the accurate characteristic.

The method may further include comparing information derivable from the scanning interferometry signal for additional surface locations to the information corresponding to the multiple models. Also, the method may further include determining a surface height profile for the test object based on the comparisons.

The comparing may include calculating one or more merit functions indicative of a similarity between the information derivable from the scanning interferometry signal and the information corresponding to each of the models.

The comparing may include fitting the information derivable from the scanning interferometry signal to an expression for the information corresponding to the models.

The information corresponding to the multiple models may include information about at least one amplitude component of a transform (e.g., a Fourier transform) of a scanning interferometry signal corresponding to each of the models of the test object. Likewise, the information derivable from the scanning interferometry signal includes information about at least one amplitude component of a transform of the scanning interferometry signal for the test object.

The comparing may include comparing a relative strength of the at least one amplitude component for the test object to the relative strength of the at least one amplitude component for each of the models.

The information corresponding to the multiple models may be a function of a coordinate for the transform. For example, the information corresponding to the multiple models may include an amplitude profile of the transform for each of the models. Furthermore, the comparing may include comparing an amplitude profile of a transform of the scanning interferometry signal for the test object to each of the amplitude profiles for the models.

The comparing may also include comparing information in a phase profile of the transform of the scanning interferometry signal for the test object to information in a phase profile of the transform for each of the models. For example, the information in the phase profiles may include information about nonlinearity of the phase profile with respect to the transform coordinate and/or information about a phase gap value.

The information derivable from the scanning interferometry signal and which is being compared may be a number. Alternatively, the information derivable from the scanning interferometry signal and which is being compared may be a function. For example, it may be a function of scan position or a function of spatial frequency.

The information for the test object may be derived from a transform (e.g., a Fourier transform) of the scanning interferometry signal for the test object into a spatial frequency domain. The information for the test object may include information about an amplitude profile of the transform and/or a phase profile of the transform.

The information for the test object may relate to a shape of the scanning interferometry signal for the test object at the first location. For example, the information for the test object may relate to a fringe contrast magnitude in the shape of the scanning interferometry signal. It may also relate to a relative spacings between zero-crossings in the shape of the scanning interferometry signal. It may also be expressed as a function of scan position, wherein the function is derived from the shape of the scanning interferometry signal.

The comparing may include calculating a correlation function (e.g., a complex correlation function) between the information for the test object and the information for each of the models. The comparing may further include determining one or more peak values in each of the correlation functions. The method may then further include determining an accurate characteristic for the test object based on the parameterization of the model corresponding to the largest peak value. Alternately, or in addition, the method may further include determining a relative surface height for the test object at the first surface location based on a coordinate for at least one of the peak values in the correlation functions.

The multiple models may correspond to a fixed surface height for the test object at the first location.

The series of characteristics may include a series of values for at least one physical parameter of the test object. For example, the test object may include a thin film layer having a thickness, and the physical parameter may be the thickness of the thin film at the first location.

The series of characteristics may include a series of characteristics of the test object at a second surface location different from the first surface location. For example, the test object may include structure at the second surface location that diffracts light to contribute to the scanning interferometry signal for the first surface location. In one example, the series of characteristics at the second surface location may include permutations of a magnitude for a step height at the second location and a position for the second location. In another example, the series of characteristics at the second surface location may include permutations of a modulation depth for a grating and an offset position of the grating, wherein the grating extends over the second location.

Moreover, the information derivable from the interferometry signal can correspond to an estimate for the relative surface height of the first surface location. For example, the estimate of the relative of the first surface location can based on frequency domain analysis of the interferometry signal, or the estimate of the relative surface height of the first surface location can be based on a relative position of a coherence peak in the interferometry signal.

The method can further include comparing information derivable from an interferometry signal for one or more additional surface locations of the test object, including the second surface location, to the information corresponding to the multiple models of the test object.

For example, the information derivable from the interferometry signal for the first and additional surface locations can correspond to a surface height profile for the test object for a range of surface locations including the first and additional surface locations. Also, the information corresponding to the multiple models can include a surface height profile expected to be produced by an interferometry system used to produce the interferometry signal when using conventional processing of the interferometry signal for each of the multiple models of the test object, wherein the expected surface height profiles include contributions from underresolved features that cause the interference signal for the first surface location to include contributions related to test object features at the second surface location. For example, the test object can include structure at the second surface location that diffracts light to contribute to the interferometry signal for the first surface location.

In one example, the test object includes a patterned structure extending over the first and additional surface locations, and the information derivable from the scanning interferometry signal for the first and additional surface locations includes an estimate for at least one of a modulation depth for the patterned structure, a periodicity for the patterned structure, and a width for each element of the patterned structure.

Likewise, for the example of the patterned structure, the series of characteristics at the second surface location can include different values for each of at least one of a modulation depth for the patterned structure, a periodicity for the patterned structure, and a width for each element of the patterned structure at the first surface location.

In further embodiments, the underresolved feature can be single trench, step, or protrusion, rather than a series of such elements as in the patterned structure. In such examples, the information from the actual signal and for models can correspond to any of the depth (or height for the case of the step or protrusion) and the location or width of the features.

The information derivable from the interferometry signal can correspond to an estimate for the relative surface height of the first surface location, and the series of characteristics at the second surface location can corresponds to series of values for a relative surface height at the second surface location.

For example, the test object can include a patterned structure spanning the first and second surface locations, and the estimate for the relative surface height of the first surface location corresponds to an estimate for a modulation depth of the patterned structure and the series of values for the relative surface height at the second surface location also correspond to the modulation depth for the patterned structure. The multiple models can correlate different estimates for the modulation depth to corresponding ones of the values to improve the estimate for the modulation depth.

In some embodiments, the multiple models correlate the information derivable from the interferometry signal to a corresponding value for the information for the multiple models, wherein the correspondence varies from a positive correlation to a negative correlation.

For example, for the case of the patterned structure, the correlation between the different estimates for the modulation depth and the corresponding values for modulation depths from the models varies from a positive correlation to a negative correlation.

The method can further include determining an accurate characteristic for the test object based on the comparison, such as a relative surface height for the first surface location. For example, the determining of the relative surface height can include determining which model corresponds to an accurate one of the characteristic for the test object based on the comparison, and using the model corresponding to the accurate characteristic to determine the relative surface height. The series of characteristics may be a series of surface materials for the test object.

The series of characteristics may be a series of surface layer configurations for the test object.

The scanning interferometry signal may be produced by a scanning interferometry system, and the comparing may include accounting for systematic contributions to the scanning interferometry signal arising from the scanning interferometry system. For example, the systematic contributions may include information about a dispersion in a phase change on reflection from components of the scanning interferometry system. Furthermore, the method may also include comparing information derivable from the scanning interferometry signal for additional surface locations to the information corresponding to the multiple models, in which case, the systematic contributions may be resolved for multiple ones of the surface locations. The method may further include calibrating the systematic contributions of the scanning interferometry system using another test object having known properties.

The scanning interferometry signal may produced by imaging test light emerging from the test object to interfere with reference light on a detector, and varying an optical path length difference from a common source to the detector between interfering portions of the test and reference light, wherein the test and reference light are derived from the common source (e.g., a spatially extended source), and wherein the scanning interferometry signal corresponds to an interference intensity measured by the detector as the optical path length difference is varied.

The test and reference light may have a spectral bandwidth greater than about 5% of a central frequency for the test and reference light.

The common source may have a spectral coherence length, and the optical path length difference is varied over a range larger than the spectral coherence length to produce the scanning interferometry signal.

Optics used to direct test light onto the test object and image it to the detector may define a numerical aperture for the test light greater than about 0.8.

The method may further include producing the scanning interferometry signal.

In another aspect, the invention features an apparatus including: a computer readable medium having a program that causes a processor in a computer to compare information derivable from a scanning interferometry signal for a first surface location of a test object to information corresponding to multiple models for the test object, wherein the multiple models are parametrized by a series of characteristics for the test object.

The apparatus may include any of the features described above in connection with the method.

In another aspect, the invention features an apparatus including: a scanning interferometry system configured to produce a scanning interferometry signal; and an electronic processor coupled to the scanning interferometry system to receive the scanning interferometry signal and programmed to compare information derivable from a scanning interferometry signal for a first surface location of a test object to information corresponding to multiple models of the test object, wherein the multiple models are parametrized by a series of characteristics for the test object.

The apparatus may include any of the features described above in connection with the method.

In general, in another aspect, the invention features a method including: chemically mechanically polishing a test object; collecting scanning interferometry data for a surface topography of the test object; and adjusting process conditions for the chemically mechanically polishing of the test object based on information derived from the scanning interferometry data. For example, the process conditions may be pad pressure and/or polishing slurry composition. In preferred embodiments, adjusting the process conditions based on the information derived from the scanning interferometry data may include comparing information derivable from the scanning interferometry signal for at least a first surface location of a test object to information corresponding to multiple models of the test object, wherein the multiple models are parametrized by a series of characteristics for the test object. Analysis of the scanning interferometry signal may further include any of the features described above with the first-mentioned method.

Unless otherwise defined, all technical and scientific terms used herein have the same meaning as commonly understood by one of ordinary skill in the art to which this invention belongs. In case of conflict with publications, patent applications, patents, and other references mentioned incorporated herein by reference, the present specification, including definitions, will control.

For example, while scanning interferometry most frequently involves mechanically scanning of the relative optical path lengths between reference and measurement legs, as used herein, scanning interferometry is intended to include additional non-mechanical means for varying the relative optical pathlength. For example, the interferometry signal can be generating by varying the center wavelength of the light source over a range of wavelengths in an unequal path length interferometer (i.e., where the nominal optical path length for the reference and measurement paths differ.) The different wavelengths produce different phase shifts for the reference and measurement paths because they have different optical path lengths, thereby varying the phase shifts between the paths.

In addition, while the term "light" can sometimes be understood to be limited to electromagnetic radiation in the visible spectrum, as used herein, the term "light" is intended to include electromagnetic radiation in any of ultraviolet, visible, near-infrared, and infrared spectral regions.

Other features, objects, and advantages of the invention will be apparent from the following detailed description.

BRIEF DESCRIPTION OF THE DRAWINGS

FIG. 8 shows the merit function search procedure for simulation of a $SiO_2$ film on a Si substrate with the thin film thickness being 0.

FIG. 9 shows the merit function search procedure for simulation of a $SiO_2$ film on a Si substrate with the thin film thickness being 50 nm.

FIG. 10 shows the merit function search procedure for simulation of a $SiO_2$ film on a Si substrate with the thin film thickness being 100 nm.

FIG. 11 shows the merit function search procedure for simulation of a $SiO_2$ film on a Si substrate with the thin film thickness being 300 nm.

FIG. 12 shows the merit function search procedure for simulation of a $SiO_2$ film on a Si substrate with the thin film thickness being 600 nm.

FIG. 13 shows the merit function search procedure for simulation of a $SiO_2$ film on a Si substrate with the thin film thickness being 1200 nm.

FIG. 14 shows the surface and substrate profiles determined for a simulation of a $SiO_2$ on Si thin film in which the film thickness varies uniformly from 0 to 1500 nm in 10-nm increments per pixel, with the top surface always at zero.

FIG. 15 shows the surface and substrate profiles determined for a simulation identical to that in FIG. 14 except that random noise has been added (2-bits rms out of an average 128 intensity bits).

FIG. 16 shows surface height profiles determined using conventional FDA analysis (FIG. 16a) and a library search method described herein (FIG. 16b) for a 2400 line per mm grating having an actual peak-to-valley modulation depth of 120 nm.

FIG. 17 shows distortions caused by an under-resolved step height in a scanning interference signals for pixels corresponding to various surface locations near the step height.

FIG. 18 shows nonlinear distortions in the frequency domain phase spectra for pixels corresponding to surface locations to the left (FIG. 18a) and the right (FIG. 18b) of the under-resolved step height in FIG. 17.

FIGS. 31a and 31b show the scanning interferometry signal for the center pixel in FIG. 30 and for x- and y-polarization, respectively.

Like reference numerals in different drawings refer to common elements.

DETAILED DESCRIPTION

Figure 1:
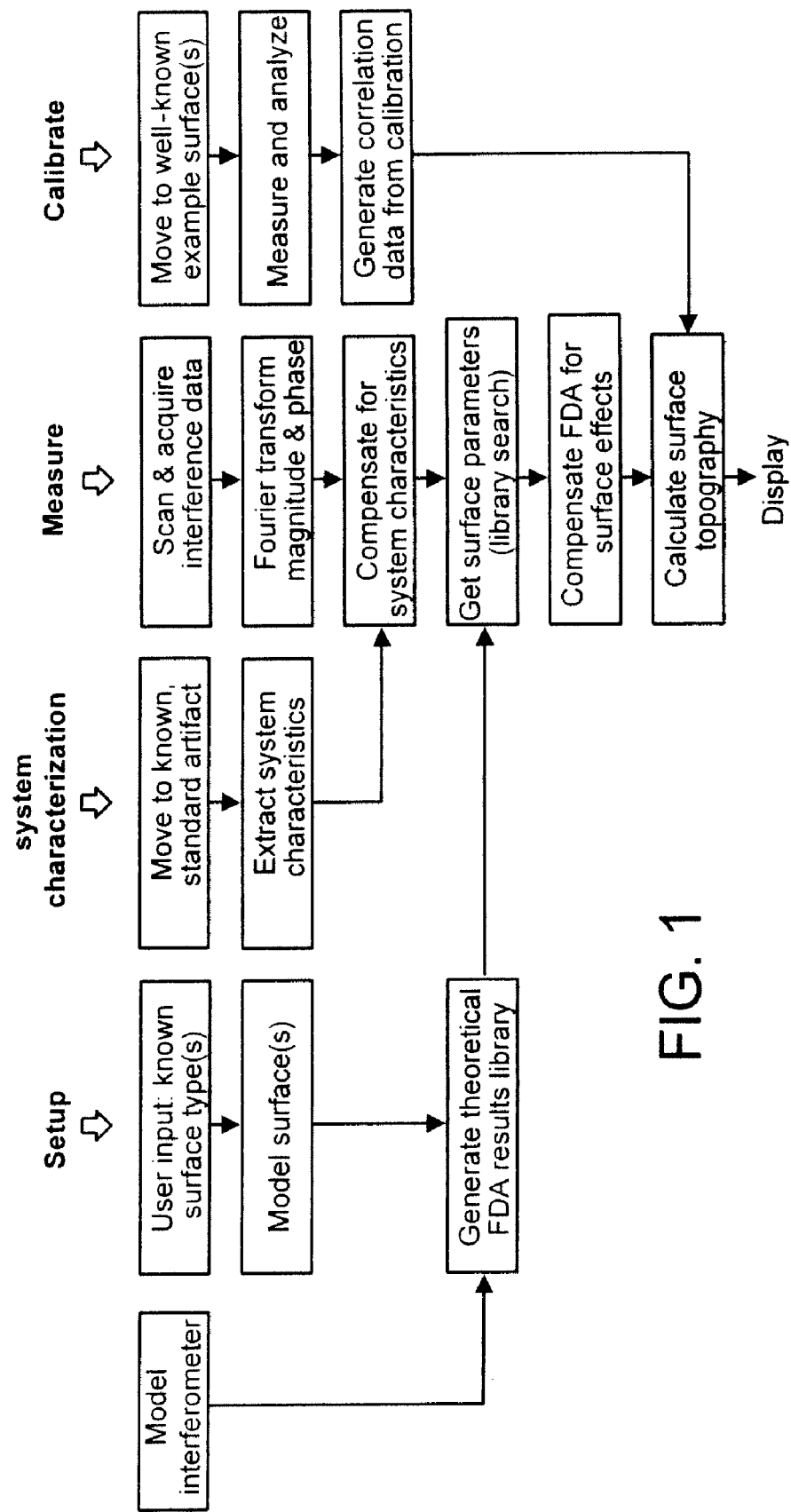
FIG. 1 is a flow chart of an interferometry method.

FIG. 1 shows a flow chart that generally describes one embodiment of the invention in which the analysis of the scanning interferometry data is performed in the spatial frequency domain.

Referring to FIG. 1, to measure data from a test object surface an interferometer is used to mechanically or electro-optically scan the optical path difference (OPD) between a reference and measurement path, the measurement path being directed to an object surface. The OPD at the beginning of the scan is a function of the local height of the object surface. A computer records an interference intensity signal during the OPD scan for each of multiple camera pixels corresponding to different surface locations of the object surface. Next, after storing interference intensity signal as a function of OPD scan position for each of the different surface locations, the computer performs a transform (e.g., a Fourier Transform) to generate a frequency-domain spectrum of the signal. The spectrum contains both magnitude and phase information as a function of the spatial frequency of the signal in the scanning dimension. For example, a suitable frequency domain analysis (FDA) for generating such a spectrum is disclosed in commonly owned U.S. Pat. No. 5,398,113 by Peter de Groot and entitled "Method and Apparatus for Surface Topography Measurements by Spatial-Frequency Analysis of Interferograms," the contents of which are incorporated herein by reference.

In a separate step, the computer generates a library of theoretical predictions for frequency-domain spectra for a variety of surface parameters and a model for the interferometer. These spectra may for example cover a range of possible thin film thicknesses, surface materials, and surface textures. In preferred embodiments, the computer generates library spectra for a constant surface height, e.g. height=zero. Thus, in such embodiments, the library contains no information regarding surface topography, only information relative to the type of surface structure and the interaction of this surface structure, the optical system, the illumination, and detection system when generating distinctive features of the frequency-domain spectra. As an alternative, the prediction library may be generated empirically, using sample artifacts. As another alternative, the library may use information from prior supplemental measurements of the object surface provided by other instruments, for example an ellipsometer, and any other input from a user regarding known properties of the object surface, so as to reduce the number of unknown surface parameters. Any of these techniques for library creation, theoretical modeling, empirical data, or theory augmented by supplemental measurements, may be expanded by interpolation to generate intermediate values, either as part of the library creation or in real time during a library search.

In a next step, the experimental data is compared to the prediction library by means of a library search that provides surface structure parameters. In the example case of a film of unknown thickness, the library for a single surface type, e.g. $SiO_2$ on Si, would range over many possible film thicknesses with the top surface height always equal to zero. Another example case would be surface roughness, for which the adjustable parameter may be roughness depth and/or spatial frequency. The library search leads to a match to those characteristics of the FDA spectra that are independent of surface height, for example, the average value of the magnitude spectrum, which is related to the overall reflectivity of the surface, or the variation in magnitude as a function of spatial frequency, which in a monochromatic high-NA system relates to the scattering angle of the reflected light.

The analysis may also include a system characterization, which includes, e.g. measuring one or more reference artifacts having a known surface structure and surface topography, so as to determine parameters such as system wavefront error, dispersion, and efficiency that may not be included in the theoretical model.

Furthermore, the analysis may include an overall calibration, which includes e.g., measuring one or more reference artifacts to determine the correlation between measured surface parameters, such as film thickness as determined by the library search, and the values for these parameters as determined independently, e.g. by ellipsometric analysis.

Based on the comparison of the experimental data to the prediction library, the computer identifies the surface model corresponding to the best match. It may then displays or transmits surface parameter results numerically or graphically to the user or to a host system for further analysis or for data storage. Using the surface parameter results, the computer may then determine surface height information in addition to characteristics identified by the library search. In some embodiments, the computer generates a compensated phase spectrum, for example by subtracting the corresponding theoretical phase spectrum directly from the experimental phase spectrum. The computer then determines the local surface height for one or more surface points by analysis of the compensated phase as a function of spatial frequency, for example by analysis of the coefficients generated by a linear fit. Thereafter, the computer generates a complete three-dimensional image constructed from the height data and corresponding image plane coordinates, together with graphical or numerical display of the surface characteristics as determined by the library search.

In some cases, the library search and data collection can be performed iteratively to further improve the results. Specifically, the library search can be refined on a pixel-by-pixel or regional basis, by the creation of refined libraries relevant to the local surface type. For example, if it is found that the surface has a thin film of approximately 1 micron during a preliminary library search, then the computer may generate a fine-grain library of example values close to 1 micron to further refine the search.

In further embodiments, the user may only be interested in the surface characteristics modeled by the prediction library, but not surface height, in which case the steps for determining surface height are not performed. Conversely, the user may only be interested in surface height, but not the surface characteristics modeled in the prediction library, in which case the computer uses the comparison between the experimental data and the prediction library to compensate the experimental data for the contributions of the surface characteristics, so that the surface height is more accurately determined, but need not explicitly determine the surface characteristics or display them.

The analysis may be applied to a variety of surface analysis problems, including: simple thin films (in which case, for example, the variable parameter of interest may be the film thickness, the refractive index of the film, the refractive index of the substrate, or some combination thereof); multilayer thin films; sharp edges and surface features that diffract or otherwise generate complex interference effects; unresolved surface roughness; unresolved surface features, for example, a sub-wavelength width groove on an otherwise smooth surface; dissimilar materials (for example, the surface may comprise a combination of thin film and a solid metal, in which case the library may include both surface structure types and automatically identify the film or the solid metal by a match to the corresponding frequency-domain spectra); optical activity such as fluorescence; spectroscopic properties of the surface, such as color and wavelength-dependent reflectivity; polarization-dependent properties of the surface; deflections, vibrations or motions of the surface or deformable surface features that result in perturbations of the interference signal; and data distortions related to the data acquisition procedure, e.g. a data acquisition window that does not fully encompass the interference intensity data.

The interferometer may include any of the following features: a spectrally narrow-band light source with a high numerical aperture (NA) objective; a spectrally broad band light source; a combination of a high NA objective and a spectrally broadband source; an interferometric microscope objectives, including oil/water immersion and solid immersion types, in e.g. Michelson, Mirau or Linnik geometries; a sequence of measurements at multiple wavelengths; unpolarized light; and polarized light, including linear, circular, or structured. For example, structured polarized light may involve, for example, a polarization mask, generating different polarizations for different segments of the illumination or imaging pupils, so as to reveal polarization-dependent optical effects attributable to surface characteristics. The interferometer may also include the overall system calibration, described above.

In comparing the theoretical and experimental data, the library search may be based on any of the following: a product of, or a difference between, magnitude and/or phase data in the frequency spectrum, including, e.g., the product of, or difference between, the average magnitude and the average phase, the average magnitude itself, and the average phase itself, the slope, width and/or height of the magnitude spectrum; interference contrast; data in the frequency spectrum at DC or zero spatial frequency; nonlinearity or shape of the magnitude spectrum; the zero-frequency intercept of the phase; nonlinearity or shape of the phase spectrum; and any combination of these criteria. Note that as used herein magnitude and amplitude are used interchangeably.

Figure 2:
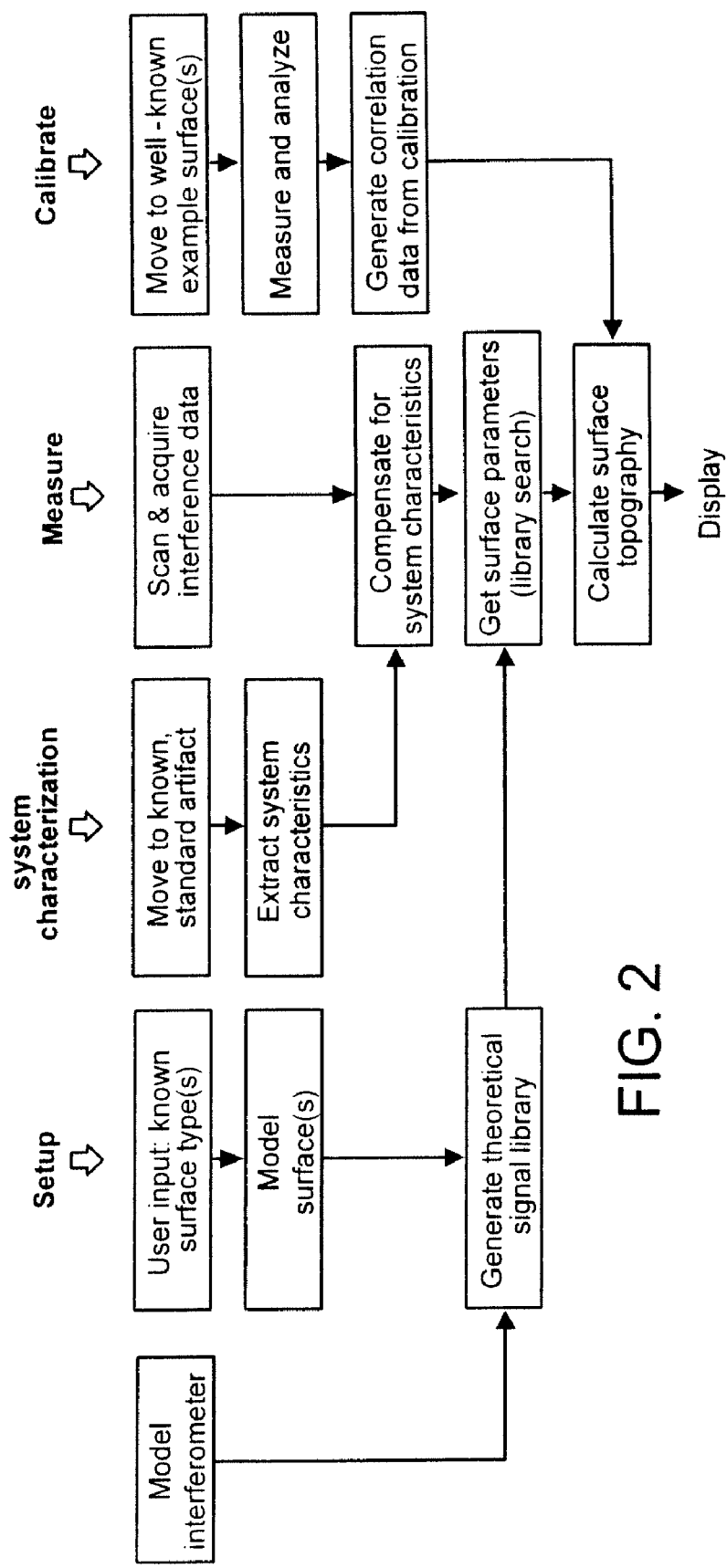
FIG. 2 is a flow chart showing a variation of the interferometry method of FIG. 1.

FIG. 2 shows a flow chart that generally describes another embodiment for the analysis of scanning interferometry data. The analysis is similar to that described for FIG. 1 except that comparison between the experimental data and the prediction library is based on information in scan coordinate domain. The experimental signal may be characterized by a quasi-periodic carrier oscillation modulated in amplitude by an envelope function with respect to the scan coordinate. In comparing the theoretical and experimental data, the library search may be based on any of the following: average signal strength; the shape of the signal envelope, including e.g. deviation from some ideal or reference shape such as a gaussian; the phase of the carrier signal with respect to the envelope function; the relative spacing of zero crossings and/or signal maxima and minima; values for maxima and minima and their ordering; peak value of the correlation between the library and measured signals, after adjusting for optimal relative scan position; and any combination of these criteria.

Furthermore, in additional embodiments, the information compared to the library models can be derived from experimental signals from multiple surface locations. This can be especially useful when the test object includes under-resolved surface features because the experimental information compared to the library models can correspond to a collective surface response of the test surface to interferometric measurement. For example, the information derived from the experimental signals from multiple surface locations can be a surface profile of the test surface obtained from conventional processing of the interferometry signals, or information derived from the surface profile. Such processing yield only apparent properties of the test surface because the under-resolved features will be obscured. Nonetheless, the under-resolved features can still leave signatures in the apparent surface profile that can be correlated to more accurate information about the under-resolved features by comparing the apparent properties to corresponding models of the test object that are parametrized by values characterizing the under-resolved features.

Moreover, the test object can also include certain reference structures that can be involved in the comparison of the apparent features to the library models. For example, when comparing the apparent surface height profile of a etched grating pattern whose individual lines are under-resolved to various models, a portion of the test object that is known to not be etched can provide a reference point for the apparent surface height in the grating portion of the test object.

Thus, in certain embodiments, an interferometric profiler having both a measurement and reference beam, for example a broadband or low coherence interferometer, is used to measure characteristics of a complex, unresolved surface structure such as may be found on a patterned semiconductor wafer. The profiler interprets variations in interference phase, contrast and/or surface reflectivity as variations in apparent measured surface height. In a separate step, data processing means calculate the expected response of the profile to possible variations in actual surface height and/or surface composition of the surface, including unresolved surface structures. Then, data processing means determine a true surface characteristic by comparing the apparent measured surface height to the expected response of the profiler to possible variations in actual surface height, unresolved surface structure and/or surface composition.

Figure 25:
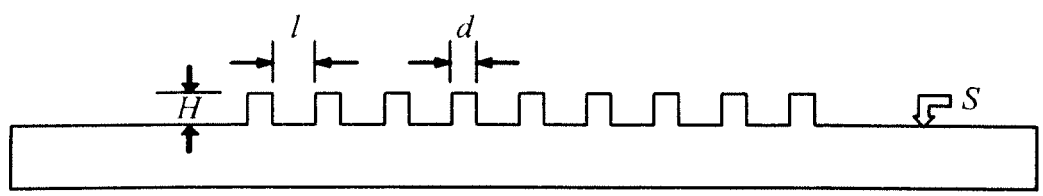
FIG. 25 is a schematic diagram of an object with under-resolved surface features (a grating pattern).

Prior to, during or after the data acquisition above, the data processor calculates the expected response of the instrument to possible variations in actual surface height and/or surface composition of the surface, including unresolved surface structures. FIG. 25 is an example of an object having unresolved surface features for visible-wavelength (400-700 nm wavelength) interferometry. Specifically, FIG. 25 shows array of elements (also referred to herein as a patterned structure or a grating structure). The unresolved surface features have a height H above an adjacent surface S, a separation l and a width d. The height H is also referred to herein as a modulation depth for the patterned structure. By "unresolved" it is meant that the individual features are not fully separated in the surface profile image, they have the incorrect profile and or the height H is incorrect, as a consequence of the limited lateral resolution of the instrument.

Figure 26:
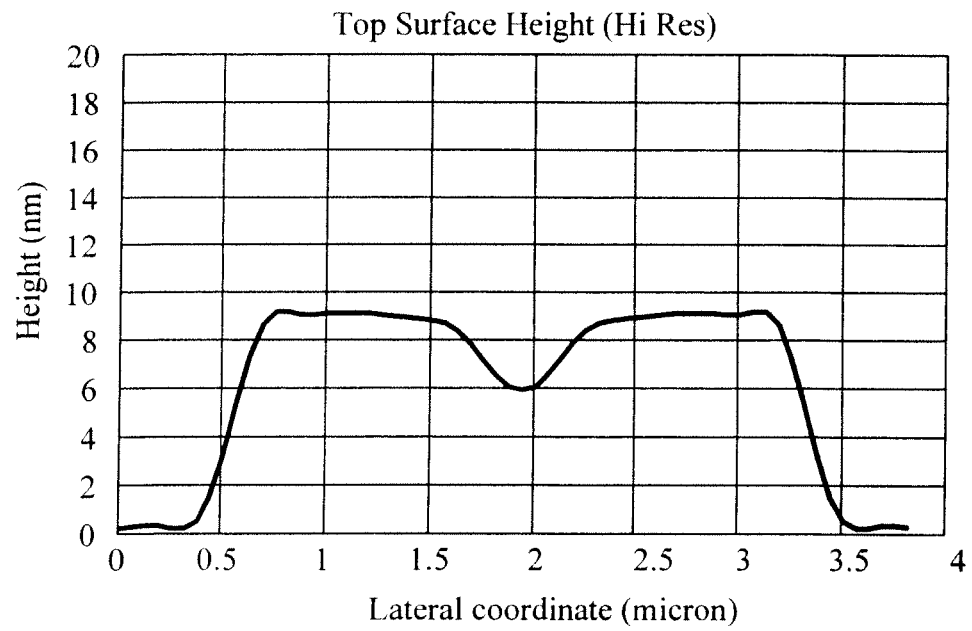
FIG. 26 is a graph of the predicted surface profile of the grating pattern in FIG. 25 based on a conventional interferometric analysis.
Figure 27:
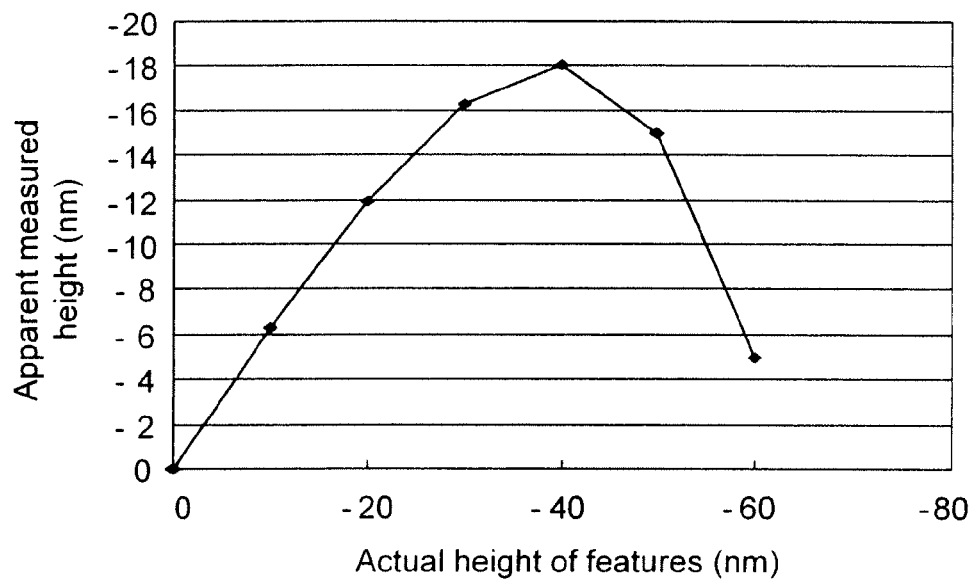
FIG. 27 is a graph of the apparent modulation depth of the grating in FIG. 25 for a conventional interferometric analysis as a function of its actual modulation depth.

FIG. 26 illustrates a predicted response for the unresolved features on the FIG. 25 object, for a visible-wavelength interferometer (560 nm center wavelength, 110 nm bandwidth full width half maximum) and an objective NA of 0.8, using the Rayleigh Hypothesis technique (described further below). The surface structures are unresolved, resulting in an apparent measured surface profile that does not resemble at all the actual surface structure. For this calculation, the height H=20 nm, the separation I=200 nm and a width d=120 nm. FIG. 27 shows how the unresolved measured profile of FIG. 26 as a function of the actual height H of the features. Noteworthy is that the relationship between the measured and true height is complicated and even negatively correlated above 40 nm. This latter phenomenon can be explained as the difficulty in coupling light into the narrow, sub-wavelength trenches After data acquisition and after calculating the expected system response, the data processor determines a true surface characteristic by comparing the apparent measured surface height to the expected response of the inventive apparatus to possible variations in actual surface height, unresolved surface structure and/or surface composition. Following the example of FIG. 25 through FIG. 27, this involves determining the relationship between the actual height H and the apparent measured height, as shown in FIG. 27, and determining the actual height from the measurement result using knowledge of this relationship. Alternative measurement modalities, such as determining the width d and separation l. As discussed further below, polarizing the objective can also increase sensitivity to specific parameters such as etch depth, as can using an alternative light source to change the illumination wavelength and thereby adjust the sensitivity range.

Many processing techniques can be used to extract the apparent property or properties (e.g., apparent surface profile) from the scanning interferometry data. For example, conventional techniques include identifying, for each pixel, the position corresponding to the peak or center of the fringe contrast envelope or to use, for each pixel, frequency domain analysis (FDA) and associate the rate of change of phase with wavelength as directly proportional to surface height (see, for example, U.S. Pat. No. 5,398,133). In addition, it is also possible to use more advanced processing techniques that try to remove thin film effects from the interferometry signals, such as disclosed in U.S. Patent Publication No. US-2005-0078318-A1 entitled "METHODS AND SYSTEMS FOR INTERFEROMETRIC ANALYSIS OF SURFACES AND RELATED APPLICATIONS," by Peter de Groot or commonly owned U.S. patent application Ser. No. 11/437,002 entitled "METHOD AND SYSTEM FOR ANALYZING LOW-COHERENCE INTERFEROMETRY SIGNALS FOR INFORMATION ABOUT THIN FILM STRUCTURES" by Peter de Groot and filed May 18, 2006, the contents of both applications being incorporated herein by reference. Of course, the model library used for comparison should take into account the processing technique used to extract the experimentally derived information. In what follows we provide a detailed mathematical description of the analyses and provide examples. First, we describe exemplary scanning interferometers. Second, we determine a mathematical model for scanning interferometry data. Third, we describe optical properties of surfaces and how to use such information to generate accurate models of scanning interferometry data for different surface characteristics. Fourth, we describe how experimental interferometry data can be compared to the prediction library to provide information about the test object. Initially, we will describe thin film applications, and later we will describe applications to other complex surface structures, specifically, optically under-resolved step heights and grating patterns. Also, we will initially focus on analyses in the spatial frequency domain, and later we will describe analyses in the scan coordinate domain. Thereafter, we will describe additional examples of techniques for extracting information about under-resolved surface features from the interferometry signals such as in the example of FIGS. 25-27 above.

Figure 3:
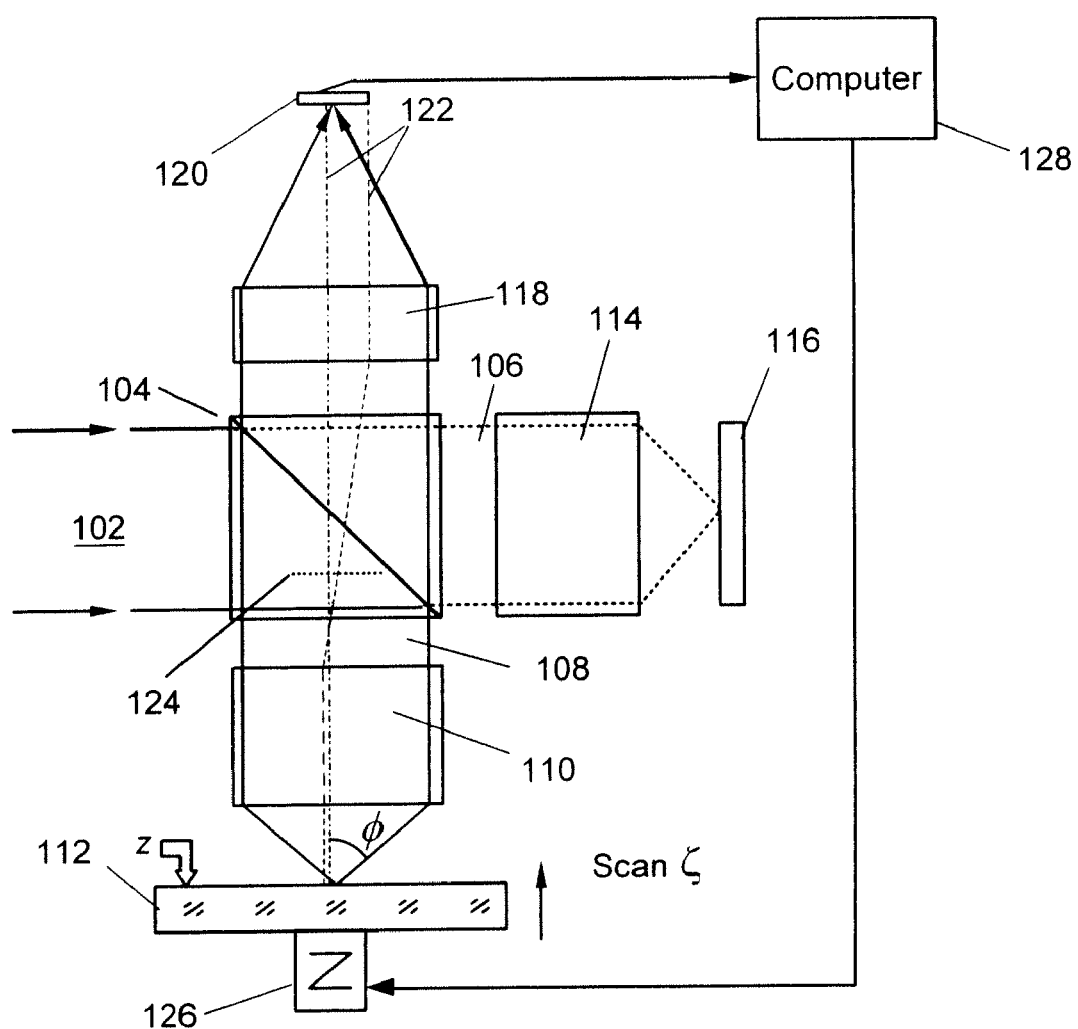
FIG. 3 is a schematic drawing of a Linnik-type scanning interferometer.

FIG. 3 shows a scanning interferometer of the Linnik type. Illumination light 102 from a source (not shown) is partially transmitted by a beam splitter 104 to define reference light 106 and partially reflected by beam splitter 104 to define measurement light 108. The measurement light is focused by a measurement objective 110 onto a test sample 112 (e.g., a sample comprising a thin single- or multi-layer film of one or more dissimilar materials). Similarly, the reference light is focused by a reference objective 114 onto a reference mirror 116. Preferably, the measurement and reference objectives have common optical properties (e.g., matched numerical apertures). Measurement light reflected (or scattered or diffracted) from the test sample 112 propagates back through measurement objective 110, is transmitted by beam splitter 104, and imaged by imaging lens 118 onto a detector 120. Similarly, reference light reflected from reference mirror 116 propagates back through reference objective 114, is reflected by beam splitter 104, and imaged by imaging lens 118 onto a detector 120, where it interferes with the measurement light.

For simplicity, FIG. 3 shows the measurement and reference light focusing onto particular points on the test sample and reference mirror, respectively, and subsequently interfering on a corresponding point on the detector. Such light corresponds to those portions of the illumination light that propagate perpendicular to the pupil planes for the measurement and reference legs of the interferometer. Other portions of the illumination light ultimately illuminate other points on the test sample and reference mirror, which are then imaged onto corresponding points on the detector. In FIG. 3, this is illustrated by the dashed lines 122, which correspond to the chief rays emerging from different points on the test sample that are imaged to corresponding points on the detector. The chief rays intersect in the center of the pupil plane 124 of the measurement leg, which is the back focal plane of measurement objective 110. Light emerging from the test sample at an angle different from that of the chief rays intersect at a different location of pupil plane 124.

In preferred embodiments, detector 120 is a multiple element (i.e., multi-pixel) camera to independently measure the interference between the measurement and reference light corresponding to different points on the test sample and reference mirror (i.e., to provide spatial resolution for the interference pattern).

A scanning stage 126 coupled to test sample 112 scans the position of the test sample relative to measurement objective 110, as denoted by the scan coordinate $\zeta$ in FIG. 3. For example, the scanning stage can be based on a piezoelectric transducer (PZT). Detector 120 measures the intensity of the optical interference at one or more pixels of the detector as the relative position of the test sample is being scanned and sends that information to a computer 128 for analysis.

Because the scanning occurs in a region where the measurement light is being focused onto the test sample, the scan varies the optical path length of the measurement light from the source to the detector differently depending on the angle of the measurement light incident on, and emerging from, the test sample. As a result, the optical path difference (OPD) from the source to the detector between interfering portions of the measurement and reference light scale differently with the scan coordinate $\zeta$ depending on the angle of the measurement light incident on, and emerging from, the test sample. In other embodiments of the invention, the same result can be achieved by scanning the position of reference mirror 116 relative to reference objective 114 (instead of scanning test sample 112 relative to measurement objective 110).

This difference in how OPD varies with the scan coordinate $\zeta$ introduces a limited coherence length in the interference signal measured at each pixel of the detector. For example, the interference signal (as a function of scan coordinate) is typically modulated by an envelope having a spatial coherence length on the order of $\lambda/2 \, (NA)^2$, where $\lambda$ is the nominal wavelength of the illumination light and NA is the numerical aperture of the measurement and reference objectives. As described further below, the modulation of the interference signal provides angle-dependent information about the reflectivity of the test sample. To increase the limited spatial coherence, the objectives in the scanning interferometer preferably define a large numerical aperture, e.g., greater than about 0.7 (or more preferably, greater than about 0.8, or greater than about 0.9). The interference signal can also be modulated by a limited temporal coherence length associated with the spectral bandwidth of the illumination source. Depending on the configuration of the interferometer, one or the other of these limited coherence length effects may dominate, or they may both contribute substantially to the overall coherence length.

Figure 4:
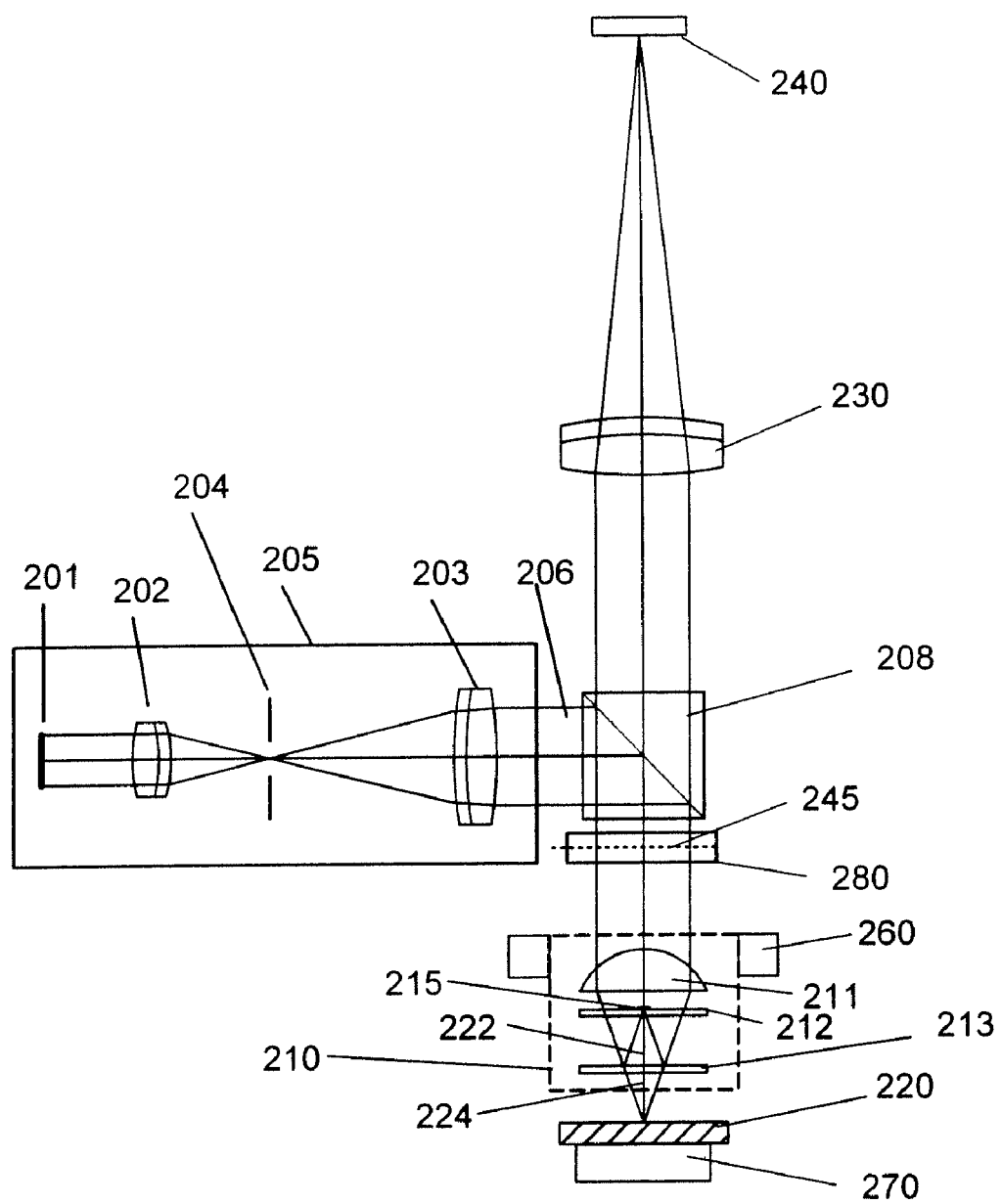
FIG. 4 is a schematic drawing of a Mirau-type scanning interferometer.

Another example of a scanning interferometer is the Mirau-type interferometer shown in FIG. 4.

Referring to FIG. 4, a source module 205 provides illumination light 206 to a beam splitter 208, which directs it to a Mirau interferometric objective assembly 210. Assembly 210 includes an objective lens 211, a reference flat 212 having a reflective coating on a small central portion thereof defining a reference mirror 215, and a beam splitter 213. During operation, objective lens 211 focuses the illumination light towards a test sample 220 through reference flat 212. Beam splitter 213 reflects a first portion of the focusing light to reference mirror 215 to define reference light 222 and transmits a second portion of the focusing light to test sample 220 to define measurement light 224. Then, beam splitter 213 recombines the measurement light reflected (or scattered) from test sample 220 with reference light reflected from reference mirror 215, and objective 211 and imaging lens 230 image the combined light to interfere on detector (e.g., a multi-pixel camera) 240. As in the system of FIG. 3, the measurement signal(s) from the detector is sent to a computer (not shown).

The scanning in the embodiment of FIG. 4 involves a piezoelectric transducer (PZT) 260 coupled to Mirau interferometric objective assembly 210, which is configured to scan assembly 210 as a whole relative to test sample 220 along the optical axis of objective 211 to provide the scanning interferometry data $I(\zeta,h)$ at each pixel of the camera. Alternatively, the PZT may be coupled to the test sample rather than assembly 210 to provide the relative motion there between, as indicated by PZT actuator 270. In yet further embodiments, the scanning may be provided by moving one or both of reference mirror 215 and beam splitter 213 relative to objective 211 along the optical axis of objective 211.

Source module 205 includes a spatially extended source 201, a telescope formed by lenses 202 and 203, and a stop 204 positioned in the front focal plane of lens 202 (which coincides with the back focal plane of lens 203). This arrangement images the spatially extended to source onto the pupil plane 245 of Mirau interferometric objective assembly 210, which is an example of Koehler imaging. The size of stop controls the size of the illumination field on test sample 220. The system can also include an aperture stop (not shown) positioned between beam splitter 208 and interference objective assembly 210. In other embodiments, the source module may include an arrangement in which a spatially extended source is imaged directly onto the test sample, which is known as critical imaging. Either type of source module may be used with the Linnik-type scanning interferometry system of FIG. 3.

In further embodiments of the invention, the scanning interferometry system may used to determine angle-dependent scattering or diffraction information about a test sample, i.e., for scatterometry. For example, the scanning interferometry system may be used to illuminate a test sample with test incident over only a very narrow range of incident angles (e.g., substantially normal incidence or otherwise collimated), which may then be scattered or diffracted by the test sample. The light emerging from the sample is imaged to a camera to interfere with reference light as described above. The spatial frequency of each component in the scanning interferometry signal will depend vary with angle of the test light emerging from the test sample. Thus, a vertical scan (i.e., a scan along the optical axis of an objective) followed by Fourier analysis allows for a measurement of diffracted and/or scattered light as a function of emerging angle, without directly accessing or imaging the back focal plane of the objective. To provide the substantially normal incidence illumination, for example, the source module can be configured to image a point source onto the pupil plane or to otherwise decrease the degree to which the illumination light fills the numerical aperture of the measurement objective. The scatterometry technique may be useful for resolving discrete structures in the sample surface, such as grating lines, edges, or general surface roughness, which may diffract and/or scatter light to higher angles.

In much of the analysis herein, it is assumed that the polarization state of the light in the pupil plane is random, i.e., comprised of approximately equal amounts of both s polarizations (orthogonal to the plane of incidence) and p (orthogonal to the plane of incidence) polarizations. Alternative polarizations are possible, including pure s polarization, such as may be realized by means of a radial polarizer placed in the pupil plane (e.g., in the back-focal plane of the measurement object in the case of a Linnik interferometer and in the back focal plane of the common objective in the Mirau interferometer). Other possible polarizations include radial p polarization, circular polarization, and modulated (e.g. two states, one following the other) polarization for ellipsometric measurements. In other words, optical properties of the test sample can be resolved not only with respect to their angle- or wavelength-dependence, but also with respect to their polarization dependence or with respect to a selected polarization. Such information may also be used to improve the accuracy of thin film structure characterization.

To provide such ellipsometry measurements, the scanning interferometry system may include a fixed or variable polarizer in the pupil plane. Referring again to FIG. 4, the Mirau-type interferometry system, for example, includes polarization optics 280 in the pupil plane to select a desired polarization for the light incident on, and emerging from the test sample. Furthermore, the polarization optics may be reconfigurable to vary the selected polarization. The polarization optics may include one or more elements including polarizers, waveplates, apodization apertures, and/or modulation elements for selecting a given polarization. Furthermore, the polarization optics may be fixed, structured or reconfigurable, for the purpose of generating data similar to that of an ellipsometer. For example, a first measurement with a radially-polarized pupil for s polarization, followed by a radially-polarized pupil for p polarization. In another example, one may use an apodized pupil plane with linearly polarized light, e.g., a slit or wedge, which can be rotated in the pupil plane so as to direct any desired linear polarization state to the object, or a reconfigurable screen such as a liquid crystal display.

Moreover, the polarization optics may provide a variable polarization across the pupil plane (e.g., by including multiple polarizers or a spatial modulator). Thus, one can "tag" the polarization state according to spatial frequency, for example, by providing a different polarization for high angles of incidence than shallow angles.

In yet further embodiments, the selectable polarization may be combined with a phase shift as a function of polarization. For example, the polarization optics may include a linear polarizer is positioned in the pupil plane and followed by two waveplates (e.g., eighth-wave plates) in opposing quadrants of the pupil plane. The linear polarization results in a full range of polarization angles with respect to the incident planes of the objective. If the waveplates are aligned so that, for example, the predominately s-polarized light has a fixed phase shift, then both radial s polarized and p polarized light are present simultaneously, but shifted in phase with respect to each other, e.g., by pi, so that the interferometer is effectively detecting the difference between these two polarization states as the fundamental signal.

In further embodiments, polarization optics may be positioned elsewhere in the apparatus. For example, linear polarization can be achieved anywhere in the system.

We now describe a physical model for the scanning interferometry signal.

The object surface has height features h which we wish to profile over an area indexed by lateral coordinates x,y. The stage provides a smooth, continuous scan $\zeta$ neither of the interference objective or, as shown, of the object itself. During the scan, a computer records intensity data $I_{\zeta,h}$ for each image point or camera pixel in successive camera frames. Note that the key dependencies of the intensity $I_{\zeta,h}$ on the scan position and surface height are indicated by subscripts—a notation that we shall employ throughout.

A proper physical model of the optics can be very elaborate, taking into account the partial coherence of the light source, polarization mixing in the interferometer, the imaging properties of high-NA objectives, and the interaction of electric field vectors at high angles of incidence and in the presence of discontinuous surface features.

For example, to rigorously predict the interferometer signal from a given structure requires solving Maxwell's Equations for that structure. White light interferometry requires a sufficiently dense set of wavelengths covering the bandwidth of the illumination. There are many approaches to solving Maxwell's Equations in 2D. In 2D one particularly simple approach is based on the Rayleigh Hypothesis. In this approach the structure is treated as a thin film stack but with the interfaces between each layer in the stack having a specific topography. The Rayleigh Hypothesis states that within each layer the electromagnetic field can be expanded in upward and downward propagating plane waves and the solution can be generated by choosing the coefficients so that the electromagnetic field satisfies the standard boundary conditions at the interfaces. This approach is easy to implement, relatively fast and it generates the full optical transfer function or scattering matrix of the surface at one wavelength and for one polarization in a single computation. A limitation is that it generates valid solutions only in cases where the topography of each interface covers less than roughly half the wavelength in the layers bounding the interface. Hence, high index materials such as silicon restrict the topography at visible wavelengths to be much less than 100 nm.

3D modeling techniques include Finite Difference Time Domain (FDTD), Finite Element and rigorous coupled-wave analysis (RCWA). See, e.g., M. G. Moharam and T. K. Gaylord, "Diffraction analysis of dielectric surface-relief gratings." J. Opt. Soc. Am., 72, 1385-1392, (1982), and M. Totzeck, "Numerical simulation of high-NA quantitative polarization microscopy and corresponding near-fields", Optik, 112 (2001) 381-390. Moreover, the Institute of Technical Optics (ITO) at the University of Stuttgart has developed software for performing RCWA called Microsim, based on the work of M. Totzek. These techniques are powerful although often limited to small volumes, i.e., a few wavelengths on a side, to keep both the memory requirements and the runtimes reasonable. Nonetheless, because such techniques can be used in advance to generate suitable libraries, extensive computation time used to generate the libraries does not hinder in-process application of the techniques disclosed herein.

Figure 5:
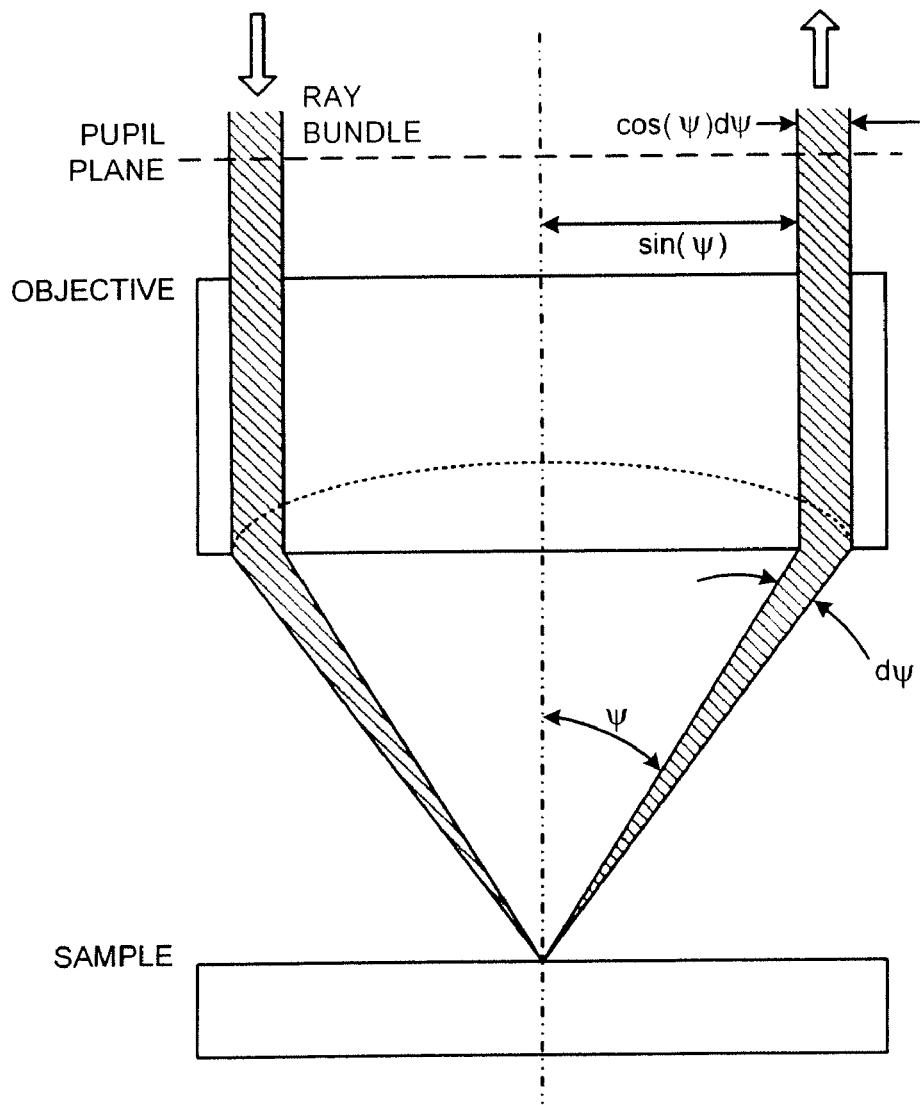
FIG. 5 is a diagram showing illumination of the test sample through an objective lens.

For convenience, and to demonstrate certain aspects of the invention, we simplify the model by assuming random polarization and diffuse, low-coherence extended sources. Modeling the interference signal simplifies to adding up the contributions of all of the ray bundles passing through the pupil plane of the objective and reflecting from the object surface at an incident angle $\psi$, as shown in FIG. 5.

The interference contribution for a single ray bundle through the optical system is proportional to $$g_{\beta,k,\zeta,h} = R_{\beta,k} + Z_{\beta,k} + 2\sqrt{R_{\beta,k} Z_{\beta,k}} \cos[2\beta k n_0(h-\zeta) + (\upsilon_{\beta,k} - \omega_{\beta,k})]. \quad (1)$$

Where $Z_{\beta,k}$ is the effective object intensity reflectivity, including e.g. the effects of the beamsplitter, and $R_{\beta,k}$ is the effective reference reflectivity, including both the beamsplitter and the reference mirror. The index of the ambient medium is $n_0$, the directional cosine for an incident angle $\psi$ is $$\beta = \cos(\psi) \quad (2)$$

and the wavenumber for the source illumination is $$k = (2\pi/\lambda) \quad (3)$$

The sign convention for the phase causes an increase in surface height to correspond to a positive change in phase. The phase term has a contribution $\omega_{\beta,k}$ for the object path in the interferometer, including thin film effects from the object surface, and a contribution $\upsilon_{\beta,k}$ for the reference path, including the reference mirror and other optics in the objective.

The total interference signal integrated over the pupil plane is proportional to $$I_{\zeta,h} = \int_0^\infty \int_0^1 g_{\beta,k,\zeta,h} U_\beta V_k \beta \, d\beta \, dk \quad (4)$$

where $U_\beta$ is the pupil plane light distribution and $V_k$ the optical spectrum distribution. The weighting factor $\beta$ in Eq. (4) follows from a $\cos(\psi)$ term attributable to the projection angle and a $\sin(\psi)$ term for the diameter of the annulus of width $d\psi$ in the pupil plane:

$$\cos(\psi)\sin(\psi)d\psi = -\beta d\beta \quad (5)$$

Here we assume that the objective obeys the Abbé sine condition as shown in FIG. 5. This relatively simple weighting is possible for randomly polarized, spatially incoherent illumination, for which all ray bundles are independent from each other. Finally, the integration limits over all incident angles implies $0 \leq \beta \leq 1$ and the spectrum integration over all wavenumbers $0 \leq k \leq \infty$.

In a frequency domain analysis (FDA), we first calculate the Fourier Transform of the interference intensity signal $I_{\zeta,h}$. For the literal (non-numerical) analysis we shall use the unnormalized Fourier integral $$q_{K,h} = \int_{-\infty}^{\infty} I_{\zeta,h} \exp(iK\zeta) d\zeta \quad (6)$$

where K is the spatial frequency, e.g. in cycles per µm. The frequency-domain value $q_{K,h}$ carries units of inverse wavenumber, e.g. µm. From this there follows a power spectrum $$Q_{K,h} = |q_{K,h}|^2 \quad (7)$$

and a phase spectrum $$\phi_{K,h}'' = \arg(q_{K,h}). \quad (8)$$

The double prime for $\phi_{K,h}''$ means that there is a two-fold uncertainty in the fringe order, both from pixel to pixel and overall with respect to the starting point in the scan. Conventional FDA then proceeds directly to a determination of surface topography by a linear fit to the phase spectrum $\phi_{K,h}''$ weighted by the power spectrum $Q_{K,h}$. The fit provides for each pixel a slope $$\sigma_h \approx d\phi''/dK \quad (9)$$

and an intercept $$A'' \approx \phi_{K=0,h}''. \quad (10)$$

Note that the intercept or "phase gap" A" is independent of height h, but carries the double prime inherited from the fringe order uncertainty in the phase data. The slope σ is free of this uncertainty. From the intercept A" and the slope $\sigma_h$, we can define for a specific mean or nominal spatial frequency K0 a "coherence profile"

$$\Theta_h = \sigma_h K0 \quad (11)$$

and a "phase profile"

$$\theta_h'' = \Theta_h + A''. \quad (12)$$

For the simple, idealized case of a perfectly uniform, homogeneous dielectric surface free of thin films and dissimilar material effects, and an optical system perfectly balanced for dispersion, the phase and coherence profiles are linearly proportional to surface height:

$$h_\Theta = \Theta_h/K0 \quad (13)$$

$$h_\theta'' = \theta_h''/K0 \quad (14)$$

Of the two height calculations, the height value $h_\theta''$ based on phase is the more accurate, but it has the uncertainty in the fringe order characteristic of monochromatic interferometry. For high resolution, we can use the unambiguous but less precise height value $h_\Theta$ based on coherence to remove this uncertainty and yield a final value $h_\theta$.

Conventional FDA assumes that even for less idealized situations, the interference phase $\phi_{K,h}''$ is still nearly a linear function of spatial frequency. This corresponds to conventional FDA processing of the scanning interferometry signal to get surface height. For the present embodiment, however, we determine key parameters of the surface structure such as film thickness by comparing experimental data to a theoretical prediction that may include highly nonlinear phase spectra and associated modulations of the power spectrum.

To this end, we combine the definition of the Fourier Transform Eq. (6) with the interference signal Eq. (4) into the following formula for the predicted FDA spectrum:

$$q_{K,h} = \int_{-\infty}^{\infty} \int_0^{\infty} \int_0^1 g_{\beta,k,\zeta,h} \exp(iK\zeta) U_\beta V_k \beta \, d\beta \, dk \, d\zeta \qquad (15)$$

To improve computational efficiency, a partial literal evaluation of the triple integration in Eq. (15) can be performed.

The literal analysis of Eq. (15) begins with a change of the order of integration to first evaluate the individual interference signals $g_{\beta,k,\zeta,h}$ over all scan positions $\zeta$ at fixed $\beta$ and $k$:

$$q_{K,h} = \int_0^{\infty} \int_0^1 U_\beta V_k \beta \left\{ \int_{-\infty}^{\infty} g_{\beta,k,\zeta,h} \exp(iK\zeta) \, d\zeta \right\} d\beta \, dk. \qquad (16)$$

After expansion of the cosine term in $g_{\beta,k,\zeta,h}$ in the usual way using $$2\cos(u) = \exp(iu) + \exp(-iu), \qquad (17)$$

the inner integral over $\zeta$ evaluates to $$\int_{-\infty}^{\infty} g_{\beta,k,\zeta,h} \exp(iK\zeta) \, d\zeta = \delta_K (R_{\beta,k} + Z_{\beta,k}) \ldots + \qquad (18)$$
$$\delta_{(K-2\beta k n_0)} \sqrt{R_{\beta,k} Z_{\beta,k}} \exp[i 2\beta k n_0 h + i(v_{\beta,k} - \omega_{\beta,k})] \ldots +$$
$$\delta_{(K+2\beta k n_0)} \sqrt{R_{\beta,k} Z_{\beta,k}} \exp[-i 2\beta k n_0 h - i(v_{\beta,k} - \omega_{\beta,k})]$$

where we have used $$\delta_K = \int_{-\infty}^{\infty} \exp(iK\zeta) \, d\zeta \qquad (19)$$

$$\delta_{(K \pm 2\beta k n_0)} = \int_{-\infty}^{\infty} \exp(iK\zeta) \exp(\pm i 2\beta k n_0 \zeta) \, d\zeta. \qquad (20)$$

The $\delta$ function carries with it the inverse physical units of the argument, in this case, an inverse wavenumber.

These delta functions validate an equivalency between the spatial frequency $K$ and the product $2\beta k n_0$. A logical change of variables for the next integration is therefore $$\beta = \hat{\kappa}/2k n_0 \qquad (21)$$

$$d\beta = d\hat{\kappa}/2k n_0 \qquad (22)$$

where $\hat{\kappa}$ has the same meaning as the spatial frequency $K$, but will be used as a free integration variable. Eq. (18) can be written $$q_{K,h} = \int_0^{\infty} \int_0^{2kn_0} \delta_K (R_{\hat{\kappa},k} + Z_{\hat{\kappa},k}) \Gamma_{\hat{\kappa},k} \, d\hat{\kappa} \, dk \ldots + \qquad (23)$$
$$\int_0^{\infty} \int_0^{2kn_0} \delta_{(K-\hat{\kappa})} \sqrt{R_{\hat{\kappa},k} Z_{\hat{\kappa},k}}$$
$$\exp[i\hat{\kappa} h + i(v_{\hat{\kappa},k} - \omega_{\hat{\kappa},k})] \Gamma_{\hat{\kappa},k} \, d\hat{\kappa} \, dk \ldots +$$
$$\int_0^{\infty} \int_0^{2kn_0} \delta_{(K+\hat{\kappa})} \sqrt{R_{\hat{\kappa},k} Z_{\hat{\kappa},k}} \exp[-i\hat{\kappa} h - i(v_{\hat{\kappa},k} - \omega_{\hat{\kappa},k})] \Gamma_{\hat{\kappa},k} \, d\hat{\kappa} \, dk$$

where $$\Gamma_{\hat{\kappa},k} = \frac{U_{\hat{\kappa},k} V_k \hat{\kappa}}{4k^2 n_0^2}. \qquad (24)$$

Note that by virtue of the change in variables, the $\beta$-dependence for the R, Z, $\upsilon$, $\omega$ terms in Eq. (23) becomes a dependence upon $\hat{\kappa}$ and $k$.

For the next step, we first note that $$\int_0^{2kn_0} \delta_K f_{\hat{\kappa},k} \, d\hat{\kappa} = \delta_K \int_0^{\infty} H_{(2kn_0 - \hat{\kappa})} f_{\hat{\kappa},k} \, d\hat{\kappa} \qquad (25)$$

$$\int_0^{2kn_0} \delta_{(K-\hat{\kappa})} f_{\hat{\kappa},k} \, d\hat{\kappa} = f_{K,k} H_K H_{(2kn_0 - K)} \qquad (26)$$

$$\int_0^{2kn_0} \delta_{(K+\hat{\kappa})} f_{\hat{\kappa},k} \, d\hat{\kappa} = f_{-K,k} H_{-K} H_{(2kn_0 + K)} \qquad (27)$$

where H is the unitless Heaviside step function defined by $$H_u = \begin{cases} 0 & \text{for } u < 0 \\ 1 & \text{otherwise} \end{cases} \qquad (28)$$

and f is an arbitrary function of K and k. Using Eqs. (25) through (27), Eq. (23) becomes $$q_{K,h} = \delta_K \int_0^{\infty} \int_0^{\infty} H_{(2kn_0 - \hat{\kappa})} (R_{\hat{\kappa},k} + Z_{\hat{\kappa},k}) \Gamma_{\hat{\kappa},k} \, d\hat{\kappa} \, dk \ldots + \qquad (29)$$
$$\int_0^{\infty} H_K H_{(2kn_0 - K)} \sqrt{R_{K,k} Z_{K,k}} \exp[iKh + i(v_{K,k} - \omega_{K,k})]$$
$$\Gamma_{K,k} dk \ldots + \int_0^{\infty} H_{-K} H_{(2kn_0 + K)} \sqrt{R_{-K,k} Z_{-K,k}}$$
$$\exp[iKh - i(v_{-K,k} - \omega_{-K,k})] \Gamma_{-K,k} dk$$

Now using $$\int_0^{\infty} \int_0^{\infty} H_{(2kn_0 - \hat{\kappa})} f_{\hat{\kappa},k} \, d\hat{\kappa} \, dk = \int_0^{\infty} \int_0^{\infty} H_{(2kn_0 - \hat{\kappa})} f_{\hat{\kappa},k} \, dk \, d\hat{\kappa} \qquad (30)$$

$$\int_0^{\infty} H_K H_{(2kn_0 - K)} f_{K,k} \, dk = H_K \int_{K/2n_0}^{\infty} f_{K,k} \, dk \qquad (31)$$

$$\int_0^{\infty} H_{-K} H_{(2kn_0 + K)} f_{-K,k} \, dk = H_{-K} \int_{-K/2n_0}^{\infty} f_{-K,k} \, dk \qquad (32)$$

we have the final result $$q_{K,h} = \delta_K \int_{k=0}^{\infty} \int_{K/2n_0}^{\infty} (R_{\kappa,k} + Z_{\kappa,k}) \Gamma_{\hat{\kappa},k} \, dk \, d\hat{\kappa} + \qquad (33)$$

$$H_K \exp(iKh) \int_{K/2n_0}^{\infty} \sqrt{R_{K,k} Z_{K,k}} \exp[i(\upsilon_{K,k} - \omega_{K,k})] \Gamma_{K,k} \, dk \ldots +$$

$$H_{-K} \exp(iKh) \int_{-K/2n_0}^{\infty} \sqrt{R_{-K,k} Z_{-K,k}} \exp[-i(\upsilon_{K,k} - \omega_{-K,k})] \Gamma_{-K,k} \, dk.$$

Because there are fewer integrations, Eq. (33) is significantly more efficient computationally that the original triple integral of (15).

Some limit cases are interesting to solve analytically. For example, if the phase contribution $(\upsilon_{K,k} - \omega_{K,k}) = 0$ and the reflectivities R, Z are independent of incident angle and wavelength, then Eq. (33) simplifies to $$q_{K,h} = \qquad (34)$$

$$\delta_K (R+Z) \int_0^{\infty} \int_{R/2n_0}^{\infty} \Gamma_{\hat{\kappa},k} \, dk \, d\hat{\kappa} + H_K \exp(iKh) \sqrt{RZ} \int_{K/2n_0}^{\infty} \Gamma_{K,k} \, dk +$$

$$H_{-K} \exp(iKh) \sqrt{RZ} \int_{-K/2n_0}^{\infty} \Gamma_{-K,k} \, dk$$

and we have only to handle integrals involving the weighting factor $\Gamma_{K,k}$ defined in Eq. (24). This idealized case simplifies evaluation of two further limit cases for Eq. (34): Near-monochromatic illumination with a high-NA objective, and broadband illumination with low-NA.

For the case of a near-monochromatic light source having a narrow spectral bandwidth $k_\Delta$, we have the normalized spectrum $$V_k = \frac{1}{k_\Delta} H_{(k-k0)} H_{(k0+k_\Delta-k)} \qquad (35)$$

where k0 is the nominal source wavenumber. The integrations in Eq. (34) are now of the form:

$$\int_0^{\infty} \int_{K/2n_0}^{\infty} \Gamma_{\hat{\kappa},k} \, dk \, d\hat{\kappa} = \frac{1}{4n_0^2 k_\Delta} \int_0^{\infty} H_{(k0-\hat{\kappa}/2n_0)} \hat{\kappa} \int_{k0}^{k0-k_\Delta} \frac{U_{\hat{\kappa},k}}{k^2} \, dk \, d\hat{\kappa} \qquad (36)$$

$$\int_{K/2n_0}^{\infty} \Gamma_{K,k} \, dk = \frac{1}{4n_0^2 k_\Delta} H_{(k0-K/2n_0)} K \int_{k0}^{k0+k_\Delta} \frac{U_{K,k}}{k^2} \, dk. \qquad (37)$$

Assuming that $U_{K,k}$ is essentially constant over the small bandwidth $k_\Delta$, we have $$\int_0^{\infty} \int_{K/2n_0}^{\infty} \Gamma_{\hat{\kappa},k} \, dk \, d\hat{\kappa} = \int_0^{\infty} H_{(k0-\hat{\kappa}/2n_0)} U_{\hat{\kappa},k0} \frac{\hat{\kappa}}{4n_0^2 k0^2} \, d\hat{\kappa} \qquad (38)$$

$$\int_{K/2n_0}^{\infty} \Gamma_{K,k} \, dk = H_{(k0-K/2n_0)} U_{K,k0} \frac{K}{4n_0^2 k0^2}. \qquad (39)$$

where in the evaluation of the integrals we have used $$\frac{-1}{k0+k_\Delta} + \frac{1}{k0} \approx \frac{k_\Delta}{k0}, \qquad (40)$$

valid for a narrow bandwidth $k_\Delta \ll k0$. In particular, the positive, nonzero portion of the spectrum reduces to $$q_{K>0,h} = \frac{H_K H_{(k0-K/2n_0)} U_{K,2n_0 k0} K \sqrt{RZ}}{4n_0^2 k0^2} \exp(iKh) \qquad (41)$$

Consequently, for this special case of a narrow spectral bandwidth light source, constant reflectivities R, Z and no phase contributions $\bar{\omega}$, $$\phi_{K,h}'' = Kh. \qquad (42)$$

In this special case, the phase is linearly proportional to surface height, consistent with conventional FDA. The spatial frequency also has a direct correspondence to the directional cosine:

$$K = \beta 2 n_0 k0. \qquad (43)$$

Thus there is a one-to-one relationship between the spatial frequency coordinate of the FDA spectra and the angle of incidence. Note further the K weighting in the Fourier magnitude $\sqrt{Q_K}$ calculated from Eq. (41). This is evident in the example spectrum FIG. 6(a), which shows the theoretical prediction for a perfectly uniform filling of the pupil plane over a range starting from normal incidence up to the directional cosine limit imposed by the objective NA:

$$\beta_{NA} = \sqrt{1 - NA^2} \qquad (44)$$

As a second example, consider the case of broadband illumination with uniform illumination restricted to a narrow range $\beta_\Delta$ of directional cosines near normal incidence. The normalize pupil plane distribution is then $$U_\beta = \frac{1}{\beta_\Delta} H_{1-\beta} H_{\beta-(1-\beta_\Delta)}. \qquad (45)$$

After the change of variables, $$U_{K,k} = \frac{1}{\beta_\Delta} H_{(2kn_0-K)} H_{[K-2kn_0(1-\beta_\Delta)]} \qquad (46)$$

The definite integrals in Eq. (34) are in this case of the form $$\int_0^{\infty} \int_{K/2n_0}^{\infty} \Gamma_{\hat{\kappa},k} \, dk \, d\hat{\kappa} = \frac{1}{\beta_\Delta} \int_0^{\infty} \int_{\hat{\kappa}/2n_0}^{\hat{\kappa}/(1-\beta_\Delta)2n_0} \frac{V_k \hat{\kappa}}{4k^2 n_0^2} \, dk \, d\hat{\kappa} \qquad (47)$$

$$\int_{K/2n_0}^{\infty} \Gamma_{K,k} \, dk = \frac{1}{\beta_\Delta} \int_{K/2n_0}^{K/(1-\beta_\Delta)2n_0} \frac{V_k K}{4k^2 n_0^2} \, dk \qquad (48)$$

which evaluate to $$\int_0^\infty \int_{K/2n_0}^\infty \Gamma_{\hat{k},k} \, dk \, d\hat{k} = \int_0^\infty \frac{V_{K/2n_0}}{2n_0} \, d\hat{k} \quad (49)$$

$$\int_{K/2n_0}^\infty \Gamma_{K,k} \, dk = \frac{V_{K/2n_0}}{2n_0}. \quad (50)$$

where we have used $$\frac{(1-\beta_\Delta)2n_0}{\hat{k}} - \frac{2n_0}{\hat{k}} = -\frac{2n_0\beta_\Delta}{\hat{k}} \quad (51)$$

The positive, nonzero portion of the spectrum is for this broadband source illumination and near-normal incidence is therefore $$q_{K>0,h} = \frac{V_{K/2n_0}\sqrt{RZ}}{2n_0}\exp(iKh) \quad (52)$$

Figures 6A, 6B:
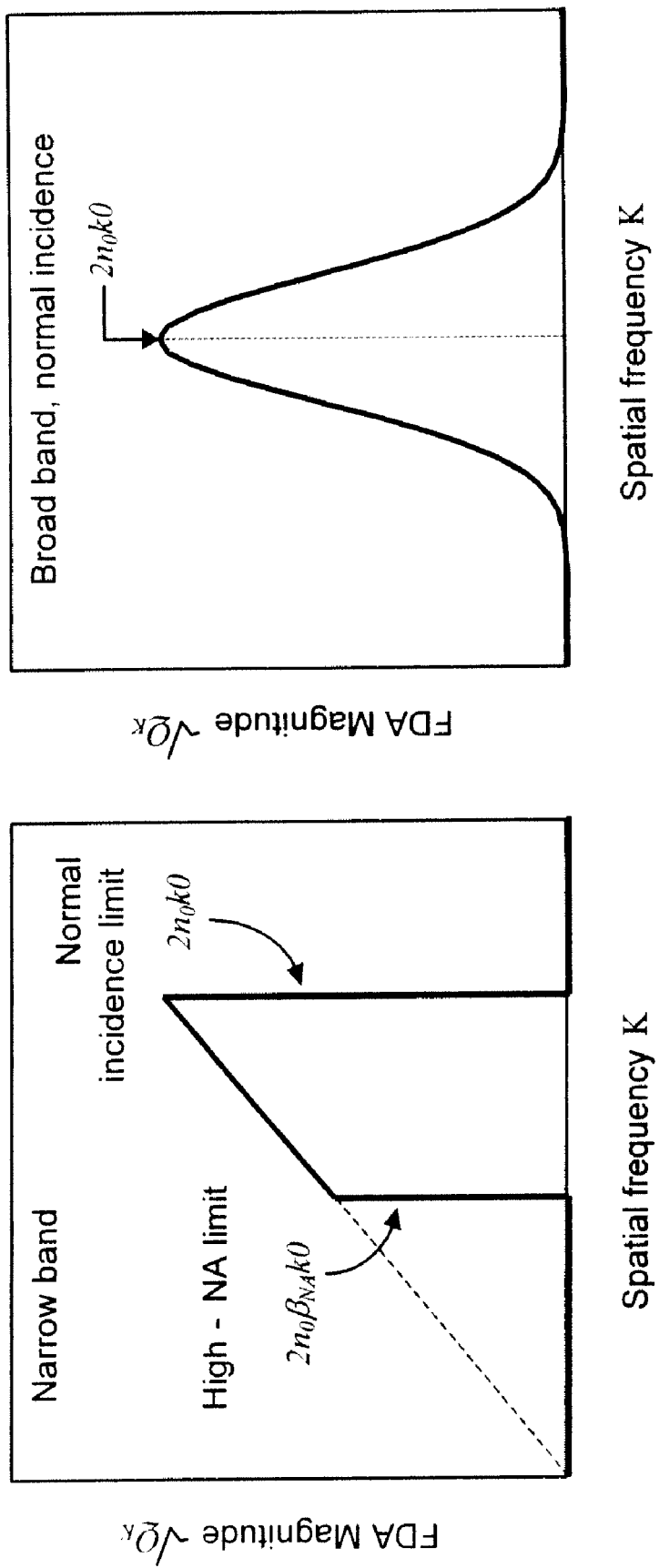
FIG. 6 shows theoretical Fourier amplitude spectra for scanning interferometry data in two limits.

This corresponds closely to the familiar result that the Fourier magnitude $\sqrt{Q_K}$ is proportional to the source spectrum distribution $V_{K/2n_0}$, as shown e.g. in FIG. 6(b) for a gaussian spectrum centered on a nominal or mean wavelength k0. Note that Eq. (52) also conforms to the assumption of linear phase evolution $$\phi_{K,h}'' = Kh \quad (53)$$

consistent with conventional FDA.

Since the Fourier magnitude $\sqrt{Q_{K,h}} = |q_{K,h}|$ and phase $\phi_{K,h}'' = \arg(q_{K,h})$ are derived from the Fourier Transform of the interference intensity $I_{\zeta,k}$, the inverse transform puts us back into the domain of real interference signals $$I_{\zeta,h} = \int_{-\infty}^\infty q_{\hat{k},h}\exp(-i\hat{k}\zeta) d\hat{k} \quad (54)$$

where once again we have used $\hat{\kappa}$ as for the spatial frequency to emphasize that it is a free variable of integration in Eq. (54). Thus one way to calculate the intensity signal is to generate the Fourier components $q_{K,h}$ by Eq. (33) and transform to $I_{\zeta,h}$ using Eq. (54).

We assume random polarization of the source light in the present model. This does not mean, however, that we should neglect polarization effects. Rather, in the above calculations, we assume an incoherent superposition of equally weighted results from the two orthogonal polarization states s and p defined by the plane of incidence of the illumination. Using superscript notation for the polarizations, $$q_{\beta,k} = q_{\beta,k}^s + q_{\beta,k}^p. \quad (55)$$

Therefore, the average phase angle for unpolarized light at this $\beta$, k would be $$\langle\phi_{\beta,k}''\rangle = \arg(q_{\beta,k}^s + q_{\beta,k}^p). \quad (56)$$

Note that unless the magnitudes are identical for the two polarization contributions, most often $$\langle\phi_{\beta,k}''\rangle \neq (\phi_{\beta,k}''^s + \phi_{\beta,k}''^p)/2. \quad (57)$$

Also, unless $q_{\beta,k}^s$ and $q_{\beta,k}^p$ are perfectly parallel in the complex plane, $$\langle Q_{\beta,k}\rangle \neq (Q_{\beta,k}^s + Q_{\beta,k}^p)/2. \quad (58)$$

The same observation applies to the system and object reflectivities $R_{\beta,k}^s$, $R_{\beta,k}^p$ and $Z_{\beta,k}^s$, $Z_{\beta,k}^p$, respectively; they cannot be summed directly unless they have identical phases.

Provided that we take proper care of the polarization effects in the calculation of the object surface reflectivity, the modeling remains fairly straightforward and is flexible enough to handle the more interesting cases of polarized light further down the line.

The next step is to translate to discrete numerical formulas, in view of a software development. We redefine the relationship between the interference signal $I_{\zeta,h}$ and the Fourier spectrum $q_{K,h}$ using discrete Fourier transforms as $$q_{K,h} = \frac{1}{\sqrt{N}}\sum_\zeta I_{\zeta,h}\exp(iK\zeta) \quad (59)$$

$$I_{\zeta,h} = \frac{1}{\sqrt{N}}\left[q_0 + \sum_{K>0} q_{K,h}\exp(-iK\zeta) + \sum_{K>0}\bar{q}_{K,h}\exp(iK\zeta)\right] \quad (60)$$

where $\bar{q}_{\hat{k},h}$ is the complex conjugate of $q_{\hat{k},h}$ and there are N discrete samples in the interference signal $I_{\zeta,h}$. In Eq. (60) and what follows, we have set aside the use of a free variable $\hat{\kappa}$ that was important in the derivations but it is no longer needed as a substitute for the spatial frequency K. The predicted positive-frequency FDA complex spectrum is then $$q_{K\leq 0,h} = \sigma_{K>0}\exp(iKh) \quad (61)$$

where the normalized, height-independent coefficients are $$\rho_{K>0} = \frac{\sqrt{N}}{\Upsilon}\sum_k H_{k-K/2n_0}\sqrt{R_{K,k}Z_{K,k}}\exp[i(\upsilon_{K,k}-\omega_{K,k})]\Gamma_{K,k} \quad (62)$$

$$\rho_0 = \frac{\sqrt{N}}{\Upsilon}\sum_{K\geq 0}\sum_k H_{k-K/2n_0}(R_{K,k}+Z_{K,k})\Gamma_{K,k} \quad (63)$$

where the normalization for the range of integration is $$\Upsilon = \sum_{K\geq 0}\sum_k H_{k-K/2n_0}\Gamma_{K,k} \quad (64)$$

The Heaviside step functions H in Eq. (62) prevent unnecessary contributions to the sums. The weighting factor $\Gamma_{K,k}$ is as defined in Eq. (24).

To compare experiment with theory, we use Eq. (61) to generate an experimental FDA spectrum and Eq. (62) to transform back into the space domain for the theoretical prediction of $I_{\zeta,h}$. This is most efficiently performed by fast Fourier transforms (FFT). The properties of the FFT determine the range of K values. If the N discrete samples for $I_{\zeta,h}$ are spaced by an increment $\zeta_{step}$, there will be N/2+1 positive spatial frequencies starting from zero and rising to N/2 cycles per data trace, spaced by an increment $$K_{step} = \frac{2\pi}{N\zeta_{step}}. \tag{65}$$

To facilitate phase unwrapping in the frequency domain, we try to adjust the zero position for the scan so that it is near the signal peak, thus reducing the phase slope in the frequency domain. Because an FFT always assumes that the first data point in the scan is at zero, the signal should be properly offset.

We now focusing on modeling a sample surface with a thin film.

Figure 7A:
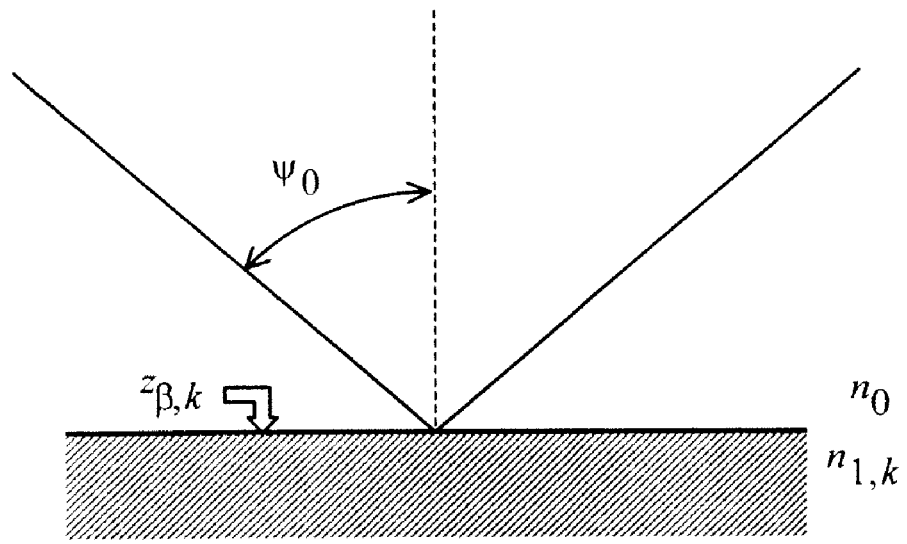
FIG. 7 shows two surface types, with and without a thin film

FIG. 7 shows two surface types, with and without a thin film. For both cases, we define an effective amplitude reflectivity $z_{\beta,k}$ according to $$z_{\beta,k} = \sqrt{Z_{\beta,k}} \exp(i\omega_{\beta,k}) \tag{66}$$

where $Z_{\beta,k}$ is the intensity reflectivity and $\omega_{\beta,k}$ is the phase change on reflection. The subscripts $\beta,k$ emphasize a dependency on the directional cosine of the illumination $$\beta_0 = \cos(\psi_0), \tag{67}$$

where $\psi_0$ is the incident angle, and on the wavenumber $$k = (2\pi/\lambda) \tag{68}$$

where $\lambda$ is the wavelength of the light source. The subscript $\beta$ will be understood to refer to the first incident directional cosine $\beta_0$.

The surfaces are characterized in part by their index of refraction. The index of the surrounding medium, usually air, is $n_0$. For the simple surface FIG. 7(a) there is only one index $n_1$. For the thin film in FIG. 7(b), there are two surface indices, $n_1$ for the transparent or partially transparent film and $n_2$ for the substrate. Most generally, these refractive indices are complex numbers characterized by a real part and an imaginary part. For example, a typical index, e.g. for chrome at $\lambda$=550 nm, is $n_1$=3.18+4.41i, where we are adopting the convention where the imaginary part is defined as positive.

The index of refraction of a material depends on the wavelength. The dispersion in refractive index $n_0$ for the air is not very significant, but is important for many sample surfaces, especially metals. Over small wavelength changes near a nominal k0, most materials have a nearly linear dependence on wavenumber, so that we can write $$n_{1,k} = v_1^{(0)} + k v_1^{(1)} \tag{69}$$

where $v_1^{(0)}$, $v_1^{(1)}$ are the intercept and slope, respectively, for the index of refraction $n_1$ at the nominal wavenumber k0.

Figure 7B:
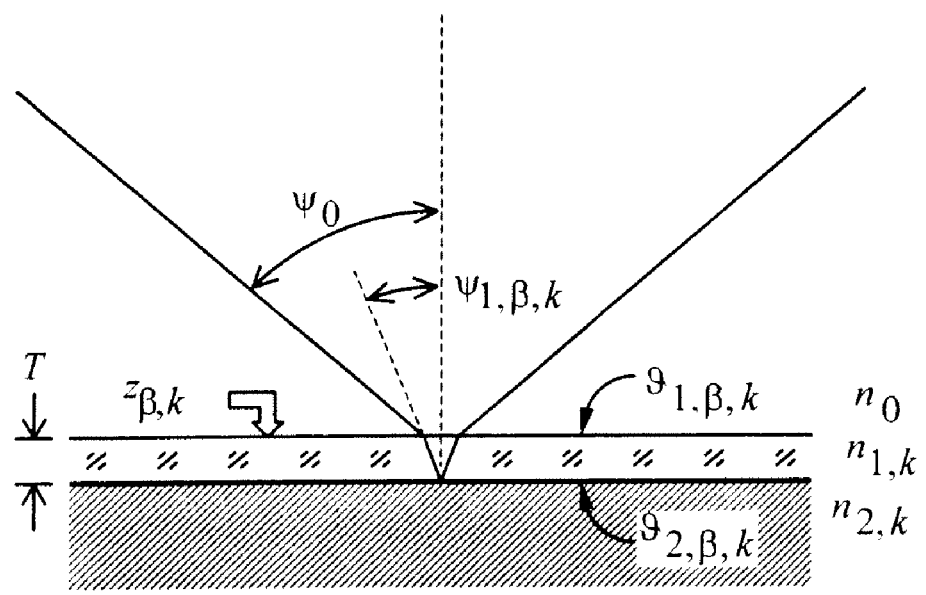

The most common use of the refractive index is Snell's law. Referring to FIG. 7(b), the refracted beam angle internal to the film is $$\psi_{1,\beta,k} = \arcsin\left[\frac{n_0}{n_{1,\beta,k}} \sin(\psi_0)\right], \tag{70}$$

where $\psi_0$ is the angle within the medium of index $n_0$ incident on the top surface of the medium of index $n_1$, and $\psi_{1,\beta,k}$ is the angle of refraction. It is possible for these angles to take on complex values if the indices are complex, indicating partially evanescent propagation.

The complex amplitude reflectivity of a boundary between two media depends on the polarization, the wavelength, the angle of incidence and the index of refraction. The s- and p-polarization reflectivities of the top surface of the film in FIG. 7(b) are given by the Fresnel formulae $$\partial_{1,\beta,k}^s = \frac{\tan(\psi_0 - \psi_{1,\beta,k})}{\tan(\psi_0 + \psi_{1,\beta,k})} \tag{71}$$

$$\partial_{1,\beta,k}^p = -\frac{\sin(\psi_0 - \psi_{1,\beta,k})}{\sin(\psi_0 + \psi_{1,\beta,k})} \tag{72}$$

The dependence on $\beta,k$ results from the angles $\psi_0, \psi_{1,\beta,k}$, the exit angle $\psi_{1,\beta,k}$ introducing a k dependency via the refractive index $n_{1,k}$. Similarly, the substrate-film interface reflectivities are $$\partial_{2,\beta,k}^p = \frac{\tan(\psi_{1,\beta,k} - \psi_{2,\beta,k})}{\tan(\psi_{1,\beta,k} + \psi_{2,\beta,k})} \tag{73}$$

$$\partial_{2,\beta,k}^s = -\frac{\sin(\psi_{1,\beta,k} - \psi_{2,\beta,k})}{\sin(\psi_{1,\beta,k} + \psi_{2,\beta,k})} \tag{74}$$

Note that in the Fresnel equations, if the angle of incidence and refraction are the same, the reflectivity for both polarizations goes to zero.

For a simple surface (no thin film), the sample surface reflectivity is identical to the top-surface reflectivity $$z_{\beta,k} = \theta_{1,\beta,k} \text{(simple surface, no thin film)} \tag{75}$$

Consequently, the phase change on reflection (PCOR) caused by the surface reflection is $$\omega_{\beta,k} = \arg(\theta_{1,\beta,k}). \tag{76}$$

Note that to satisfy the boundary conditions, the s-polarization "flips" upon reflection ($=\pi$ phase shift for a dielectric), whereas the p-polarization does not. The distinction between polarization states becomes meaningless exactly at normal incidence, which in any case results in a division by zero in the Fresnel equations and a different formula handles this limit case.

When using the plus sign convention for the complex part of the index of refraction, the greater the absorption (complex part), the greater the PCOR $\omega_{\beta,k}$. In other words, a larger absorption coefficient is equivalent to a decrease in effective surface height. This makes intuitive sense—one imagines absorption as a penetration of the light beam into the material prior to reflection, rather than a clean reflection and transmission right at the boundary. Following our usual convention, for which an increase in surface height corresponds to a positive change in the phase difference between the reference and measurement surfaces, a positive surface PCOR subtracts from the interferometer phase.

A thin film is a special case of a parallel plate reflection. The light passes through the top surface partially reflected (see FIG. 7) and continues to the substrate surface where there is a second reflection with a phase delay with respect to the first. However, this is not the end of the story. The light reflected from the substrate is once again partially reflected when passing back up through the top surface, resulting in an additional reflected beam heading south again to the substrate. This goes on in principle forever, with each additional reflection a little weaker than the last. Assuming that all of these multiple reflections survive to contribute to the final surface reflectivity, the infinite series evaluates to $$z_{\beta,k} = \frac{\vartheta_{1,\beta,k} + \vartheta_{2,\beta,k}\exp(2ikL\beta_{1,\beta,k}n_{1,k})}{1 + \vartheta_{1,\beta,k}\vartheta_{2,\beta,k}\exp(2ikL\beta_{1,\beta,k}n_{1,k})} \quad (77)$$

$$\beta_{1,\beta,k} = \cos(\psi_{1,\beta,k}). \quad (78)$$

As a note of clarification, recall the $\beta$ dependency of $\beta_{1,\beta,k}$ refers to a dependency on the incident directional cosine $\beta_0$ in the ambient medium of index $n_0$. The same Eq. (77) applies to both polarization states, with corresponding single-surface reflectivities.

Inspection of these equations shows why conventional FDA processing breaks down in the presence of thin films. Conventional FDA determines surface height by a linear fit to the Fourier phase spectrum weighted by the Fourier power spectrum, using broadband (white) light to generate the Fourier spatial frequency spread. The idea is that the phase evolution comes from the expected linear phase dependence on surface height. Any other constant offset or linear coefficients (e.g., "dispersion") associated with the surface characteristics are removed by system characterization or by simply ignoring those phase contributions that do not change with field position.

This works perfectly fine for simple surfaces. With unpolarized light, and most likely with the circularly-polarized light, the wavelength dependence of the PCOR is nearly linear with respect to wavenumber and constant for a given material. In the presence of a thin film, however, the conventional analysis breaks down. The phase becomes nonlinear and the phase slope becomes sensitive to film thickness, which may be varying across the field of view. Therefore, the present analysis determines key parameters of the surface structure such as film thickness by comparing experimental data to a theoretical prediction, using our knowledge of how e.g. a thin film modulates the reflectivity of the surface.

We now discuss how comparison of experimental data to a library of theoretical predictions provides surface structure parameters such as film thickness and phase change on reflection (PCOR). In the case of a film of unknown thickness, the library for a single surface type, e.g. $SiO_2$ on Si, would range over many possible film thicknesses. In frequency domain embodiments, the idea is to search this library for a match to those characteristics of the FDA spectra that are independent of surface topography, for example, a distinctive structure to the magnitude spectrum resulting from a thin-film interference effect. The computer then uses the library spectrum to compensate the FDA data, allowing for a more accurate surface topography map.

In one embodiment, the library contains example FDA spectra for surface structures, each spectrum providing a series of complex coefficients $\rho_K$ representing Fourier coefficients as a function of spatial frequency K. These spectra are the Fourier transforms of intensity data $I_{\zeta,h}$ acquired during a scan $\zeta$ of the optical path length of an interferometer. The spatial frequency K is proportional to the angular wavenumber $k=2\pi/\lambda$ for a segment of the source light spectrum, the index of refraction $n_0$ of the ambient medium, and the directional cosine $\beta=\cos(\psi)$, where $\psi$ is the angle of incidence for a ray bundle directed to the object surface:

$$K=2\beta kn_0. \quad (79)$$

The $\rho_K$ coefficients for the prediction library include the optical properties of the surface that can influence the appearance of the FDA spectra, with the exception of surface height.

Predicting the FDA spectra involves an integral representing the incoherent sum of ray bundles over a range of incident angles $\psi$ and angular wavenumbers k for the source light. As described above, the numerical integration can reduce to a computationally-efficient single sum over N angular wavenumbers k, weighted by a factor $\Gamma_{K,k}$:

$$\rho_{K>0} = \frac{\sqrt{N}}{\Upsilon}\sum_k H_{k-K/2n_0}\sqrt{R_{K,k}Z_{K,k}}\exp[i(\upsilon_{K,k}-\omega_{K,k})]\Gamma_{K,k} \quad (80)$$

$$\rho_0 = \frac{\sqrt{N}}{\Upsilon}\sum_{K\geq 0}\sum_k H_{k-K/2n_0}(R_{K,k}+Z_{K,k})\Gamma_{K,k} \quad (81)$$

The weighting factor is $$\Gamma_{K,k} = \frac{KU_{K,k}V_k}{4k^2n_0^2}, \quad (82)$$

where $V_k$ is the source spectrum and $U_{K,k}$ is the pupil-plane light distribution. The corresponding normalization $\Upsilon$ is the sum over all spatial frequencies of the weighting factor $$\Upsilon = \sum_{K\geq 0}\sum_k H_{k-K/2n_0}\Gamma_{K,k}. \quad (83)$$

where $\Upsilon$ is a normalization to be defined shortly and H is the Heaviside step function.

The distinctive characteristics of an object surface structure, particularly of a thin film, enter into the spectrum $\rho_K$ through the object-path phase $\omega_{K,k}$ and reflectivity $Z_{K,k}$, as detailed above. Equally important are the reference-path phase $\upsilon_{K,k}$ and reflectivity $R_{K,k}$, which depend on the scanning interferometer itself. Such factors can be determined by theoretically modeling the scanning interferometer or by calibrating it with a test sample having known properties, as described further below.

The typical prediction library for a thin film is a series of spectra $\rho_K$ indexed by film thickness L. The stored spectra cover only a narrow spatial frequency region of interest (ROI), usually 15 or 16 values for a 256-frame intensity data acquisition, the remainder of the values outside this ROI being zero. The limits of the ROI follow from the definition of the spatial frequency:

$$K^{min}=2\beta^{min}k^{min}n_0 \quad (84)$$

$$K^{max}=2\beta^{max}k^{max}n_0 \quad (85)$$

A typical range of spatial frequencies for a scanning interferometer based on a 100× Mirau objective and a narrow bandwidth, 500-nm light source is 2.7 $\mu m^{-1}$ to 4.0 $\mu m^{-1}$. For computational efficient, a dense look up table, indexed by 0.5 to 5 nm between sample spectra, can be used rather than an analytical search routine that involves recalculation using Eqs. (80)-(83) several times for each pixel.

The library search involves the following steps: (1) Select a predicted FDA spectrum from the library corresponding to a specific surface type, (2) calculate how closely this spectrum matches the experimental data using a merit function, then (3) repeat through several or all of the library data sets to determine which theoretical spectrum provides the best match. What we are looking for is a "signature" in the frequency domain that relates uniquely to surface characteristics such as thin films, dissimilar materials, step structures, roughness, and their interaction with the optical system of the interferometer. This comparison therefore explicitly filters away the linear rate of change of phase with spatial frequency, which is the one characteristic of the FDA spectrum that varies directly with surface topography and is therefore irrelevant to the library search.

In comparing spectra, there is a benefit to separating the phase and magnitude contributions to the merit calculation. Thus for the theory, we have $$P_K = |\rho_K| \tag{86}$$

$$\phi_K = \text{connect}_K[\arg(\rho_K)], \tag{87}$$

where $\text{connect}_K$ is a function that removes $2-\pi$ steps in the spatial frequency dependence of $\phi_{K,h}$. For the experimental data we have $$P_K^{ex} = |q_{k,h}^{ex}| \tag{88}$$

$$\phi''_{K,h}{}^{ex} = \text{connect}_K[\arg(q_{K,h}^{ex})], \tag{89}$$

The double prime for $\phi''_K{}^{ex}$ indicates an uncertainty in the fringe order from both pixel to pixel and overall with respect to the starting point in the scan. The experimental data necessarily include a slope term related to the local surface height; this is the reason for the use of the q symbol instead of the p symbol.

For a specific set of trial surface parameters, we can calculate a phase difference $$\zeta''_{K,h} = \phi''_{K,h}{}^{ex} - \phi_K \tag{90}$$

The phase difference $\zeta_{K,h}{}''$ is the compensated FDA phase, assuming that the trial parameters are correct. A good match of theory to experiment yields a phase $\zeta_{K,h}{}''$ that in principle is a simple linear function of spatial frequency K with an intercept of zero (i.e., zero phase gap). Thus, looking ahead, the successfully compensated phase $\zeta_{K,h}{}''$ is what we shall eventually feed downstream to a conventional FDA analysis, which assumes that the slope of the phase in frequency space is directly proportional to surface height.

Based on the observations of the previous paragraph, there are two features of interest in the compensated phase $\zeta_{K,h}{}''$ that allow us to evaluate the match of theory to experiment independent of surface height. The first is the phase gap A" or K=0 intercept value $\zeta_{K=0,h}{}''$ obtained by a linear fit, and the second is the residual nonlinearity with respect to wavenumber after a linear fit. Corresponding merit functions are, for example, $$\chi_\phi = \left[\frac{A''}{2\pi} - \text{round}\left(\frac{A''}{2\pi}\right)\right]^2 \tag{91}$$

$$\chi_{\phi non} = \frac{\sum_{K>0}(\zeta''_{K,h} - \sigma_h K - A'')^2 P_{K,h}^{ex}}{\sum_{K>0} P_{K,h}^{ex}} \tag{92}$$

where $\sigma_h$ is the slope of the (magnitude weighted) linear fit to the compensated phase $\zeta_{K,h}{}''$. The round( ) function in Eq. (91) limits the phase gap A" to the range $\pm\pi$.

Although a library search can proceed using phase information alone, i.e. by minimizing one or both of the merit function values $\chi_\phi$ and/or $\chi_{\phi non}$, we also have important and useful signatures in the Fourier magnitude. The magnitude is particularly interesting in that it is inherently independent of surface height. Thus for example, we can define in approximate analogy with the phase merits the following magnitude merit functions:

$$\chi_P = \left[\frac{\sum_{K>0}(P_{K,h}^{ex} - P_{K,h})}{\sum_{K>0}(P_{K,h}^{ex} + P_{K,h})}\right]^2 \tag{93}$$

$$\chi_{Pnon} = \frac{\sum_{K>0}(\Omega^{-1} P_{K,h}^{ex} - P_{K,h})^2}{\sum_{K>0}(\Omega^{-1} P_{K,h}^{ex} + P_{K,h})^2} \tag{94}$$

where $\Omega$ is the empirical scaling factor $$\Omega = \sum_{K>0} P_{K,h}^{ex} / \sum_{K>0} P_{K,h}. \tag{95}$$

The merit $\chi_P$ is most closely related to the overall reflectivity of the object surface, independent of spatial-frequency dependence, whereas $\omega_{Pnon}$ expresses how well the theoretical and experimental magnitude plots match in shape.

The magnitude merit functions $\chi_P$ and/or $\chi_{Pnon}$ are in addition to or even in place of the phase merits $\chi_\phi$ and/or $\chi_{\phi non}$. A general library search merit function is therefore $$\chi = w_\phi \chi_\phi + w_{\phi non} \chi_{\phi non} + w_P \chi_P + w_{Pnon} \chi_{Pnon} \tag{96}$$

where the w are weighting factors. In principle, one can determine the weights in Eq. (96) knowing the standard deviation for the various parameters. A more empirical approach is to try out various weights on real and simulated data and see how well they work. For the examples that follow, we select equal weights $w_\phi = w_{\phi non} = w_P = w_{Pnon} = 1$ for all merit contributions.

The examples in FIGS. 8-13 illustrate the merit-function search procedure for six $SiO_2$ on Si film thicknesses: 0, 50, 100, 300, 600, and 1200 nm, respectively. A single library for all examples encompasses the range from 0 to 1500 nm in 2-nm intervals. The data are simulations, free of noise. As in all the examples described herein, the scan step is 40 nm, the source wavelength is 498 nm, and the source gaussian FWHM is 30 nm (quasi-monochromatic).

The most interesting aspect of these simulated searches is the behavior of the four merit functions. Generally, we observe that inclusion of these four functions helps to reduce the ambiguity in the final merit values, there being a strong periodicity for individual merit values as a function of film thickness. Another general observation is that the merits based on nonlinearity, both in phase and magnitude, are most effective at 300 nm and above, whereas the phase gap and average magnitude are dominant below 300 nm film thickness. This shows that the $\chi_\phi$, $\chi_P$ merit functions are especially useful to the really thin films, which places importance on system characterization, which couples directly into the phase gap and magnitude results.

Once we determine the thin film thickness (or identify the material or other uses for the algorithm), FDA processing proceeds in the usual way, using however the corrected FDA phase $\zeta_{K,h}''$ instead of the original experimental phase data. In principle, if the modeling has been successful, $\zeta_{K,h}''$ should be free of nonlinearities and the phase gap should be zero. The next step therefore is a linear fit to the phase spectrum $\zeta_{K,h}''$. It appears more effective for high-NA FDA to use the magnitude spectrum $P_K$ in place of magnitude squared. The fit provides for each pixel a slope $$\sigma_h \approx d\zeta_{K,h}''/dK \tag{97}$$

and an intercept (phase gap)

$$A'' \approx \zeta_{K=0,h}''. \tag{98}$$

Note that the phase gap A" carries the double prime inherited from the fringe order uncertainty in the phase data. The slope $\sigma_h$ is free of this uncertainty. From the intercept A" and the slope $\sigma_h$, we define for a specific mean or nominal spatial frequency K0 a "coherence profile"

$$\Theta_h = \sigma_h K0 \tag{99}$$

and a "phase profile"

$$\theta_h'' = \Theta_h + A''. \tag{100}$$

We then removes the pixel-to-pixel fringe order uncertainty in the phase $\theta_h''$:

$$\theta' = \theta'' - 2\pi \operatorname{round}\left[\frac{A'' - \alpha'}{2\pi}\right] \tag{101}$$

where $\alpha'$ is an approximation to the original phase gap A" that is free of pixel-to-pixel $2\pi$ steps.

Finally, the height profile follows from $$h' = \theta'/K0. \tag{102}$$

Note that it is not necessary to subtract the phase offset $\gamma$, because it has already been done in generating the compensated phases $\zeta_{K,h}$.

The first example of a surface topography measurement (FIG. 14) is a pure simulation. The surface topography is everywhere zero, but there is an underlying film layer that progresses from 0 to 1500 nm in 10 nm increments. Using the same prediction library as in FIGS. 8-13, this test demonstrates unambiguous determination of film thickness throughout the range of the prediction library, albeit for perfect, noise-free data.

The next example (FIG. 15) is also a simulation, but with additive noise. The random additive noise is gaussian, with a standard deviation of 2 bits out of an average 128 intensity bits, which looks to be typical of real data. The results are clearly satisfactory despite the significant difference in reflectivity between $SiO_2$ and Si (4% to 45%).

We now address system characterization.

We define a phase offset $\gamma_{sys}$ and a linear dispersion $\tau_{sys}$ using data collected during a system characterization procedure. To include system characterization data, we correct the Fourier-transformed experimental data $q_K^{ex}$ prior to the library search and prior to any other FDA processing on a pixel-by-pixel basis using $$q_{K>0}^{ex} = M^{-1} \exp[-i\gamma_{sys} - i(K-K0)\tau_{sys}] q_{K>0}^{ex}. \tag{103}$$

where K0 is the nominal spatial frequency, which represents the nominal spectral frequency for the FDA data set, as identified e.g. by locating the midpoint of the ROI. Note that the theoretical library remains unchanged. The scaling coefficient M (greek capital "M") is a new system characterization that makes it possible to use object surface reflectivity as a parameter in the library search.

The phase offset $\gamma_{sys}$ and the system phase gap $A_{sys}$ as a functions of field position can be stored as a function of field position, and calculate the true system dispersion according to $$\tau_{sys} = (\gamma_{sys} - A_{sys})/K0. \tag{104}$$

The magnitude coefficient M is also field dependent.

The creation of system characterization data proceeds in a manner similar to that described above for the object sample. We move to an artifact having known characteristics, measure it, and determine the system characterization by looking at how the results differ from what we would expect for a perfect system. Specifically, using a known sample for which the correct library entry is predetermined, we generate the phase gap A" as in Eq. (98) and a final height h' as in Eq. (102). Then, assuming a perfectly flat artifact, we calculate the system phase offset $$\gamma_{sys} = K0h' \tag{105}$$

and the system phase gap $$A_{sys} = \operatorname{connect}_{xy}(A'') \tag{106}$$

where $\operatorname{connect}_{xy}()$ is pixel-to-pixel phase unwrapping. The magnitude map is $$M_{sys} = \sum_{K>0} P_{K,h}^{ex} / \sum_{K>0} P_{K,h}. \tag{107}$$

In some embodiments, several system characterizations can be averaged, perhaps using artifacts having similar surface structure to the final application (e.g. $SiO2$ on Si) over a range of sample types.

In much of the description and simulations above we have focused on thin film surface structures, however, the analysis is also applicable to other types of complex surface structures. In what follows we show how the scanning interferometry data can be analyzed to account for surface structures that are smaller than the optical resolution of the scanning interferometer microscope. The optical resolution is ultimately limited by the wavelength of the light source and the NA of the light collection optics.

FIG. 16a shows height profiles determined from actual scanning interferometry data of a 2400 lines per mm (1 pmm) grating having a peak-to-valley (PV) modulation depth of 120 nm using a light source at a 500-nm nominal wavelength. The top profile in FIG. 16a shows the height profile determined using a conventional FDA analysis. The conventional analysis indicates a PV modulation depth of only about 10 nm, greatly underestimating the actual modulation depth. This inaccuracy occurs because the grating has features at the limit of the optical resolution of the 500-nm instrument. This is so even though the pixel resolution of the camera in the instrument is more than sufficient to accurately resolve the grating.

One way of thinking about this effect is that the scanning interferometry signal for a first camera pixel generally corresponding to a first surface location also includes contributions from adjacent surface locations when those additional surface locations have surface features sufficiently sharp relative to the light wavelength to diffract light to the first pixel. The surface height features from those adjacent surface locations corrupt conventional analysis of the scanning interferometry signal corresponding to the first surface location.

At the same time, however, this means that the scanning interferometry signal corresponding to the first surface location includes information about the complex surface features nearby. FIG. 17 illustrates this by showing the scanning interferometry signal from pixels corresponding to various locations about a step height feature. For the signal in (a) the step height is to the right of the pixel and higher, for the signal in (b) the step passes directly through the pixel, and for the signal in (c) the step is to the left of the pixel and is lower. One signature that is immediately apparent in the signals is the reduction in fringe contrast in (b) relative to (a) and (c). For example, if the step height was equal to one-quarter of the wavelength and the pixel location corresponded exactly to the position of the step height, the fringe contrast in (b) should disappear entirely because interference from the two sides of the step would exactly cancel one another. There is also much information in the signals in shown in (a) and (c). For example, FIG. 18 shows the nonlinear distortions in the frequency domain phase spectra for the signals (a) and (c) of FIG. 17, respectively, resulting from the nearby step height. These spectra are indicated as (a) and (b), respectively, in FIG. 18. In the absence of the step height, the frequency domain phase spectra would be linear. Thus, the nonlinear features in the frequency domain phase spectrum for pixels corresponding to surface locations adjacent to the step height nonetheless include information about the step height.

To more accurately measure the surface profile of a test surface in the presence of such under-resolved surface features, we can use the library searching technique described above for thin films. For example, for the case of a test surface with an under-resolved grating, a series of model FDA spectra are generated for different values of the PV modulation depth and offset position. As in the thin film examples, the surface height for the model spectra remains fixed. The analysis then continues as in the thin film examples above, except that rather than the model spectra being parameterized by thin film thickness, they are parameterized by modulation depth and offset position. Comparison between signatures of the FDA spectra for the actual test surface and the different model spectra can then be used to determine a match. Based on the match, distortions in the actual FDA spectrum for each pixel caused by the presence of the grating are removed so that the surface height for each pixel can be determined using conventional processing. The results of such an analysis using the same merit functions as described above for the thin films are shown in FIGS. 16b and 19b.

Figure 19A:
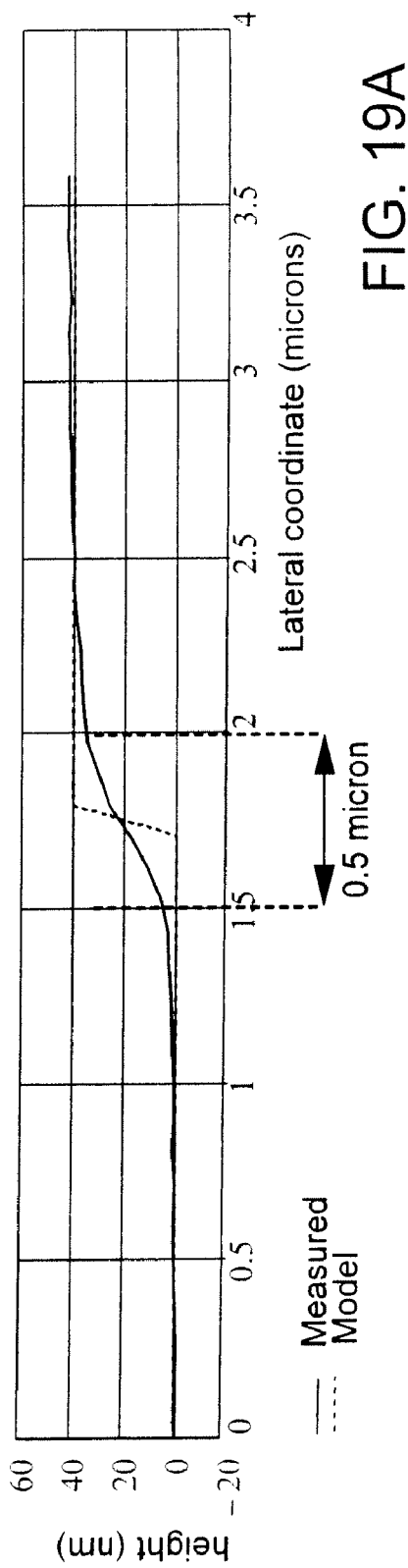
FIG. 19 shows surface height profiles determined using conventional FDA analysis (FIG. 19a) and a library search method described herein (FIG. 1b) for an under-resolved step height.
Figure 19B:
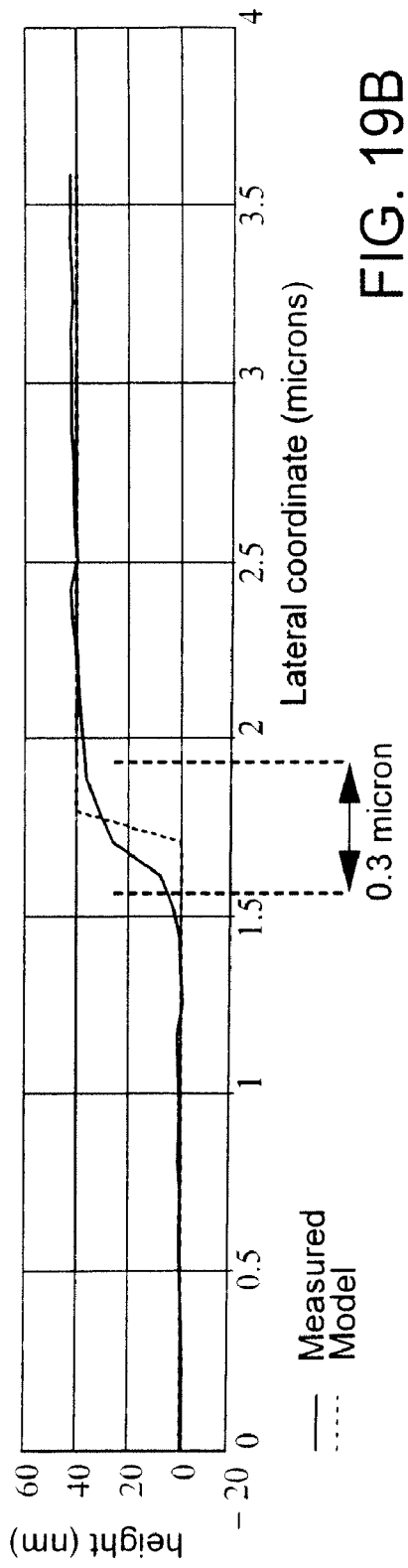

FIG. 16b shows the height profile determined using the library search analysis for 2400 lines per mm grating described above with reference to FIG. 16a. The same data was used in the FIGS. 16a and 16b, however, the library search analysis determined the PV modulation depth for the grating to be 100 nm, much closer to the actual 120-nm modulation depth than the 10-nm result determined by conventional FDA processing in FIG. 16a. FIGS. 19a and 19b show a similar analysis for a simulation with a discrete step height and assuming a nominal 500-nm light source. FIG. 19a shows the height profile determined using conventional FDA processing (solid line) compared to the actual height profile for the simulation (dotted line). FIG. 19b shows the height profile determined using the library search method (solid line) compared to the actual height profile for the simulation (dotted line). The parameters for the model spectra in the library search were location and step height magnitude. As illustrated, the library search analysis improves lateral resolution from about 0.5 microns to about 0.3 microns.

In the example of the FIG. 19a-b, the library was generated theoretically using an equation similar to Eq. (77) for a thin film, except in this case the denominator is set to 1 (because there are no multiple reflections from underlying layers), the first and second terms in the numerator are weighted according to the lateral distance of the measurement point from the actual step height position, and the parameter L corresponds to the step height itself rather than thin film thickness. Thus this theoretical model is based on a complex summing of rays emerging from either side of the step height. As the lateral position of the pixel under inspection increases in distance from the position of the step height, the signal tends to that of a simple flat surface.

In the example of FIG. 16a-b, the library was generated experimentally by observing the signal produced by the interferometry instrument for the 2400 line grating. Based on this experimental data, signatures in the scanning interferometry data were correlated with a corresponding lateral position in the period of the grating to build up the library. Experimental data for each pixel of the test sample (which in this case was the same 2400 line grating) was then compared with the library to determine the best lateral position in the period for that pixel.

In the detailed analyses described above the comparison between information in the actual data and information corresponding to the different models has occurred in the frequency domain. In other embodiments, the comparison can be made in the scan coordinate domain. For example, while changes in the absolute position of the fringe contrast envelope is generally indicative of changes in surface height at a first surface location corresponding to the signal in question, the shape of the signal (independent of its absolute position) contains information of complex surface structure, such as underlying layers at the first surface location and/or surface structure at adjacent locations.

One simple case is to consider to the magnitude of the fringe contrast envelope itself. For example, when a thin film thickness is very small relative to the range of wavelengths produced by the light source, the interference effects produced by the thin film become wavelength independent, in which case thin film thickness directly modulates the magnitude of the fringe contrast envelope. So, in general, the fringe contrast magnitude can be compared to that for models corresponding to different thin film thicknesses to a identify a match for a particular thin film thickness (taking into account systematic contributions from the interferometer itself)

Another simple case is to look at the relative spacings of the zero crossings of the fringes under the fringe contrast envelope. For a simple surface structure illuminated with a a symmetric frequency distribution, the relative spacings between the different zero crossings should be nominally the same. Variations in the relative spacings are therefore indicative of complex surface structure (when taking into account systematic contributions from the interferometer itself) and can compared to models for different complex surface structures to identify a match to a particular surface structure.

Another case is to perform a correlation between the scan-domain signal and the scan-domain signals corresponding to different models of the test surface. A match generally corresponds to the correlation that has the highest peak value, which indicate the model whose scan-domain signal has a shape most similar to the shape of the actual signal. Note that such analysis is generally independent of surface height because a difference between the surface height of the actual sample and that of each model only shifts the location of peak in the correlation function, but does not effect, in general, the peak value itself. On the other hand, once the correct model is identified, the location of the peak in the correlation function of the correct model yields the surface height for the test sample, without the need for further analysis (such as conventional FDA).

Like the analysis in the spatial frequency domain, an analysis in the scan-coordinate domain can be used for many different types of complex surfaces, including not only thin films, but also other complex surface structures such as under-resolved surface height features as described above.

We now describe in detail a scan-coordinate library search analysis the involves a correlation between the signal for the test sample and corresponding signals for various models of the test sample.

The approach sets aside any assumptions about the interference pattern other than to say that all pixels in a data set corresponding to surface locations with the same complex surface characteristics contain the same basic, localized interference pattern, only shifted in position (and possibly rescaled) for each pixel. It does not matter what the signal actually looks like, whether it is a gaussian envelope or has a linear phase behavior in the frequency domain or whatever. The idea is to generate a sample signal or template that represents this localized interference pattern for different models of complex surface structures for the test object, and then for each pixel, find the model whose localized interference pattern best matches the shape of the actual localized interference pattern, and for that model, find the scan position within the data set that provides the best match between the interference pattern template and the observed signal—which gives the surface height. Several techniques are available for pattern matching. One approach is to mathematically correlate each template with the data. Using a complex (i.e. real plus imaginary) template function for each model, we recover two profiles, one closely associated with the envelope of the signal and the other associated with the phase of the underlying carrier signal.

In one embodiment, for example, the analysis for each pixel would be include: (1) selecting a test template from a library of templates calculated or recorded for a specific value of an adjustable parameter, such as film thickness; (2) finding the local surface height using the selected test template and a correlation technique (an example of which is described below); (3) recording the peak merit function value for the selected test template based on the correlation technique; (4) repeating steps 1-3 for all or a subset of the templates in the library; (5) determining which test template provides the best match (=highest peak merit function value); (6) recording the value for the adjustable parameter for the best-matched template (e.g., thin film thickness); and (7) recalling the height value that provided the peak match position within the data trace.

We now describe a suitable correlation technique based on a complex correlation. For each model of the test surface we generate a template interference pattern $$I_{temp}^j(\zeta) = m_{temp}^j(\zeta)\cos[K_0\zeta + \phi_{temp}^j(\zeta)] \quad (108)$$

where the index j indicates the specific model for the template pattern. The functions $m_{temp}^j(\zeta)$ and $\phi_{temp}^j(\zeta)$ characterize the complex surface structure, but are independent of surface height at the location corresponding to the signal, which is set to zero. In preferred embodiments, the functions $m_{temp}^j(\zeta)$ and $\phi_{temp}^j(\zeta)$ also account for systematic contributions from the interferometer. We then use a complex representation for the template pattern:

$$\tilde{I}_{temp}^j(\zeta) = m_{temp}^j(\zeta)\exp[i(K_0\zeta + \phi_{temp}^j(\zeta))]. \quad (109)$$

We further use a window function to select a particular portion of the complex template function:

$$w(\zeta) = \begin{cases} 1 & \text{for } \zeta_{start} \leq \zeta \leq \zeta_{stop} \\ 0 & \text{otherwise} \end{cases} \quad (110)$$

$$\tilde{I}_{pat}^k(\zeta) = w(\zeta)\tilde{I}_{temp}^k(\zeta) \quad (111)$$

For example, an appropriate window might be $$\zeta_{start} = -\frac{\Delta\zeta}{2}$$

$$\zeta_{stop} = +\frac{\Delta\zeta}{2} \quad (112)$$

where the window width $\Delta\zeta$ could be set by hand.

Now that we have an interference pattern template $\tilde{I}_{pat}^j$ we are ready to use it for comparison to an actual data set. In preparation for this, it will be handy to generate a complex signal $\tilde{I}_{ex}$ starting from a real experimental data set $$I_{ex}(\zeta,x) = DC_{ex}(x) + \ldots AC_{ex}(x)m_{ex}[\zeta - h_{ex}(x)]\cos\{-[\zeta - h_{ex}(x)]K_0 + \phi_{ex}[-h_{ex}(x)]\}. \quad (113)$$

The Fourier transform of this signal is $$q_{ex}(K,x) = FT\{I_{ex}(\zeta,x)\} \quad (114)$$

$$q_{ex}(K,x) = \delta(K)DC_{ex}(x) + \tfrac{1}{2}AC_{ex}(x)[G_{ex}*(-K-K_0,x) + G_{ex}(K-K_0,x)] \quad (115)$$

where $$G_{ex}(K) = FT\{m_{ex}(\zeta)\exp[i\phi_{ex}(\zeta)]\}\exp[iKh_{ex}(x)]. \quad (116)$$

We then construct a partial spectrum from the positive-frequency portion of the spectrum:

$$\tilde{q}_{ex}(K) = AC_{ex}(x)G_{ex}(K-K_0,x). \quad (117)$$

The inverse transform is then $$\tilde{I}_{ex}(\zeta) = FT^{-1}\{\tilde{q}_{ex}(K)\} \quad (118)$$

$$\tilde{I}_{ex}(\zeta,x) = AC_{ex}(x)m_{ex}[\zeta - h_{ex}(x)]\exp\{-i[\zeta - h_{ex}(x)]K_0 + i\phi_{ex}[\zeta - h_{ex}(x)]\} \quad (119)$$

Here, the real part of this complex function $\tilde{I}_{ex}$ is the original experimental data $I_{ex}$. Further, the phase and envelope are separable by simple operations, e.g. we can access the product of the signal strength $AC_{ex}(x)$ and envelope $m_{ex}$ using the magnitude of the complex function $\tilde{I}_{ex}$:

$$AC_{ex}(x)m_{ex}[\zeta - h_{ex}(x)] = |\tilde{I}_{ex}(\zeta,x)|. \quad (120)$$

According to the underlying theory of the technique, we expect at least a meaningful portion of $m_{ex}$ to have the same general shape as $m_{temp}^j$ for the correct model, the only difference temp being the linear offset $h_{ex}$ and the scaling factor $AC_{ex}(x)$. We also expect the difference between the experimental and interference pattern template phase offsets $\phi_{ex}$, $\phi_{pat}^j$, respectively, to be linearly proportional to the height $h_{ex}$, for the correct model.

The task at hand is to locate a specific signal pattern represented by the interference pattern template $\tilde{I}_{pat}^j$ within an experimental data set $\tilde{I}_{ex}$, and determine how well of a match there is for each of the different models j. In what follows, we shall drop the index j, and note the matching analysis proceeds for each of the models.

The first step is to find the scan position $\zeta_{best}$ for which the shapes of the envelopes $m_{ex}$, $m_{pat}$ and $\phi_{ex}$,$\phi_{pat}$ are best matched. A viable approach is a merit function based on the normalized correlation of the interference pattern template with the signal within a segment of the scan defined by the window w:

$$\Pi(\zeta, x) = \frac{|\tilde{I}(\zeta, x)|^2}{\langle m_{pat}^2 \rangle \langle |\tilde{I}_{ex}(\zeta, x)|^2 \rangle} \quad (121)$$

where $$\tilde{I}(\zeta, x) = \frac{1}{N} \int_{-\infty}^{\infty} \tilde{I}_{pat}^*(\hat{\zeta}) \tilde{I}_{ex}(\zeta + \hat{\zeta}, x) d\hat{\zeta}. \quad (122)$$

is the complex correlation function and $$\langle m_{pat}^2 \rangle = \frac{1}{N} \int_{-\infty}^{\infty} |\tilde{I}_{pat}(\hat{\zeta})|^2 d\hat{\zeta} \quad (123)$$

$$\langle |\tilde{I}_{ex}(\zeta, x)|^2 \rangle = \frac{1}{N} \int_{-\infty}^{\infty} |\tilde{I}_{ex}(\zeta + \hat{\zeta}, x)|^2 w(\hat{\zeta}) d\hat{\zeta} \quad (124)$$

are normalizations that make the merit function $\Pi$ independent of signal-strength. Use of the complex conjugate $\tilde{I}_{pat}^*$ of the template cancels the synchronous linear phase term $K_0\zeta$ and maximizes $\Pi$ for the case of a match of $\phi_{ex}$,$\phi_{pat}$. The absolute value || of the correlation removes any residual complex phase.

To prevent $\Pi(\zeta)$ from generating false high values or encountering a singularity at low signal levels, it is prudent to add a minimum value to the denominator, such as $$\langle |\tilde{I}_{ex}(\zeta)|^2 \rangle \leftarrow \langle |\tilde{I}_{ex}(\zeta)|^2 \rangle + MinDenom \cdot \max(\langle |\tilde{I}_{ex}|^2 \rangle) \quad (125)$$

where the max ( ) function returns the maximum value of the signal strength $|\tilde{I}_{ex}|$ over the full scan length $\zeta$, and MinDenom is the minimum relative signal strength that we consider valid in the merit function search. The value of MinDenom can be hard coded at 5% or some other small value, or left as an adjustable parameter.

The correlation integral $\tilde{I}$ can also be performed in the frequency domain using the correlation theorem:

$$\tilde{I}(\zeta) = FT^{-1}\{\tilde{q}_{pat}^*(K)\tilde{q}_{ex}(K)\} \quad (126)$$

where we have made use of $$FT\{\tilde{I}_{pat}^*(\zeta,x)\} = \tilde{q}_{pat}^*(-K,x) \quad (127)$$

where $$\tilde{q}_{pat}(K,x) = FT\{\tilde{I}_{pat}(\zeta,x)\}. \quad (128)$$

A search through $\Pi$ to find a peak value yields the best match position $\zeta_{best}$ and the value of $\Pi$ is a measure of the quality of the match, ranging from zero to one, with one corresponding to a perfect match. The peak value of the merit function is calculated for each of the different models to determine which model is the best match, and then the best match position $\zeta_{best}$ for that model gives the surface height.

Figure 20:
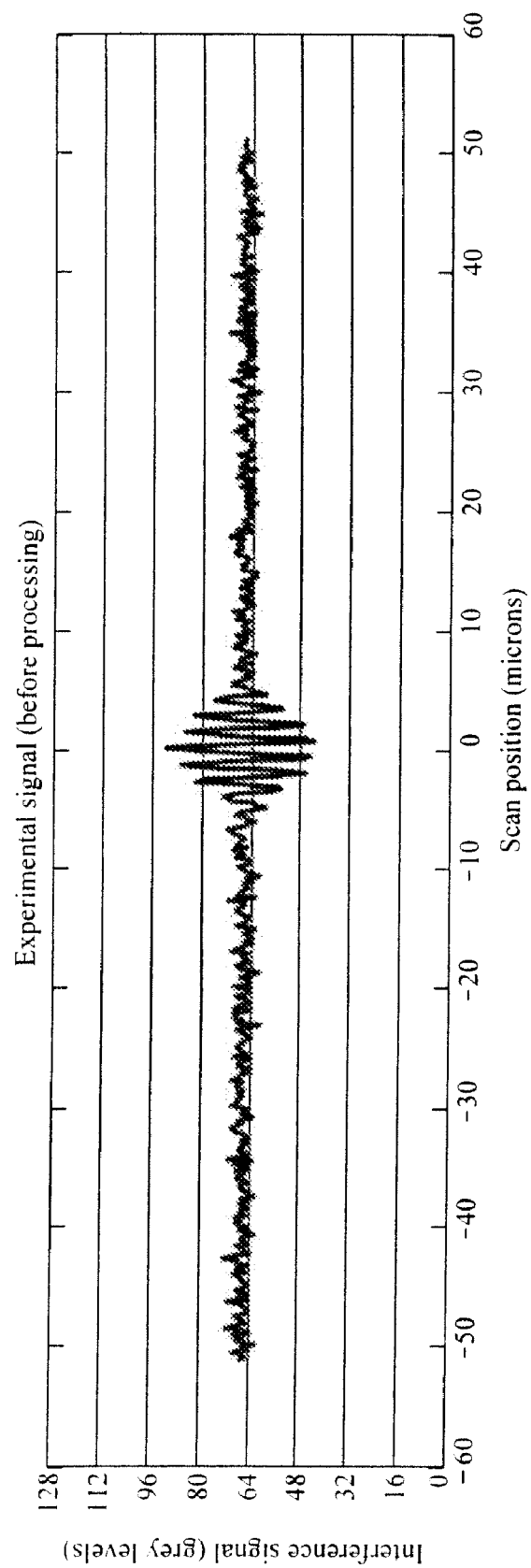
FIG. 20 shows an actual scanning interferometry signal of a base Si substrate without a thin film.
Figure 21:
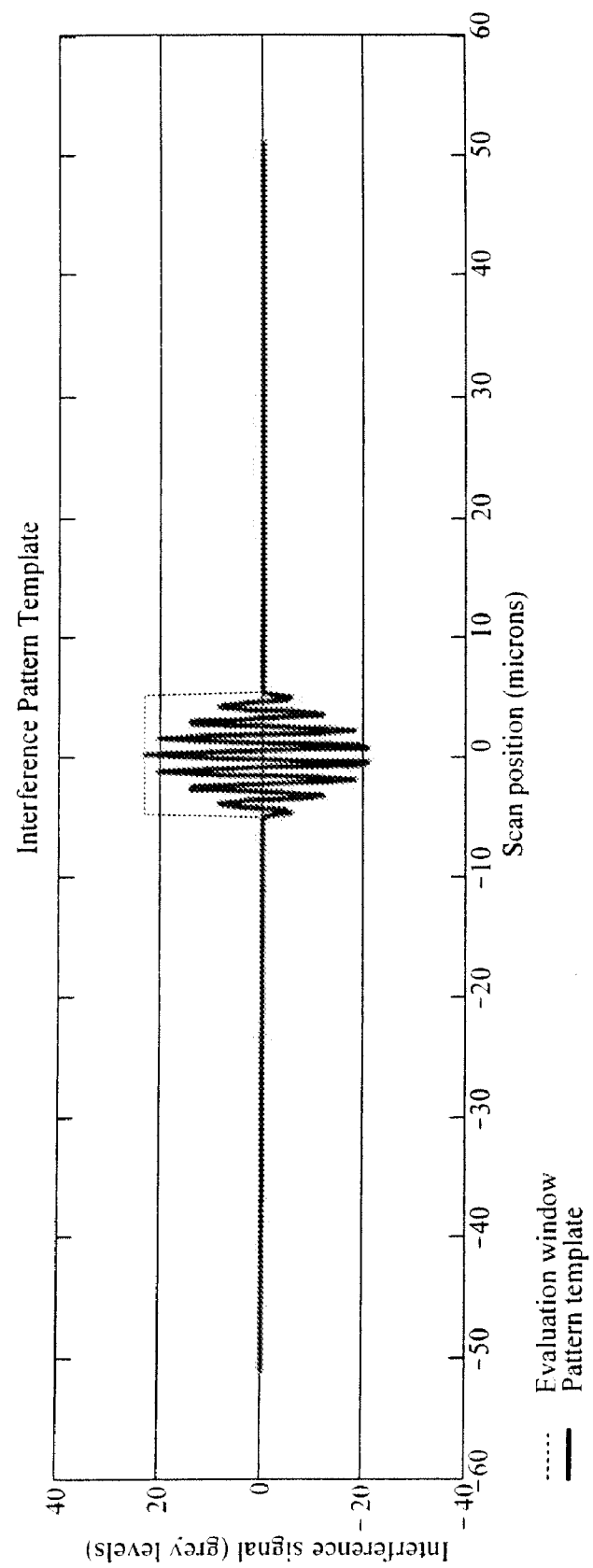
FIGS. 21 and 22 show interference template patterns for a bare Si substrate and a thin film structure with 1 micron of SiO2 on Si, respectively.
Figure 22:
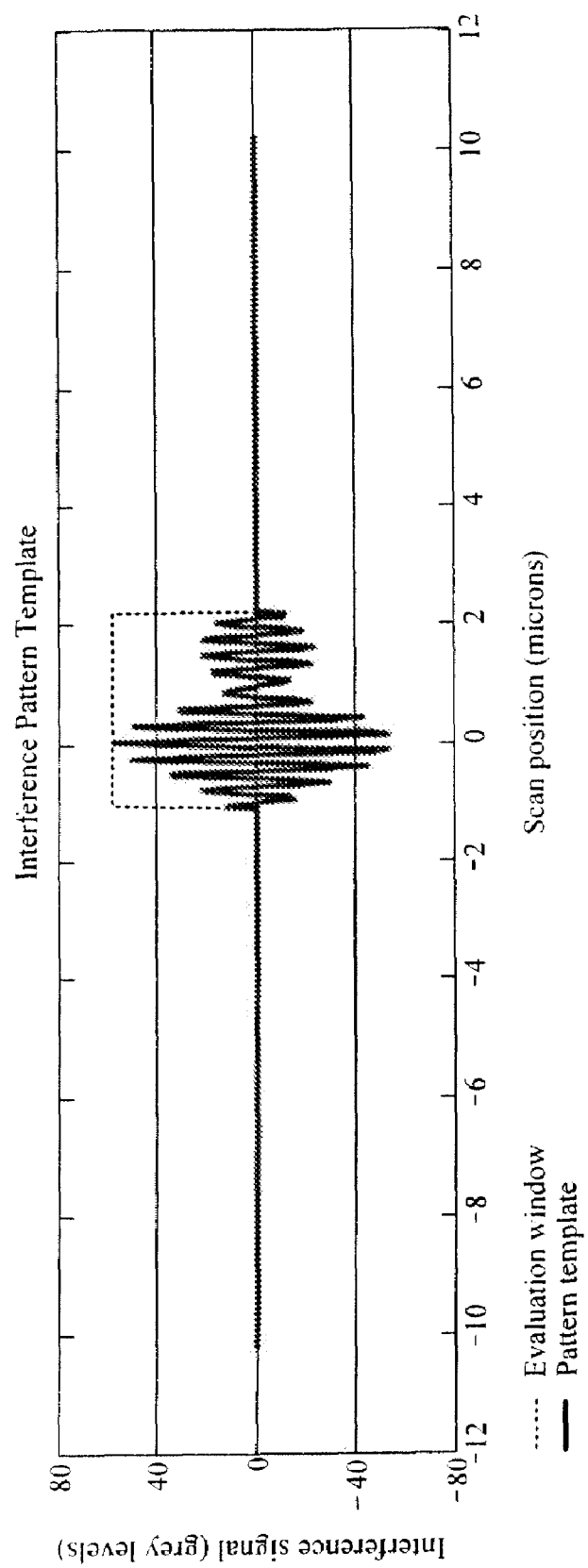
Figure 23:
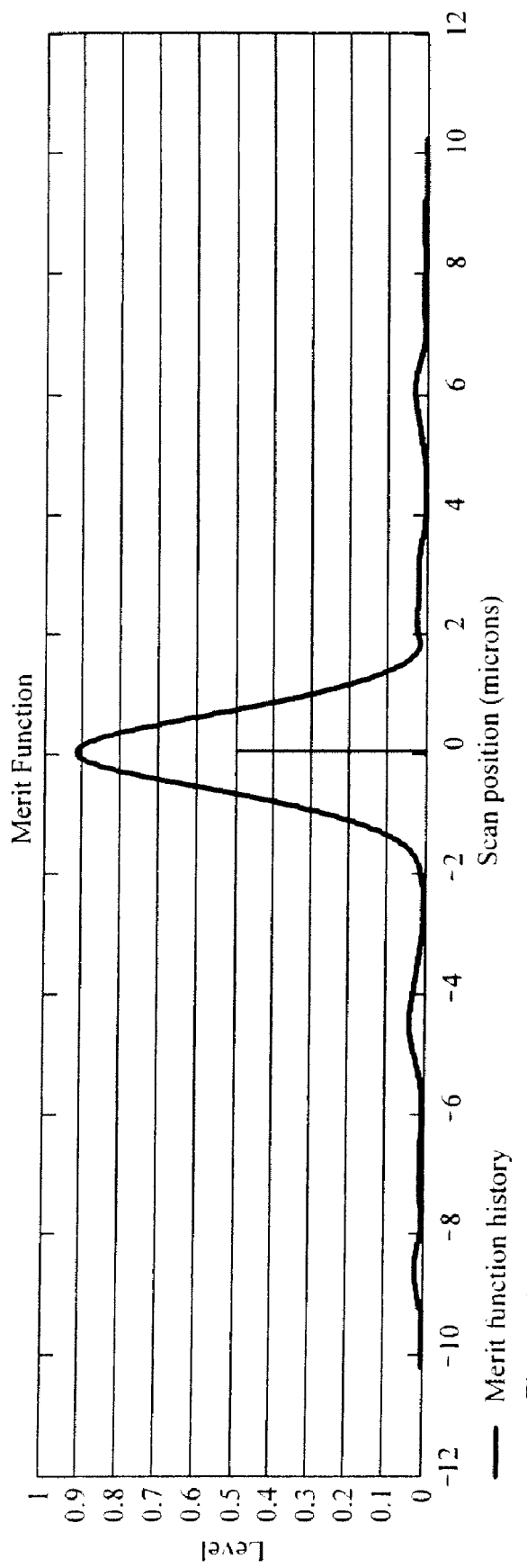
FIGS. 23 and 24 show the merit function as a function of scan positions for template functions in FIGS. 21 and 22, respectively.
Figure 24:
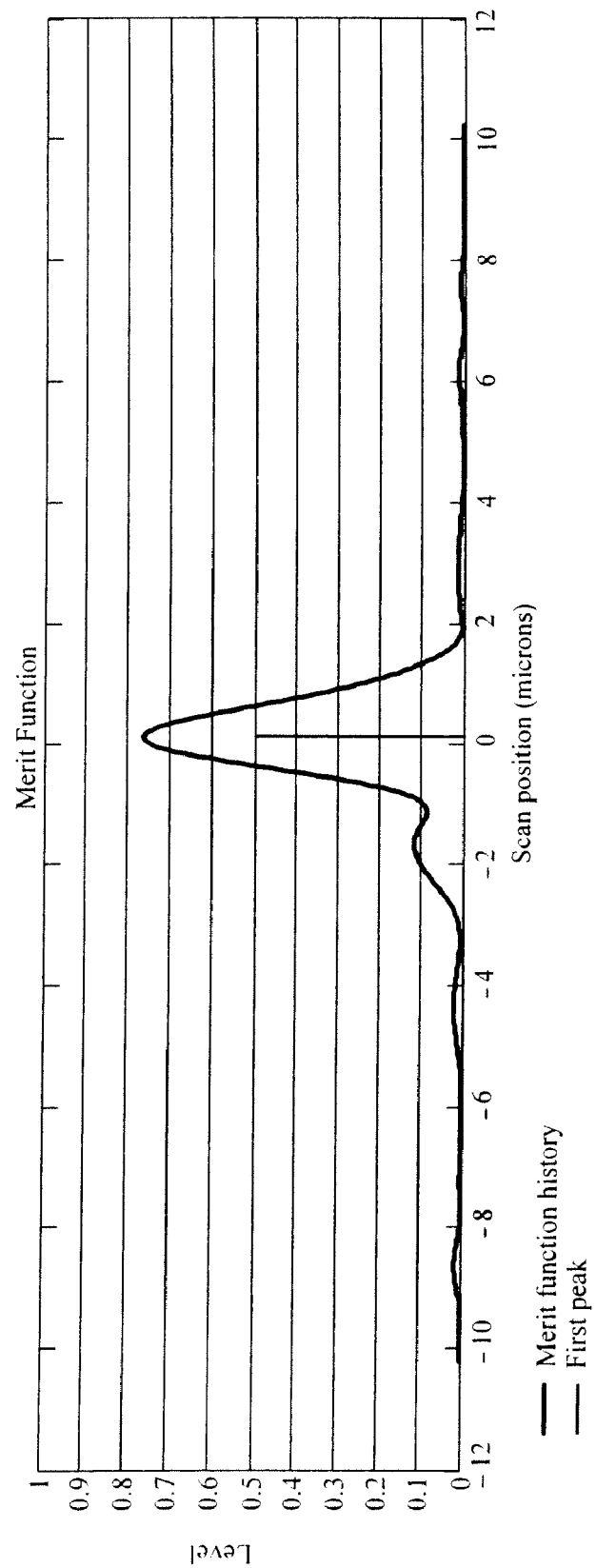

FIGS. 20-24 illustrate an example of the technique. FIG. 20 shows an actual scanning interferometry signal of a base Si substrate without a thin film. FIGS. 21 and 22 show interference template patterns for a bare Si substrate and a thin film structure with 1 micron of SiO2 on Si, respectively. FIGS. 23 and 24 show the merit function as a function of scan positions for template functions in FIGS. 21 and 22, respectively. The merit functions show that the interference template pattern for the bare substrate is a much better match (peak value 0.92) than that for the thin film template pattern (peak value 0.76) and therefore indicate that the test sample is a bare substrate. Moreover, the position of the peak in the merit function for the correct template pattern gives the relative surface height position for the test sample.

We now discussed certain examples of the technique that relate specifically to under-resolved surface features, such as patterned structures in front-end semiconductor manufacturing processes.

Figure 28:
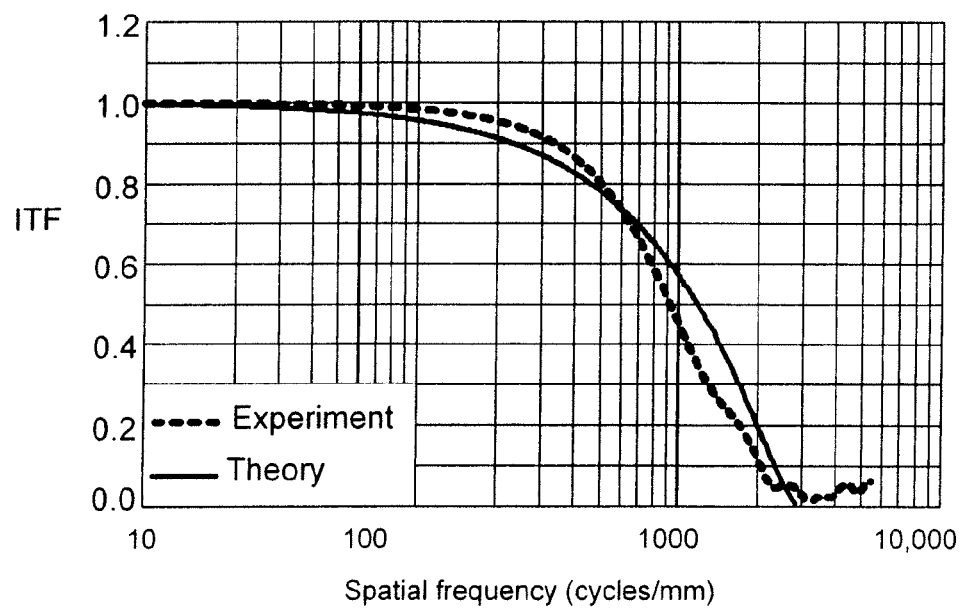
FIG. 28 is a graph showing theoretical and experimental instrument transfer functions of a typical white light scanning interferometer.

Although patterned by optical lithography, the front end or transistor-level semiconductor manufacturing process involves features that are far below the resolution limit of visible-wavelength microscopy. The smallest features, such as the transistor gates, are on the order of 45 nm wide, whereas the instrument transfer function of a typical scanning interferometer falls to zero for a 400-nm periodic structures. For example, FIG. 28 shows theoretical and experimental instrument transfer function for a white-light interference microscope using a 100×, 0.8 NA Mirau objective and incoherent illumination. The separation of the gates, shallow trench isolation (STI), wires and vias is often comparable to this lower limit; thus we see some of the surface structure, but not all. These under-resolved features cannot, therefore, be measured directly as height objects in the usual way with the white-light interference microscope. However, parameter monitoring (e.g. depth and width) of these features is often still possible if we understand how height variations below optical resolution affect the generation of the scanning interferometry data.

Figure 29A:
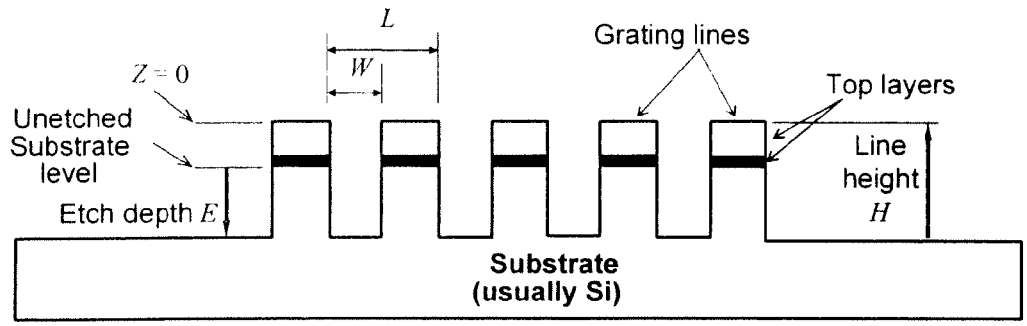
FIGS. 29a-c show schematic diagrams of the a grating structure and one embodiment of the under-resolved surface measurement technique disclosed herein.

FIG. 29a illustrates a simple cross-sectional model of a symmetric grating with unpatterned areas on either side. The y coordinate is parallel to the lines and into the figure, while the x coordinate is from left to right. The z=0 vertical position corresponds to the tops of the lines. A simple-minded scalar diffraction model and the Abbé principle confirms that when the grating linewidth L and spacing W fall below the resolution limits implied by FIG. 28, the grating lines blur together and the NewView cannot directly measure the lateral dimensions L and W nor the height H. However, this same scalar analysis shows that the apparent height of the etched area would indeed depend on the line height, width and spacing, even though the gate lines themselves would be indistinguishable. The exact dependence may be predicted to some degree by modeling, and refined by empirical evidence.

Figure 29B:
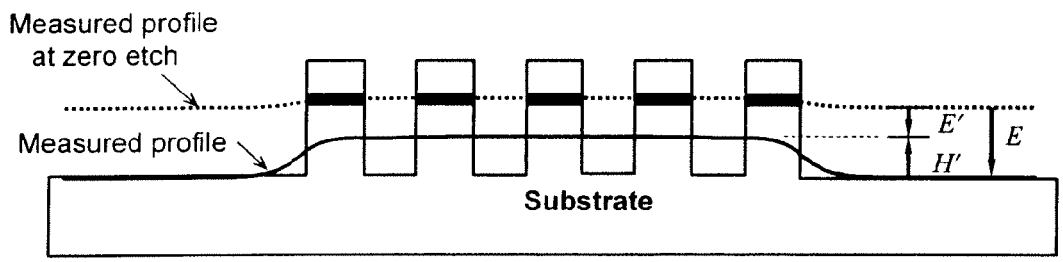

As noted previously, certain embodiments disclosed herein exploit the observation that the apparent height of the patterned area is related to the feature parameters of interest. We generate apparent surface height profiles using conventional processing interferometric techniques such as FDA. For the case of a pitch less than one-half wavelength, these profiles do not show the grating lines at all, or at most some echo of the lines, with an overall "averaged" height H' as shown in FIG. 29b, which shows simulated measured surface profiles superimposed on the grating structure. Consequently, we measure the height H' between the area over the lines and the area over the unpatterned bare substrate. This result may be referenced to the zero-etch height by subtracting the etch depth E to get a number E'=H'−E. Alternatively, if a zero-etch measured profile is available as in FIG. 29c (which likewise shows a simulated measured surface profile superimposed on the grating structure), the measured etch depth E' may be referenced directly to the zero-etch height (this is the more usual measurement scenario). Assuming that we know ahead of time the lateral dimensions L and W, the correct line height H follows from modeling the sensitivity of the entire measurement procedure to the parameter of interest. Alternatively, if we know H and L, we can infer W or some other parameter such as line shape.

Figure 29C:
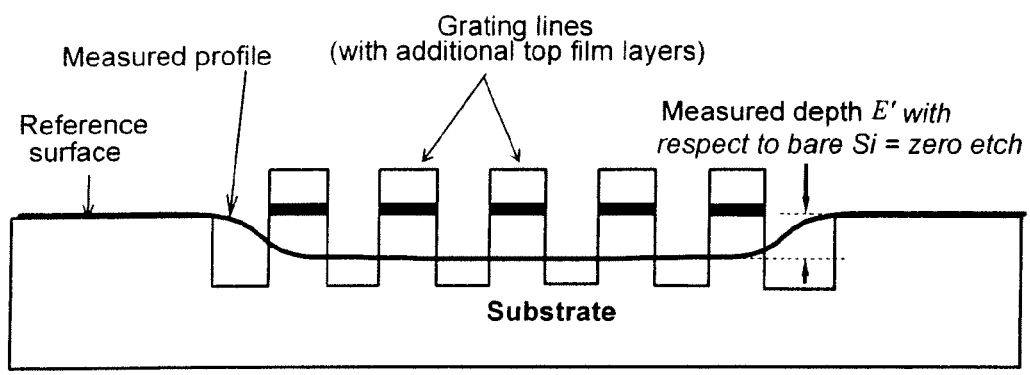

Using more rigorous modeling to consider polarization effects shows that the simulated profiles shown in FIGS. 29b and 29c represent qualitatively the behavior when the polarization is orthogonal to the gate lines (defined as the x direction). The parallel or y polarization, in contrast, is much more strongly influenced by the tops of the lines, in some cases appearing as if there were no spaces at all between the lines. This makes physical sense, in that polarization aligned with the gate lines generates currents that increase the influence of the tops of the lines at the expense of the areas between the lines. The sensitivity of the measurement to various structure parameters varies with polarizations; therefore, it may be possible to isolate specific parameters, such as etch depth, while minimizing sensitivity to others, such as linewidth.

Accordingly, embodiments of this measurement technique include: 1) use of a standard interference microscope with circular polarization and comparison of the step height to a neighboring, unpatterned area in the field of view (FOV) of known height relative to the pre-etched silicon; 2) as above, but use of x (orthogonal to lines) polarization to improve sensitivity to deep (>20 nm) trenches; 3) use of a linear polarization and comparison of heights of neighboring areas of orthogonally arranged grating lines; 4) comparison of the measured heights for both the x and y polarization states in the same field of view with respect to a common reference that is not polarization dependent, e.g., a smooth, flat area; and 5) comparison of the measured heights for both the x and y polarization states in the same field of view with respect to each other, for example by simultaneous capture of data for the two polarizations, or by interfering the polarization states directly. This approach may obviate any need for a separate reference on the object surface.

It should also be noted that the basic measurement principle is not limited to gratings, but may be extended to other structures.

Although a scalar or Abbé model provides some important insight into the basic measurement problem, quantitative analysis for a complex (multi-material), under-resolved surface structure can benefit from more rigorous modeling of the interferometry signals by solving Maxwell's Equations over a range of bandwidths and angles of incidence, such as the 2D approach based on the Rayleigh Hypothesis or the more rigorous RCWA approach, both of which were described above.

For example, the 2D Rayleigh approach explains the inversion result shown in FIG. 27 for circularly-polarized light incident on sample wafers on patterned structures. Specifically, in unpolarized or circularly polarized light, there is a competition between the x and y polarization states that leads to an inverse correlation. The inversion is attributable to the high sensitivity to etch depth of the x polarization reflected intensity, causing a modulation in the contribution of the x polarization compared to the y polarization. Because these two polarizations report different depths, the balance between their reflected strengths can lead to this nonlinear correlation between the apparent grating modulation depth and the actual grating modulation depth. The 2D Rayleigh calculation showed that such an inversion could take place with under-resolved grating lines.

Figure 30A:
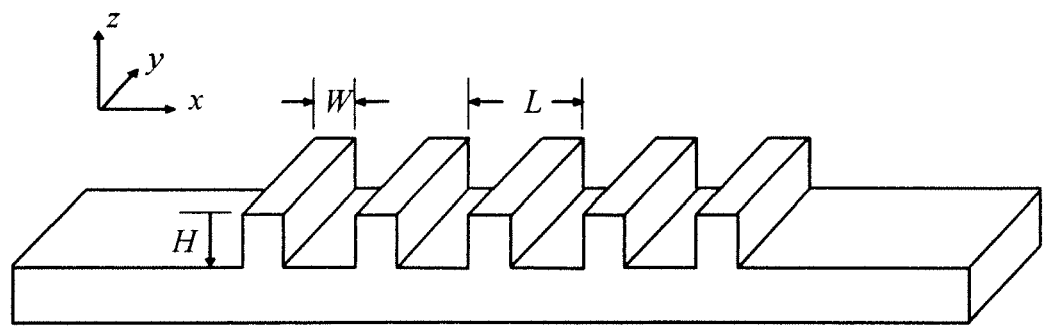
FIG. 30a shows a schematic of a model structure of 5 pure Si grating lines (no top film layers), width W=120 nm and pitch L=320 nm.
Figure 30B:
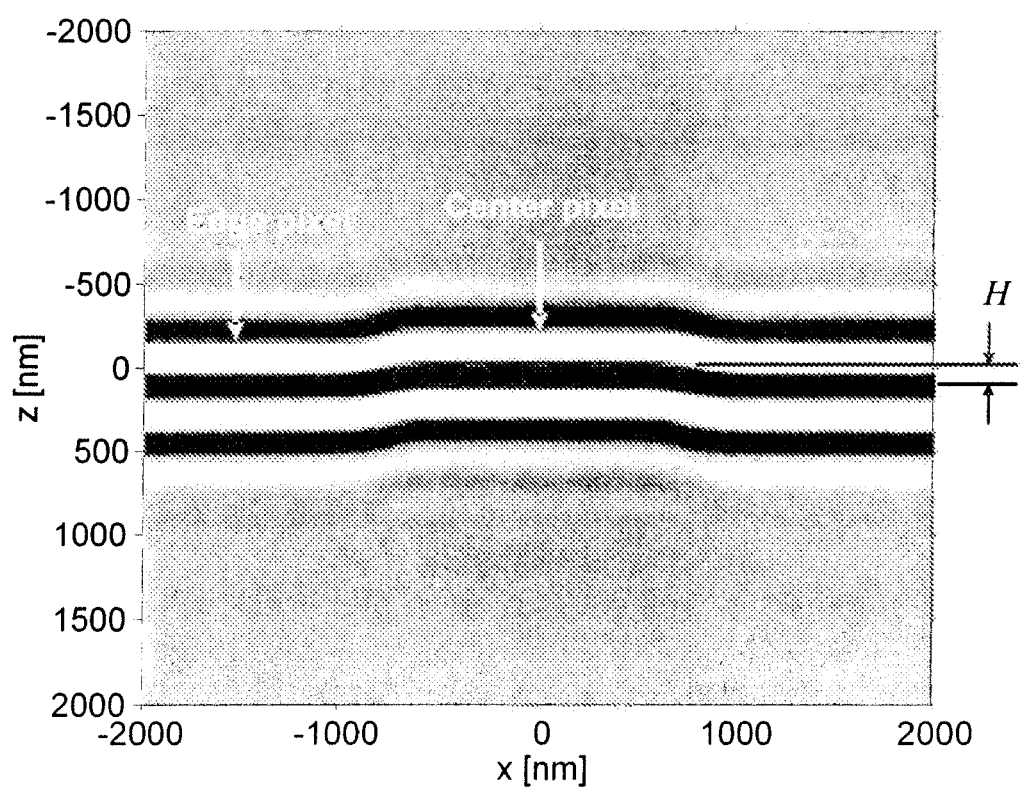
FIG. 30b shows a rigorous coupled wave analysis (RCWA) showing the scanning interferometry signal (in z-direction) for the model structure. This is for a y polarization, parallel to the lines, which is more sensitive to the tops of the lines than the areas.

In another example, a rigorous RCWA approach was used to model a pure silicon 5-line grating without top film layers, with lines having a width W=120 nm and pitch L=320 nm. A schematic of the grating is shown in FIG. 30a. The output of the simulation, shown in FIG. 30b, is a simulated SWLI signal (z-direction) for each of a line of pixels (x-direction). FIG. 30b shows the results only for y polarization, parallel to the lines, which is more sensitive to the tops of the lines than the areas or trenches between the lines. If we look at the output for a single pixel as in FIGS. 31a and 31b for the x and y polarizations, respectively, we recognize the familiar white-light interference pattern, approximated by a carrier fringe pattern modulated by an envelope or fringe contrast function. Noteworthy is the somewhat distorted x-polarization signal (FIG. 31a), which reveals a competition between the unresolved tops of the grating lines and the trenches in between, leading to a weakened signal with envelope structure and a general shift towards the left, which corresponds to lower heights.

Figure 32A:
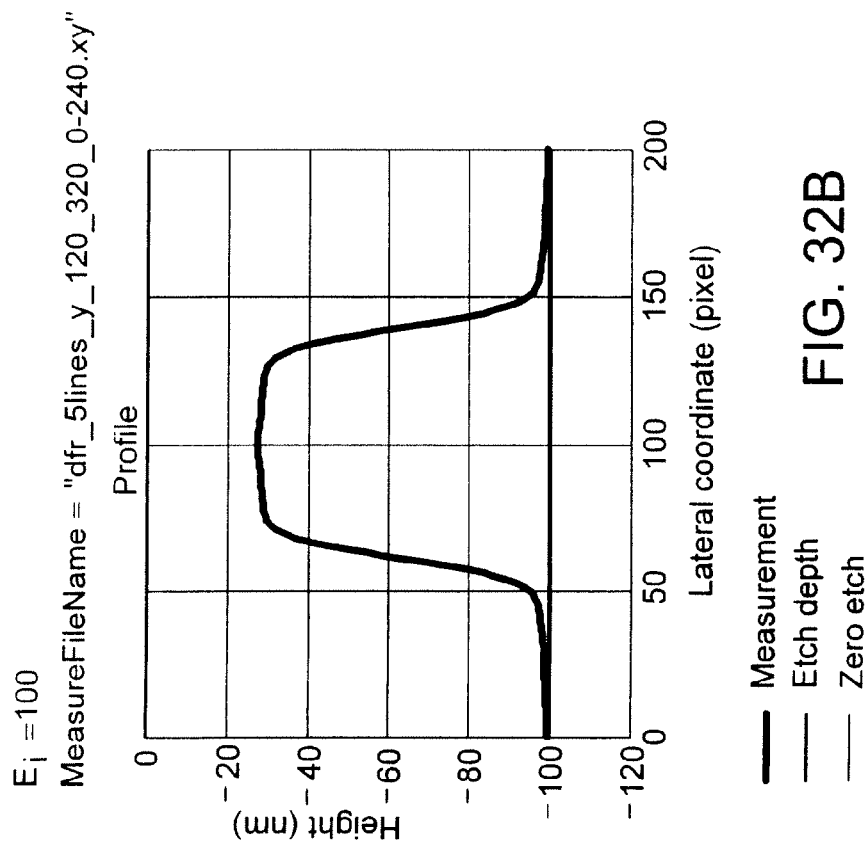
FIGS. 32a and 32b are surface height profiles derived from an FDA analysis of the signals in FIG. 30 for the x- (orthogonal to grating lines) and y-polarizations (parallel to grating lines), respectively.
Figure 32B:
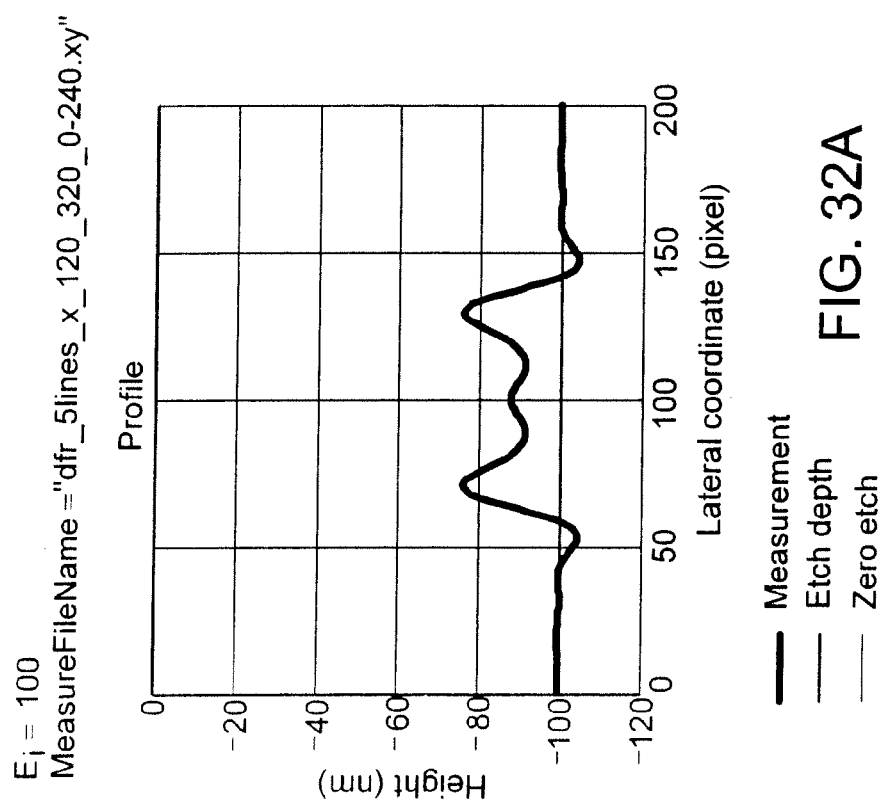

An FDA analysis of these signals generates the apparent surface profiles shows in FIGS. 32a and 32b for the x- (orthogonal to grating lines) and y-polarizations (parallel to grating lines), respectively. To relate this to a step height measurement, we compare the center pixel to an edge pixel to determine H', the edge pixel presumably marking the true etch depth E of the substrate. The measured substrate etch depth is then E'=H−E. This is the value that we would measure when referencing to an unetched substrate area. We rely on modeling or empirical data to translate the apparent etch depth to the actual depth.

Figures 33A, 33B:
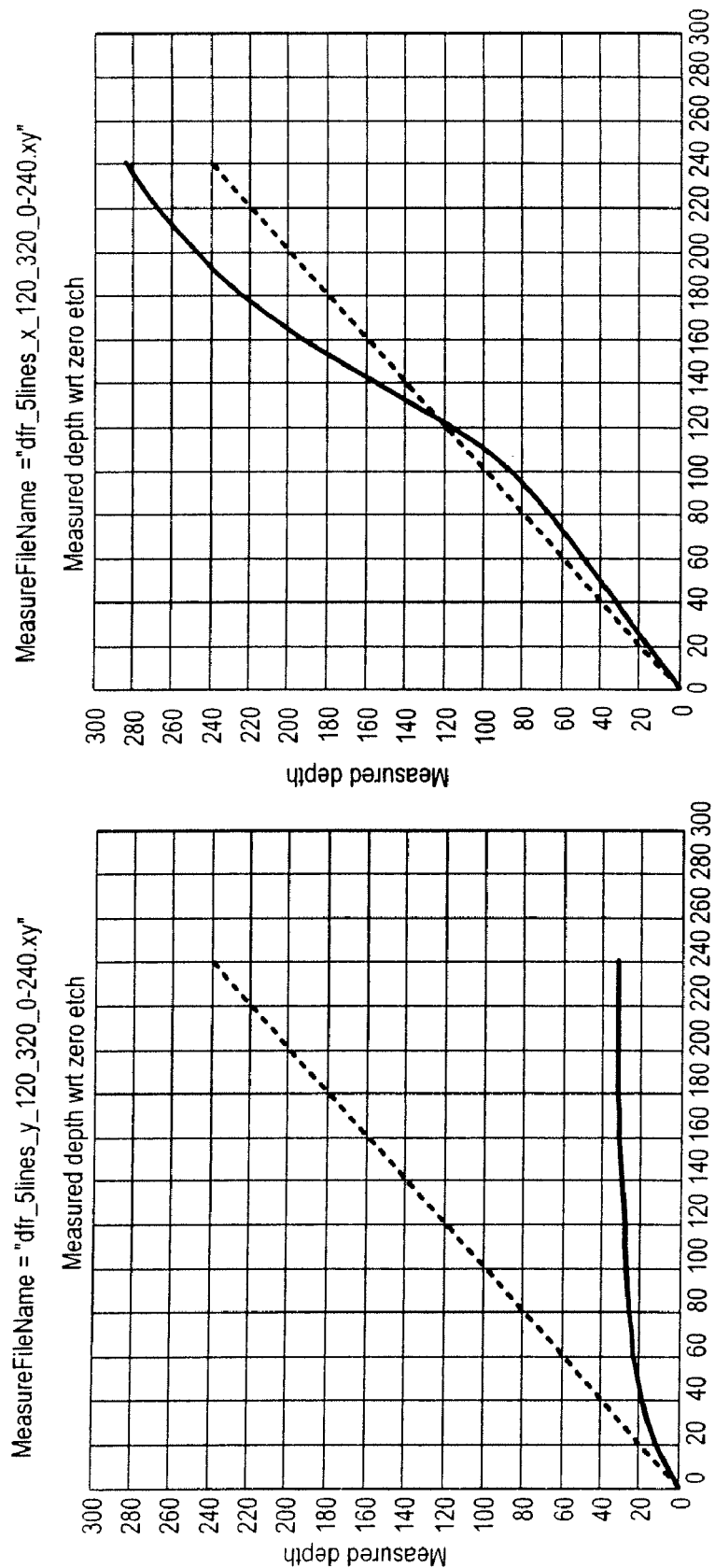
FIGS. 33a and 33b are graphs showing the results of the RCWA analysis for the apparent etch depth E'=H'-E as extracted from simulated scanning interferometry data as a function of different actual etch depth E for the y-polarization (parallel to grating lines) and x- (orthogonal to grating lines), respectively. The E'=E line is for reference.
Figures 34A, 34B:
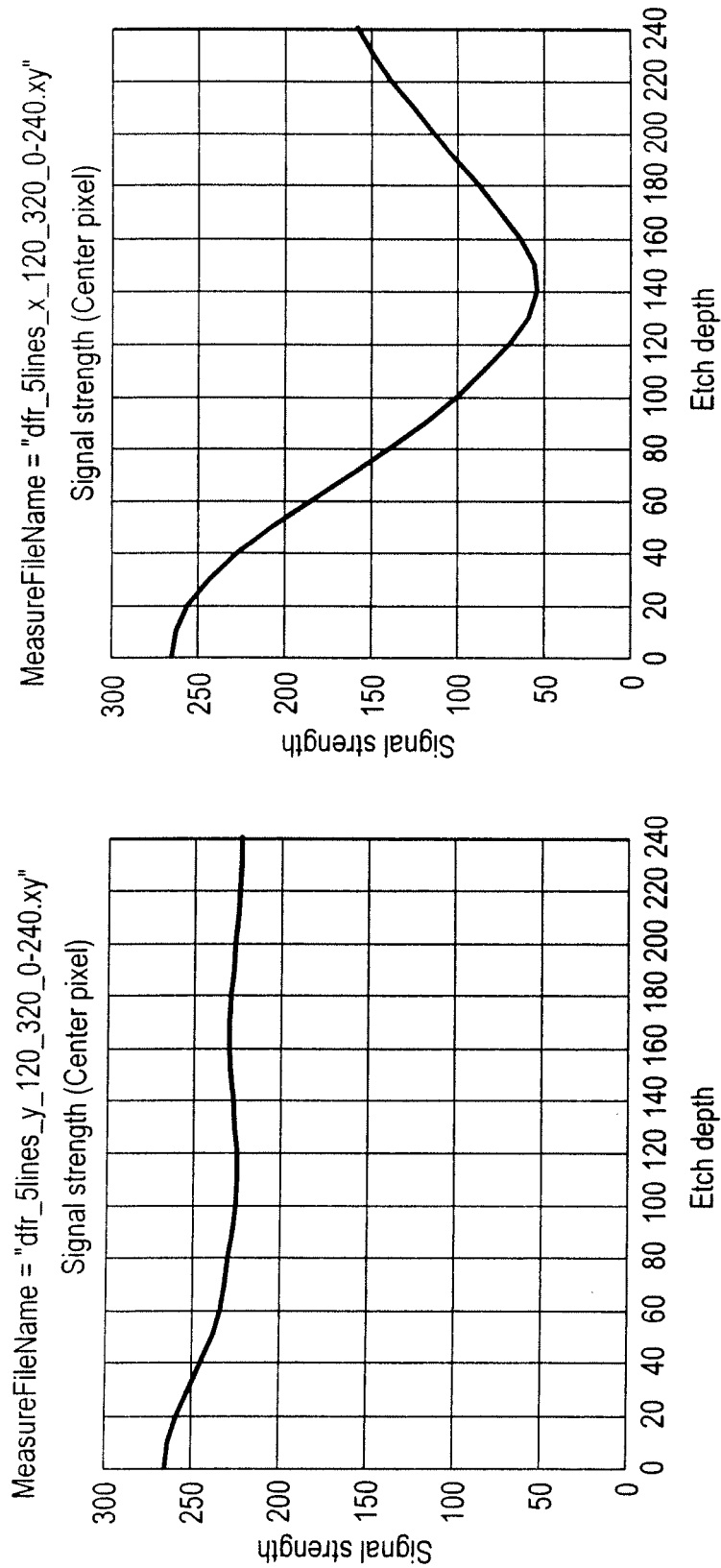
FIGS. 34a and 34b are graphs showing the corresponding signal strength for the different actual etch depths E for the y-polarization (parallel to grating lines) and x- (orthogonal to grating lines), respectively.

FIGS. 33a and 33b show the results of the RCWA analysis for the apparent etch depth E'=H'−E as extracted from simulated scanning interferometry data as a function of different actual etch depth E for the y-polarization (parallel to grating lines) and x- (orthogonal to grating lines), respectively. The E'=E line is for reference. FIGS. 34a and 34b show the corresponding signal strength for the different actual etch depths E for the y-polarization (parallel to grating lines) and x- (orthogonal to grating lines), respectively. The results show the expected behavior for the two polarization states. Clearly the preferable configuration for etch depth sensitivity is the x polarization, assuming that we can stay clear of the reflected intensity minimum at 145 nm etch depth shown in FIG. 34b.

Figure 35:
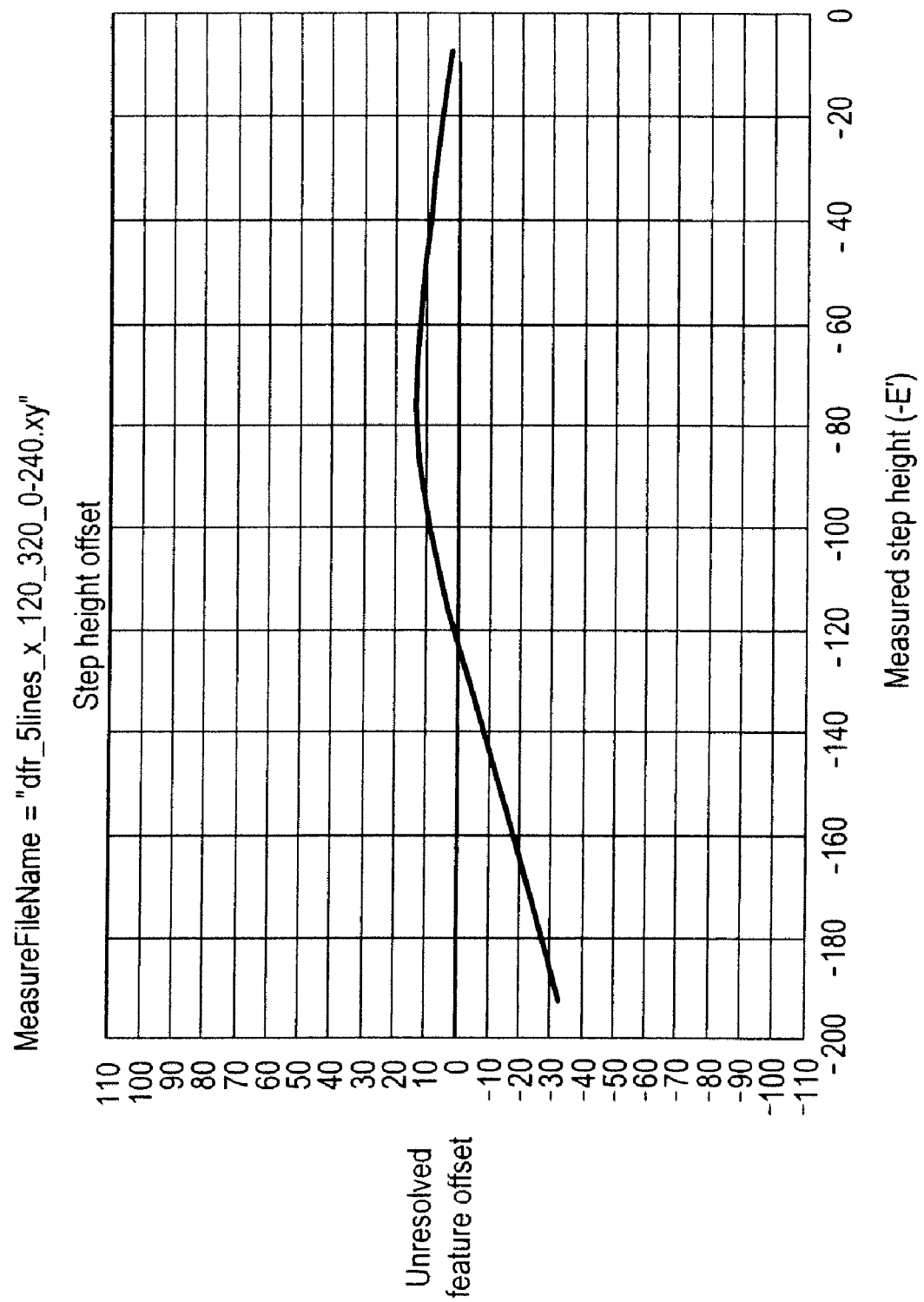
FIG. 35 is an alternative graph of the same data as in FIG. 33b that shows the measurement bias or offset E–E' as a function of the measured step height –E' for the silicon grating.

The difference between the measured height E' and etch depth E is in some sense the bias or offset resulting from the unresolved grating lines, including the top film layers. In the ideal case, the instrument would simply disregard the presence of the lines, assuming that the substrate etch depth were the only parameter of interest. FIG. 35 is an alternative graphing of the same data as in FIG. 33b, showing that for the x polarization, the bias is modest and does not change rapidly with etch depth. Specifically, it shows the measurement bias or offset E−E' as a function of the measured step height −E' for the silicon grating.

Figure 36:
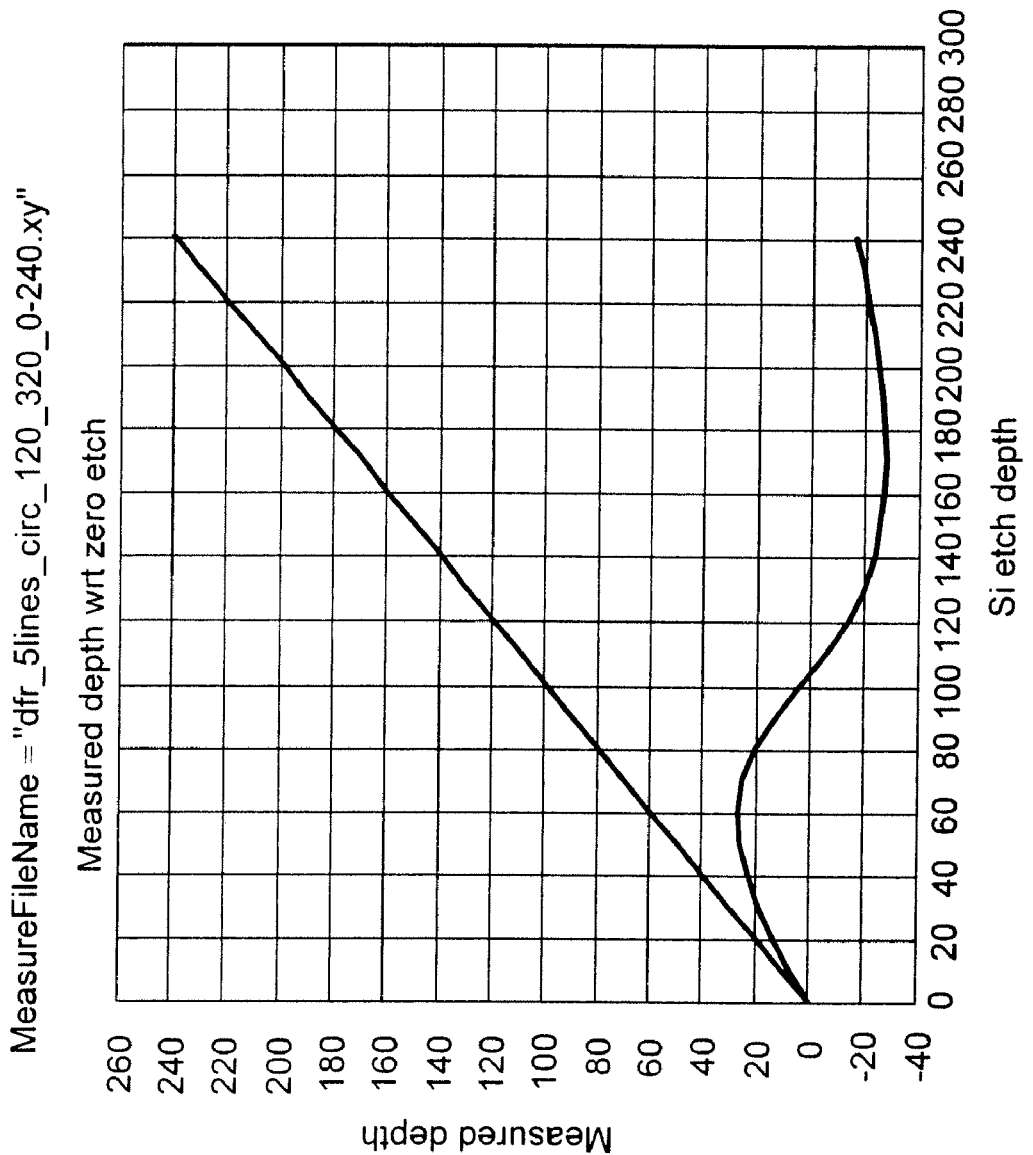
FIG. 36 is a graph that shows the RCWA predictions for the measured etch depth E'=H'-E as a function of the actual etch depth E for the silicon grating, with circularly polarized light, in comparison with a one-to-one correspondence line.

FIG. 36 shows the expected RCWA results for circularly polarized light for a pure Si grating. Specifically, it shows the RCWA predictions for the measured etch depth E'=H'−E as a function of the actual etch depth E for the silicon grating, with circularly polarized light, in comparison with a one-to-one correspondence line. Of note is the generally poor response of the system, and in particular, the inverse correlation between measured and actual etch depth between 60 and 170 nm. This is the same phenomenon predicted from the Rayleigh hypothesis and shown in FIG. 27 and described above. Above 100 nm etch, the measured depth is negative, meaning that the etched silicon appears to rise above the unetched silicon. The area looks like a protrusion rather than a recess.

Figure 37A:
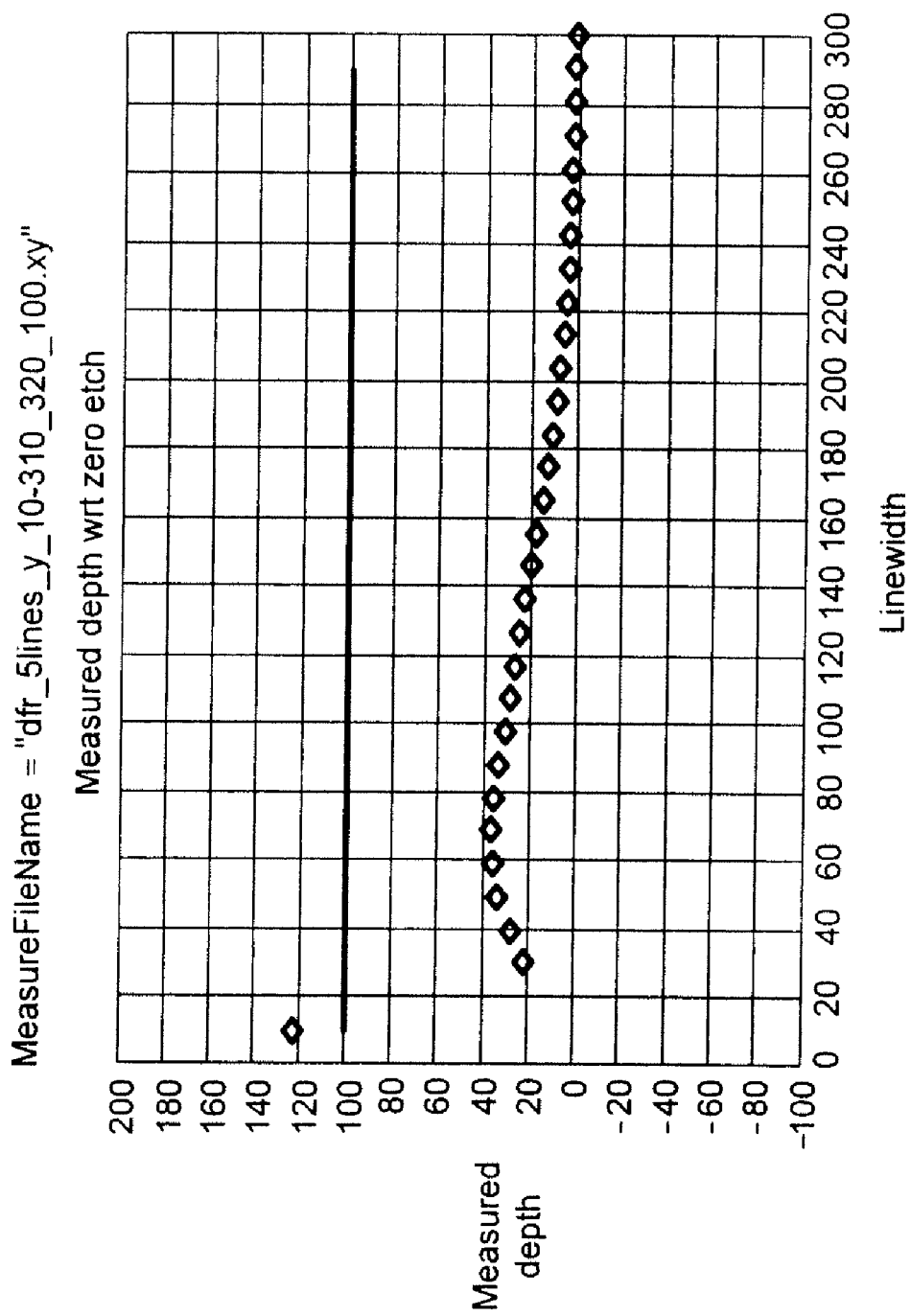
FIGS. 37a and 37b are graphs that show the RCWA predictions for the measured (apparent) etch depth E'=H'-E as a function of the feature width W for an etch depth E=100 nm and pitch L=320 nm, for the five-line silicon grating for y- and x-polarization, respectively. The solid line marks the etch depth in both graphs, for reference.
Figure 37B:
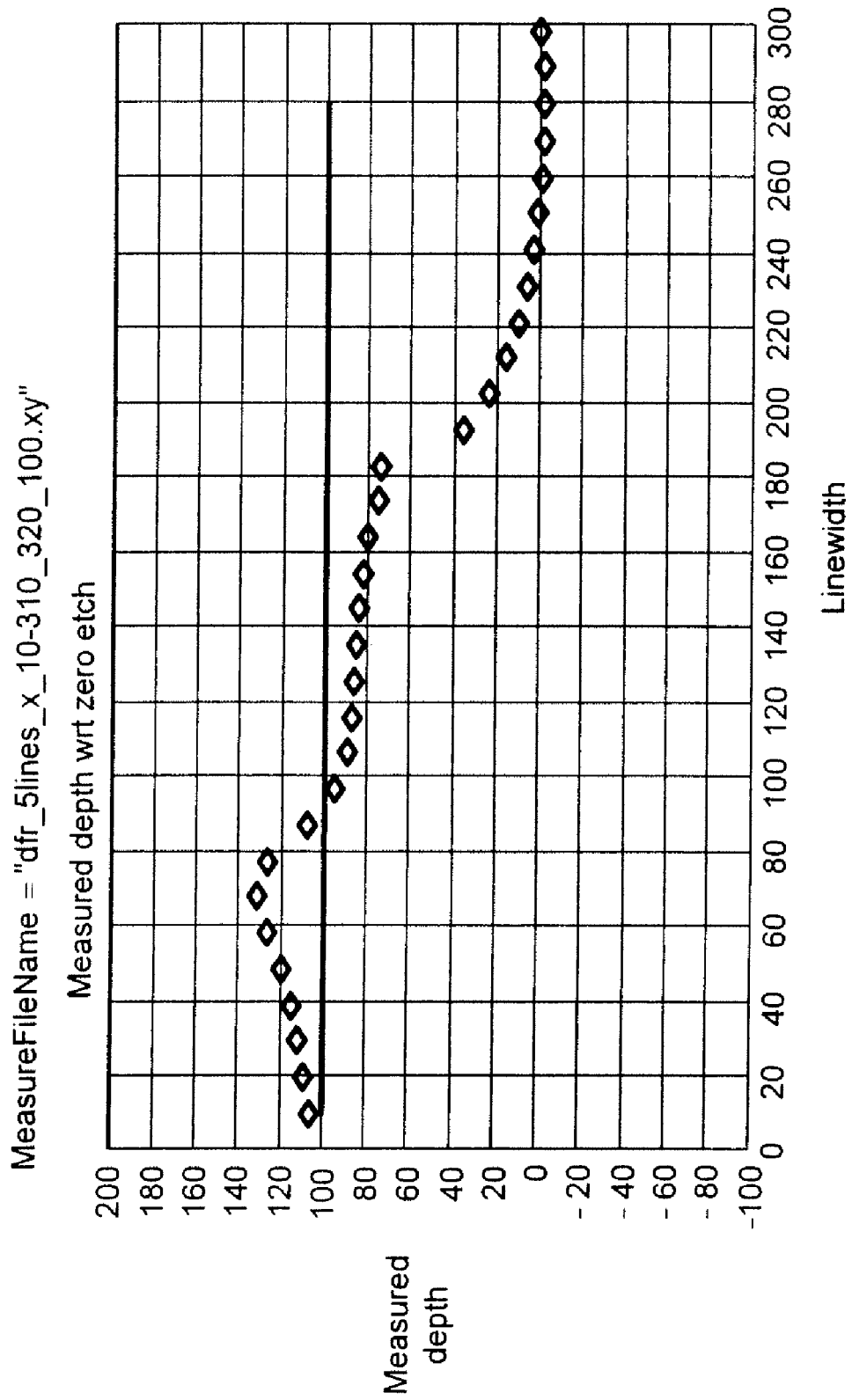

FIGS. 37a and 37b show the RCWA predictions for the measured (apparent) etch depth E'=H'−E as a function of the feature width W for an etch depth E=100 nm and pitch L=320 nm, for the five-line silicon grating for y- and x-polarization, respectively. The solid line marks the etch depth in both graphs, for reference. The graphs shows some interesting behavior, including relative insensitivity to linewidth over broad ranges. These results imply that for linewidths between 100 and 180 nm, for example, the x-polarization measurement is far more sensitive to etch depth than to linewidth, at least for this combination of parameters (compare with FIG. 33). The y polarization, however, shows a greater sensitivity to linewidth than to etch depth, although the sensitivity is weak in either case.

Qualitatively the reflectivity minimum in FIG. 33b and the inverse correlation in FIG. 36 can be understood as resulting from the situation where the depth of the grating corresponds causes a phase flip related to the quarter-wave anti-reflection condition. Thus, if it is desired to move to a more linear portion of the correlation curve, the wavelength of the light used in the interferometer can be adjusted relative to the quarter-wavelength condition, where the quarter-wavelength condition is met when the product of the grating depth and the index of the material between the lines (e.g., for the present structure, n=1 for air) equals the sum of a quarter of the light wavelength and any integer multiple (including zero) of half the light wavelength. On the other hand, the presence of a reflectivity minimum (or more generally, reflectivity information derived from the interferometry signal strength) can be used alone, or in conjunction with the apparent surface profile, as the information that is compared to expected information for different models of the sample to determine information about the under-resolved surface features.

While the above example pertained specifically to a patterned structure in one-dimension, the general principles of the technique can be extended to other types of under-resolved surface patterns, such as discrete step heights and two-dimensional patterned structures. The underlying principle is that even though such surface features may be under-resolved they do contribute to both the interferometry signal for individual pixels and collective information extracted from interferometry signals from multiple pixels. Thus, experimental derived information can be compared to models that are parametrized by different values for under-resolved features of interest, with the best comparison yielding the corresponding value of the feature of interest.

Furthermore, in other examples, the different portions of the grating may have different modulations depths or may be formed over different material compositions. For example, a grating structure can be formed on a silicon substrate that includes regions of silicon dioxide. Furthermore, the regions of the grating between the silicon dioxide can be etched to different depths. In such embodiments, the information that is compared to the models can be, for example, differences in apparent surface height between different resolved regions of the grating. In other words, for example, although the individual grating lines may not be resolved, the portion of the grating formed over the silicon dioxide may be distinguishable from other portions of the grating.

Figure 38:
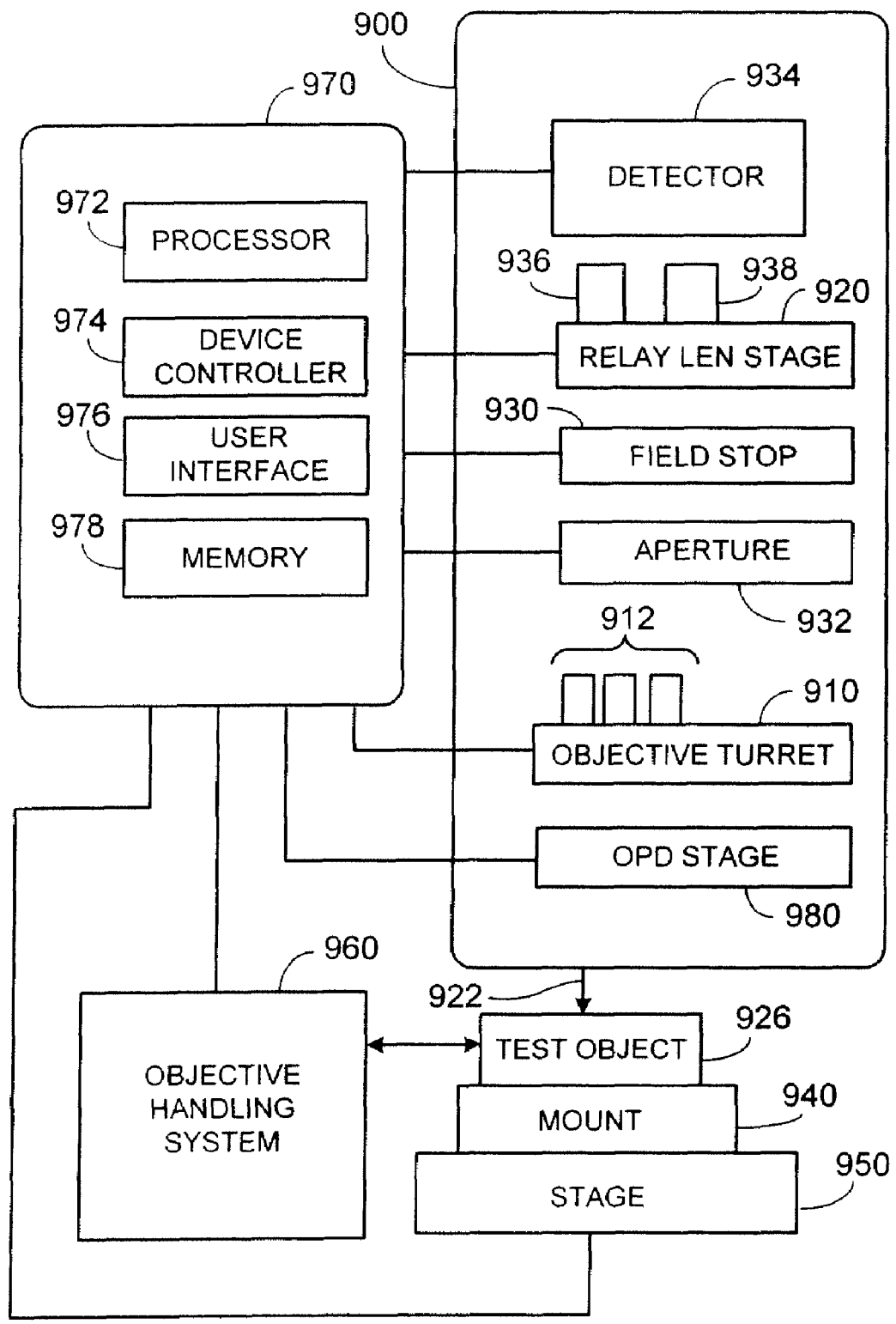
FIG. 38 is a schematic diagram of an interferometry system showing how various components of the system can be under automated control.

FIG. 38 shows a schematic diagram of how various components in interferometry system 900 used to generate the interferometry signals can be automated under the control of electronic processor 970, which, in the presently described embodiment, can include an analytical processor 972 for carrying out mathematical analyses (e.g., comparison to the model libraries), device controllers 974 for controlling various components in the interferometry system, a user interface 976 (e.g., a keyboard and display), and a storage medium 978 for storing information (e.g., library models and calibration information), data files, and/or automated protocols. Interferometry system 900 generally directs test light 922 to test object 926, which is secured to mount 940 on a stage 950.

First, the system can include a motorized turret 910 supporting multiple objectives 912 and configured to introduce a selected objective into the path of the input light. One or more of the objectives can be interference objectives, with the different interference objectives providing different magnifications. Furthermore, in certain embodiments, the interference objectives can include one (or more) polarization elements (e.g., a linear polarizer) attached to it (for example, to illuminate a grating pattern with light polarized orthogonal to the grating lines). In such cases, it the orientation of the polarization element can be also be under automated control so as to, for example, align the polarization of the illumination light with respect the grating lines of a patterned structure. Moreover, one or more of the objectives can be a non-interferometric objective (i.e., one without a reference leg), each with a different magnification, so that system 900 can also operate in a conventional microscope mode for collecting optical images of the test surface. Turret 910 is under the control of electronic processor 970, which selects the desired objective according to user input or some automated protocol.

Next, the system includes a motorized stage 920 (e.g., a tube lens holder) for supporting relay lenses 936 and 938. Such a stage can be used for selecting between a profiling mode, such as that generally contemplated in the present application, or an ellipsometry or reflectometry mode in which the pupil plane is imaged to the detector, as described in U.S. Patent Publication No. US-2006-0158659-A1 entitled "INTERFEROMETER FOR DETERMINING CHARACTERISTICS OF AN OBJECT SURFACE" by Colonna de Lega et al., the contents of which are incorporated by reference. Motorized stage 920 is under the control of electronic processor 970, which selects the desired relay lens according to user input or some automated protocol. In other embodiments, in which a translation stage is moved to adjust the position of the detector to switch between the first and second modes, the translation is under control of electronic processor. Furthermore, in those embodiments with multiple detection channels, each detector is coupled to the electronic processor 970 for analysis.

Furthermore, the system can include motorized apertures 930 and 932 under control of electronic processor 970 to control the dimensions of the field stop and aperture stop, respectively. Again the motorized apertures are under the control of electronic processor 970, which selects the desired settings according to user input or some automated protocol.

Also, translation stage 980, which is used to vary the relative optical path length between the test and reference legs of the interferometer, is under the control electronic processor 970. The translation stage can be coupled to adjust the position of the interference objective relative to a mount 940 for supporting test object 926. Alternatively, in further embodiments, the translation stage can adjust the position of the interferometry system as a whole relative to the mount, or the translation stage can be coupled to the mount, so it is the mount that moves to vary the optical path length difference.

Furthermore, a lateral translation stage 950, also under the control of electronic processor 970, can be coupled to the mount 940 supporting the test object to translate laterally the region of the test surface under optical inspection. In certain embodiments, translation stage 950 can also orient mount 940

(e.g., provide tip and tilt) so as to align the test surface normal to the optical axis of the interference objective.

Finally, an object handling station 960, also under control of electronic processor 970, can be coupled to mount 940 to provide automated introduction and removal of test samples into system 900 for measurement. For example, automated wafer handling systems known in the art can be used for this purpose. Furthermore, if necessary, system 900 and object handling system can be housed under vacuum or clean room conditions to minimize contamination of the test objects.

The resulting system provides great flexibility for providing various measurement modalities and procedures. For example, the system can first be configured in the microscope mode with one or more selected magnifications to obtain optical images of the test object for various lateral positions of the object. Such images can be analyzed by a user or by electronic processor 970 (using machine vision techniques) to identify certain regions (e.g., specific structures or features, landmarks, fiducial markers, defects, etc.) in the object. Based on such identification, selected regions of the sample can then be studied in the ellipsometry mode to determine sample properties (e.g., refractive index, underlying film thickness(es), material identification, etc.).

When used in conjunction with automated object handling system 960, the measurement procedure can be repeated automatically for a series of samples. This could be useful for various process control schemes, such as for monitoring, testing, and/or optimizing one or more semiconductor processing steps.

For example, the system can be used in a semiconductor process for tool specific monitoring or for controlling the process flow itself. In the process monitoring application, single/multi-layer films are grown, deposited, polished, or etched away on unpatterned Si wafers (monitor wafers) by the corresponding process tool and subsequently the thickness and/or optical properties are measured using the interferometry system disclosed herein. The average, as well as within wafer uniformity, of thickness (and/or optical properties) of these monitor wafers are used to determine whether the associated process tool is operating with targeted specification or should be retargeted, adjusted, or taken out of production use.

In the process control application, latter single/multi-layer films are grown, deposited, polished, or etched away on patterned Si, production wafers by the corresponding process tool and subsequently the thickness and/or optical properties are measured with the interferometry system disclosed herein (for example, by using the ellipsometry mode, the profiling mode, or both). Production measurements used for process control typical include a small measurement site and the ability to align the measurement tool to the sample region of interest. This site may consists of multi-layer film stack (that may itself be patterned) and thus requires complex mathematical modeling in order to extract the relevant physical parameters. Process control measurements determine the stability of the integrated process flow and determine whether the integrated processing should continue, be retargeted, redirected to other equipment, or shut down entirely.

Specifically, for example, the interferometry system disclosed herein can be used to monitor the following equipment: diffusion, rapid thermal anneal, chemical vapor deposition tools (both low pressure and high pressure), dielectric etch, chemical mechanical polishers, plasma deposition, plasma etch, lithography track, and lithography exposure tools. Additionally, the interferometry system disclosed herein can be used to control the following processes: trench and isolation, transistor formation, as well as interlayer dielectric formation (such as dual damascene). The methods and systems described above can be particularly useful in semiconductor applications. Additional embodiments of the invention include applying any of the measurement techniques described above to address any of the semiconductor applications described below, and systems for carrying out both the measurement techniques and the semiconductor applications.

It is presently of considerable interest in the semiconductor industry to make quantitative measurements of surface topography. Due to the small size of typical chip features, the instruments used to make these measurements typically must have high spatial resolution both parallel and perpendicular to the chip surface. Engineers and scientists use surface topography measuring systems for process control and to detect defects that occur in the course of manufacturing, especially as a result of processes such as etching, polishing, cleaning and patterning.

For process control and defect detection to be particularly useful, a surface topography measuring system should have lateral resolution comparable to the lateral size of typical surface features, and vertical resolution comparable to the minimum allowed surface step height. Typically, this requires a lateral resolution of less than a micron, and a vertical resolution of less than 1 nanometer. It is also preferable for such a system to make its measurements without contacting the surface of the chip, or otherwise exerting a potentially damaging force upon it, so as to avoid modifying the surface or introducing defects. Further, as it is well-known that the effects of many processes used in chip making depend strongly on local factors such as pattern density and edge proximity, it is also important for a surface topography measuring system to have high measuring throughput, and the ability to sample densely over large areas in regions which may contain one or many surface features of interest.

It is becoming common among chip makers to use the so-called 'dual damascene copper' process to fabricate electrical interconnects between different parts of a chip. This is an example of a process which may be effectively characterized using a suitable surface topography system. The dual damascene process may be considered to have five parts: (1) an interlayer dielectric (ILD) deposition, in which a layer of dielectric material (such as a polymer, or glass) is deposited onto the surface of a wafer (containing a plurality of individual chips); (2) chemical mechanical polishing (CMP), in which the dielectric layer is polished so as to create a smooth surface, suitable for precision optical lithography, (3) a combination of lithographic patterning and reactive ion etching steps, in which a complex network is created comprising narrow trenches running parallel to the wafer surface and small vias running from the bottom of the trenches to a lower (previously defined) electrically conducting layer, (4) a combination of metal deposition steps which result in the trenches and vias being over-filled with copper, and (5) a final chemical mechanical polishing (CMP) step in which the excess copper is removed, leaving a network of copper filled trenches (and possibly vias) surrounded by dielectric material.

Typically the thickness of the copper in the trench areas (i.e., the trench depth), and the thickness of the surrounding dielectric lie in a range of 0.2 to 0.5 microns. The width of the resulting trenches may be in a range of from 100 to 100,000 nanometers, and the copper regions within each chip may in some regions form regular patterns such as arrays of parallel lines, and in others they may have no apparent pattern. Likewise, within some regions the surface may be densely covered with copper regions, and in other regions, the copper regions may be sparse. It is important to appreciate that the polishing rate, and therefore the remaining copper (and dielectric) thickness after polishing, depends strongly and in a complex manner on the polishing conditions (such as the pad pressure and polishing slurry composition), as well as on the local detailed arrangement (i.e., orientation, proximity and shape) of copper and surrounding dielectric regions.

This 'position dependent polishing rate' is known to give rise to variable surface topography on many lateral length scales. For example, it may mean that chips located closer to the edge of a wafer on aggregate are polished more rapidly than those located close to the center, creating copper regions which are thinner than desired near the edges, and thicker than desired at the center. This is an example of a 'wafer scale' process nonuniformity—i.e., one occurring on length scale comparable to the wafer diameter. It is also known that regions which have a high density of copper trenches polish at a higher rate than nearby regions with low copper line densities. This leads to a phenomenon known as 'CMP induced erosion' in the high copper density regions. This is an example of a 'chip scale' process non-uniformity—i.e., one occurring on a length scale comparable to (and sometimes much less than) the linear dimensions of a single chip. Another type of chip scale nonuniformity, known as 'dishing', occurs within single copper filled trench regions (which tend to polish at a higher rate than the surrounding dielectric material). For trenches greater than a few microns in width dishing may become severe with the result that affected lines later exhibit excessive electrical resistance, leading to a chip failure.

CMP induced wafer and chip scale process nonuniformities are inherently difficult to predict, and they are subject to change over time as conditions within the CMP processing system evolve. To effectively monitor, and suitably adjust the process conditions for the purpose of ensuring that any non-uniformities remain within acceptable limits, it is important for process engineers to make frequent non-contact surface topography measurements on chips at a large number and wide variety of locations. This is possible using embodiments of the interferometry techniques described above.

The interferometer embodiments described above include an interference objective of the Mirau-type and of the Linnik-type. In the Mirau, the beam splitter in the interference objective directs the reference light back along the optical axis for the test light. In the Linnik-type, the beam splitter is positioned prior to the objective lens for the test surface (with respect to the input light) and directs the test and reference light along different paths. A separate objective lens is used to focus the reference light to the reference lens. In other words, the beam splitter separates the input light into the test and reference light, and separate objective lenses then focus the test and reference light to respective test and reference surfaces. Ideally the two objective lenses are matched to one another so that the test and reference light have similar aberrations and optical paths.

In other embodiments, the interferometry system can instead use a different type of interference objective, such as a Michelson objective, in which the beam splitter directs the reference light away from the optical axis of the test light (e.g., the beam splitter can be oriented at 45 degrees to the input light so the test light and reference travel at right angles to one another). In such cases, the reference surface can be positioned outside of the path of the test light.

Additional interferometer configurations are also possible. For example, the system can be configured to collect test light that is transmitted through the test sample and then subsequently combined with reference light. For such embodiments, for example, the system can implement a Mach-Zehnder interferometer with dual microscope objectives on each leg.

The light source in the interferometer may be any of: an incandescent source, such as a halogen bulb or metal halide lamp, with or without spectral bandpass filters; a broadband laser diode; a light-emitting diode; a combination of several light sources of the same or different types; an arc lamp; any source in the visible spectral region; any source in the IR spectral region, particularly for viewing rough surfaces & applying phase profiling; and any source in the UV spectral region, particularly for enhanced lateral resolution. For broadband applications, the source preferably has a net spectral bandwidth broader than 5% of the mean wavelength, or more preferably greater than 10%, 20%, 30%, or even 50% of the mean wavelength. For tunable, narrow-band applications, the tuning range is preferably broad (e.g., greater than 50 nm, greater than 100 nm, or greater than even 200 nm, for visible light) to provide information over a wide range of wavelengths, whereas the spectral width at any particular setting is preferable narrow, to optimize resolution, for example, as small as 10 nm, 2 nm, or 1 nm. The source may also include one or more diffuser elements to increase the spatial extent of the input light being emitted from the source.

Furthermore, the various translations stages in the system, such as translation stage 150, may be: driven by any of a piezo-electric device, a stepper motor, and a voice coil; implemented opto-mechanically or opto-electronically rather than by pure translation (e.g., by using any of liquid crystals, electro-optic effects, strained fibers, and rotating waveplates) to introduce an optical path length variation; any of a driver with a flexure mount and any driver with a mechanical stage, e.g. roller bearings or air bearings. As noted above, while the phase-shifting for the scanning interferometry signal is often done by using a mechanical translation stage, it is also possible to vary the phase between the test and reference legs of the interferometer by varying the wavelength of the source when there is a non-zero optical path length difference between the test and reference legs.

The electronic detector can be any type of detector for measuring an optical interference pattern with spatial resolution, such as a multi-element CCD or CMOS detector.

Any of the computer analysis methods described above can be implemented in hardware or software, or a combination of both. The methods can be implemented in computer programs using standard programming techniques following the method and figures described herein. Program code is applied to input data to perform the functions described herein and generate output information. The output information is applied to one or more output devices such as a display monitor. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The analysis method can also be implemented as a computer-readable storage medium, configured with a computer program, where the storage medium so configured causes a computer to operate in a specific and predefined manner to perform the functions described herein. While the specific descriptions above often refer to a scanning interferometry signal for which limited coherence in the interferometry system causes localization of the interference fringes; for many embodiments, it is also possible to extract information about complex surface features from interferometry signal(s) not having such fringe localization.

For example, interferometry signals from different locations of the test object that do not have fringe localization can still be used to generate an apparent surface profile for the test object, and that apparent surface profile, or information derived there from, can be compared to models of the expected response for different values of lateral surface features of the test object that are not-resolved or obscured in the apparent surface profile to determine information about such under-resolved features in much the same way as that described above for low coherence scanning interferometry signals. Techniques for extracting surface profile information from such "high" coherence interferometry signals are generally referred to as phase shifting interferometry (PSI) algorithms, and are well-known in the art. See, for example, the background and contents of U.S. Pat. No. 6,359,692, entitled "METHOD AND SYSTEM FOR PROFILING OBJECTS HAVING MULTIPLE REFLECTIVE SURFACES USING WAVELENGTH-TUNING PHASE-SHIFTING INTERFEROMETRY," the contents of which are incorporated herein by reference. To generate the interferometry data for such PSI analysis, the interferometry signal for a given pixel can be generating by mechanically varying the optical path length difference between the reference and measurement legs, or by varying the wavelength of the light for a fixed, non-zero optical path length difference between the reference and measurement legs.

A number of embodiments of the invention have been described. Nevertheless, it will be understood that various modifications may be made without departing from the spirit and scope of the invention.

What is claimed is:

1. A computer-implemented method comprising:
using a processor in the computer, comparing information derivable from multiple interferometry signals corresponding to different surface locations of a test object to information corresponding to multiple models of the test object, wherein the multiple models are parameterized by a series of characteristics that relate to one or more under-resolved lateral features of the test object; and
outputting information about the under-resolved surface feature based on the comparison.

2. A computer-implemented method for determining one or more spatial properties of a grating structure on a test object, wherein the grating structure comprises line elements having widths smaller than 400 nm so that the line elements are not fully resolved by an interference microscope, the method comprising using the computer to carry out steps comprising:
determining an apparent height for a collection of at least some of the grating lines from interference signals at different locations of the test object measured by the interference microscope;
providing an expected response for the interference microscope for different possible values for the properties of the grating structure, wherein the expected response includes contributions from under-resolved line elements of the grating structure;
comparing the apparent height to the expected response for the different possible values to determine information about the spatial properties of a grating structure; and
outputting the determined information about the spatial properties of the grating structure.

3. A computer-implemented method comprising using the computer to carry out steps comprising:
determining one or more apparent properties of a test surface from interferometry signals produced by an interferometry system;
comparing the apparent properties determined from the interferometry signals to an expected response for the interferometry system for different possible values for one or more under-resolved features of the test surface; and
outputting information about the one or more under-resolved features of the test surface based on the comparison.

4. A computer-implemented method comprising using the computer to carry out steps comprising:
comparing information derivable from a scanning interferometry signal for a first surface location of a test object to information corresponding to multiple models of the test object; and
outputting information about the test object based on the comparison,
wherein the multiple models are parameterized by a series of characteristics for the test object;
wherein the information corresponding to the multiple models comprises information about at least one amplitude component of a transform of a scanning interferometry signal corresponding to each of the models of the test object.

5. A computer-implemented method comprising using the computer to carry out steps comprising:
comparing information derivable from a scanning interferometry signal for a first surface location of a test object to information corresponding to multiple models of the test object, and
outputting information about the test object based on the comparison,
wherein the multiple models correspond to a fixed surface height for the test object at the first location and are parameterized by a series of characteristics for the test object different from the fixed surface height.

6. A computer-implemented method comprising using the computer to carry out steps comprising:
comparing information derivable from a scanning interferometry signal for a first surface location of a test object to information corresponding to multiple models of the test object; and
outputting information about the test objected based on the comparison,
wherein the multiple models are parameterized by a series of characteristics for the test object,
wherein the comparing comprises accounting for systematic contributions to the scanning interferometry signal arising from a scanning interferometry system used to produce the scanning interferometry signal.

7. A computer-implemented method comprising using the computer to carry out steps comprising:
comparing information derivable from a scanning interferometry signal for a first surface location of a test object to information corresponding to multiple models of the test object, wherein the multiple models are parameterized by a series of characteristics for the test object, and outputting information about the test objected based on the comparison, wherein the derivable information being compared relates to a shape of the scanning interferometry signal for the first surface location of the test object.

8. A computer-implemented method comprising using the computer to carry out steps comprising:

comparing information derivable from a scanning interferometry signal for a first surface location of a test object to information corresponding to multiple models of the test object, wherein the multiple models are parameterized by a series of characteristics for the test object, and outputting information about the test objected based on the comparison, wherein the series of characteristics comprises a series of characteristics of the test object at a second surface location different from the first surface location.

9. A computer-implemented method comprising using the computer to carry out steps comprising:

comparing information derivable from a scanning interferometry signal for each of multiple surface locations of a test object to information corresponding to multiple models of the test object, wherein the multiple models are parameterized by a series of characteristics that relate to one or more under-resolved lateral features of the test object, and outputting information about the under-resolved surface feature based on the comparison.

10. A computer-implemented method comprising using the computer to carry out steps comprising:

comparing information derivable from a scanning interferometry signal for a first surface location of a test object to information corresponding to multiple models of the test object; and outputting information about the test object based on the comparison, and wherein comparing information includes comparing information derivable from a scanning interferometry signal within a frequency domain to a frequency-domain representation of the model and comparing information within a scan domain to a scan-domain representation of the model.

* * * * *

UNITED STATES PATENT AND TRADEMARK OFFICE
CERTIFICATE OF CORRECTION

PATENT NO. : 7,684,049 B2 Page 1 of 1
APPLICATION NO. : 12/017531
DATED : March 23, 2010
INVENTOR(S) : Peter J. De Groot et al.

It is certified that error appears in the above-identified patent and that said Letters Patent is hereby corrected as shown below:

Column 58
Claim 6, line 53, replace "objected" with --object--

Column 59
Claim 7, line 1, replace "objected" with --object--
Claim 8, line 13, replace "objected" with --object--

Signed and Sealed this

First Day of June, 2010

David J. Kappos
*Director of the United States Patent and Trademark Office*